US012275929B2

(12) United States Patent
Lei et al.

(10) Patent No.: US 12,275,929 B2
(45) Date of Patent: Apr. 15, 2025

(54) CELL EXPANSION SYSTEM

(71) Applicant: NUtech Ventures, Lincoln, NE (US)

(72) Inventors: Yuguo Lei, Lincoln, NE (US); Hendrik Viljoen, Adams, NE (US)

(73) Assignee: NUtech Ventures, Lincoln, NE (US)

( * ) Notice: Subject to any disclaimer, the term of this patent is extended or adjusted under 35 U.S.C. 154(b) by 1063 days.

(21) Appl. No.: 16/981,050

(22) PCT Filed: Mar. 15, 2019

(86) PCT No.: PCT/US2019/022594
§ 371 (c)(1),
(2) Date: Sep. 15, 2020

(87) PCT Pub. No.: WO2019/178549
PCT Pub. Date: Sep. 19, 2019

(65) Prior Publication Data
US 2021/0017485 A1 Jan. 21, 2021

Related U.S. Application Data

(60) Provisional application No. 62/643,894, filed on Mar. 16, 2018.

(51) Int. Cl.
*C12M 1/00* (2006.01)
*C12M 1/12* (2006.01)
(Continued)

(52) U.S. Cl.
CPC ............ *C12M 41/46* (2013.01); *C12M 23/20* (2013.01); *C12M 25/14* (2013.01); *C12M 25/16* (2013.01);
(Continued)

(58) Field of Classification Search
CPC ...... C12M 41/46; C12M 23/20; C12M 25/14; C12M 25/16; C12M 33/00; C12N 5/0068;
(Continued)

(56) References Cited

U.S. PATENT DOCUMENTS 5,175,093 A   12/1992  Seifert
5,264,359 A   11/1993  Enami et al.
(Continued)

FOREIGN PATENT DOCUMENTS

CN    101130751 A  *  2/2008  ............ C12M 27/02
JP    2017217323 A  *  12/2017
WO    2017091662 A1    6/2017

OTHER PUBLICATIONS

Ikeda et al., "3D culture of mouse iPSCs in hydrogel core-shell microfibers." 2015 28th IEEE International Conference on Micro Electro Mechanical Systems (MEMS), pp. 463-464. (Year: 2015).*
(Continued)

*Primary Examiner* — Liban M Hassan
(74) *Attorney, Agent, or Firm* — Sandberg Phoenix & von Gontard, PC; Tracey S. Truitt

(57) ABSTRACT

A cell expansion system for culturing and expanding cells in hydrogel tubes is disclosed herein. The cell expansion system includes a cap having an extruder located within the cap and a tubular housing in fluid connection with the cap. The extruder has at least a first and second inlet. The tubular housing includes a cell compatible buffer. The extruder extends from within the cap into the tubular housing. The cell expansion system allows for expanding cells that can significantly reduce the production time and cost, while increasing the production capacity.

19 Claims, 60 Drawing Sheets

(51) Int. Cl.
*C12M 1/34* (2006.01)
*C12N 5/00* (2006.01)
(52) U.S. Cl.
CPC ........ *C12N 5/0068* (2013.01); *C12N 2500/14* (2013.01); *C12N 2533/40* (2013.01)
(58) Field of Classification Search
CPC ............ C12N 2500/14; C12N 2533/40; C12N 2537/10; C12N 11/04; C12N 11/08; C12N 11/084; C12N 11/10
See application file for complete search history.

(56) References Cited

U.S. PATENT DOCUMENTS

| | | |
|---|---|---|
| 5,387,522 A | 2/1995 | Vasington et al. |
| 2013/0189723 A1 | 7/2013 | Felder et al. |
| 2013/0206673 A1* | 8/2013 | Ying .................. A61M 1/3689 210/321.87 |
| 2017/0239191 A1 | 8/2017 | Vegas et al. |

OTHER PUBLICATIONS

Horiguchi et al., Alginate Encapsulation of Pluripotent Stem Cells Using a Co-axial Nozzel; Journal of Visualized Experiments, 2015, vol. 101, 7-pages.

* cited by examiner

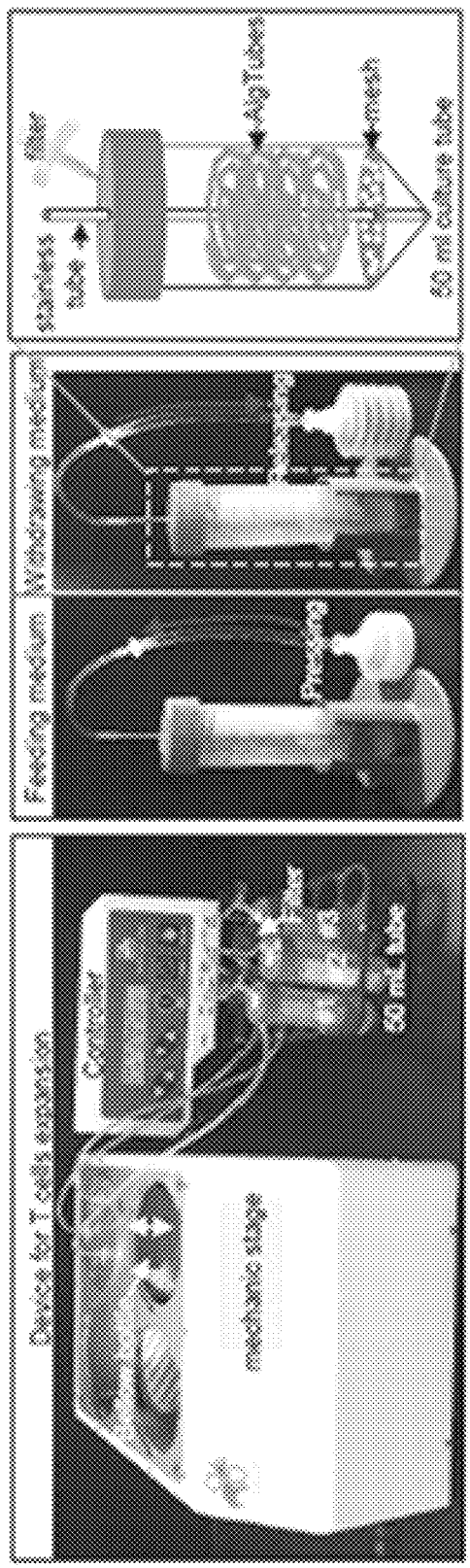

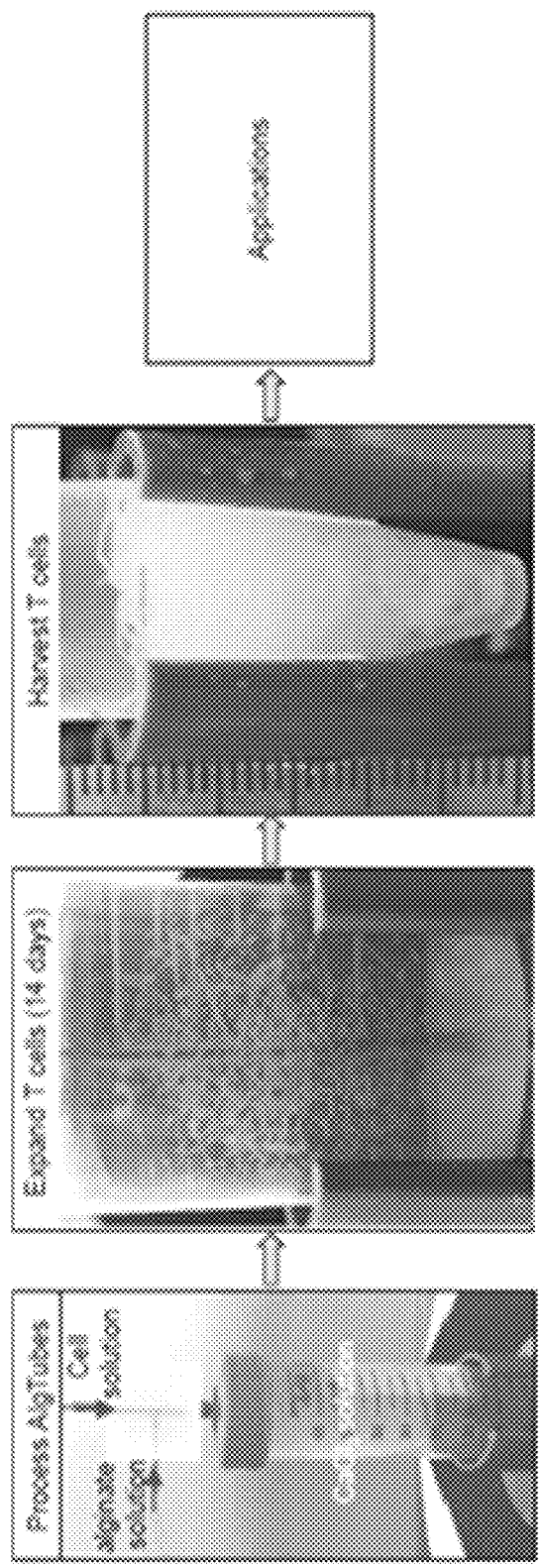

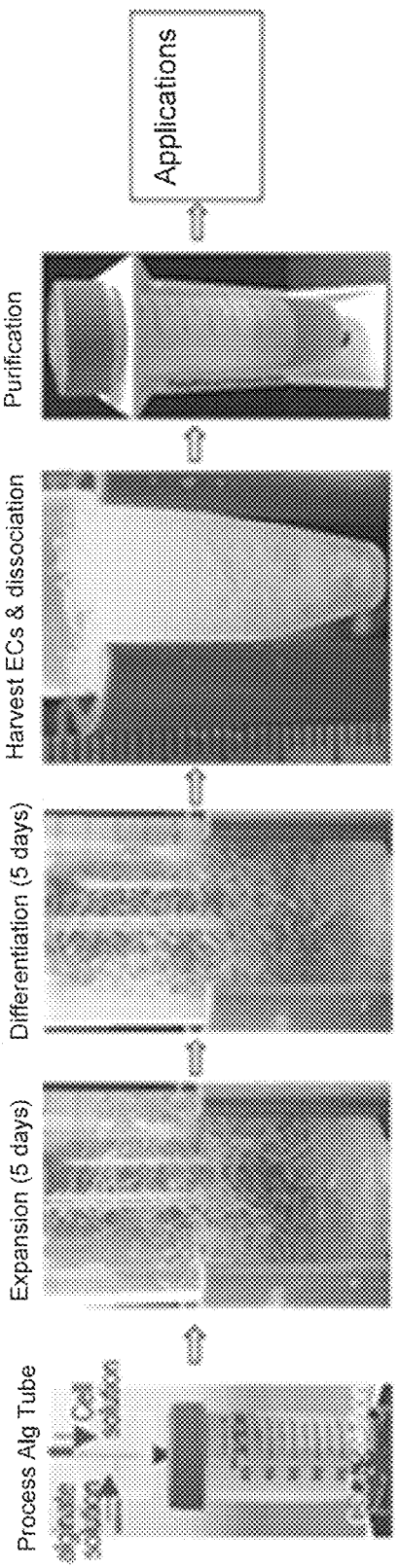

DA progenitor cells

Live Dead

LMX 1A FOXA2 DAPI

CELL EXPANSION SYSTEM

CROSS-REFERENCE TO RELATED APPLICATIONS

The present application claims priority to International Patent Application No. PCT/US2019/022594 (published as WO2019/178549), filed Mar. 15, 2019, which claims priority to U.S. Application Ser. No. 62/643,894 filed Mar. 16, 2018, which are hereby incorporated by reference in their entireties.

BACKGROUND OF THE DISCLOSURE

The present disclosure relates generally to using a cell expansion system for culturing and expanding cells in hydrogel tubes. Particularly, the system allows for expansion of cells in a cost effective and efficient manner. In one embodiment, the cells for expansion are primary human T cells for adoptive immunotherapy.

Adoptive immunotherapy refers to the transfer of immune cells (e.g. T lymphocytes) with antitumor activity into a patient to mediate tumor regression. Basic, translational and clinical studies have shown adoptive immunotherapy to be highly effective for treating many cancers, such as melanoma, cervical cancer, lymphoma, leukemia. However, the cost for manufacturing T cells with current cell culturing technologies is extremely high. For instance, one dose of a recently approved engineered T cells for treating children and young adults with B-cell acute lymphoblastic leukemia costs $475,000.

Two major sources of T cells: the tumor infiltrating lymphocytes (TILs) and genetically engineered T lymphocytes including T cells expressing the chimeric antigen receptor (CAR T cells) or the conventional T cell receptor (TCR T cells) are currently used for adoptive immunotherapy. For TILs-based therapy, TILs are first isolated from the patient's tumor, then activated and expanded in vitro to generate a clinically relevant number of cells that are infused back to the patient. Clinical studies have shown that TILs can mediate remarkable antitumor responses in patients with melanoma, cholangiocarcinoma and cervical cancer. For CAR T cell-based therapy, T cells are first isolated from the patient through leukapheresis, then activated and engineered to express CARs capable of specifically recognizing tumor cells' surface antigens, and expanded to clinically relevant numbers and infused back to the patient. CAR T cells recognizing CD19 antigens (anti-CD19 CAR T cells) have achieved huge success in treating B cell leukemia and lymphomas in clinical studies. Scientists are currently studying using T cells expressing CARs recognizing other tumor antigens, such as CD138, CD171, CEA, EGFRvIII, and ErbB to treat various solid tumors. TCR T cell-based therapy is very similar to CAR T cell therapy except that TCRs recognizing tumor antigens are expressed on the T cell surface. TCR T cells specific for NY-ESO1, MART-1 and gp100 antigen have shown excellent anti-tumor responses in patients with melanoma and sarcoma in clinical trials.

Conventionally, to engineer the T cells, gene expression vectors for TCRs or CARs are delivered to cells with retrovirus, lentivirus and mRNAs through transfection. Currently, there are three major culture systems used to expand therapeutic T cells. The first is the WAVE bioreactor (GE Healthcare Life Science), in which cells are suspended in the culture medium contained in a gas-permeable plastic bag that is mildly rocked. T cells can grow up to a moderate density ($\sim 1 \times 10^7$ cells/mL) and up to 25-liter culture volume can be achieved with this technology. However, how the hydrodynamic stresses generated by the rocking affect the cultured T cells in this system is unknown. The second is the G-Rex bioreactor, in which cells are statically suspended in the culture medium in a bottle with a gas-permeable membrane bottom. This system is hydrodynamic stress-free, however, only yields $\sim 1.4 \times 10^9$ cells in a one liter bottle. Additionally, the cell growth kinetics is dependent on if the cells are disturbed (e.g. cell sampling) during the culture. The third is the CliniMACS Prodigy culture system, which aims to fully integrate and automate the cell manufacturing. This system consists of a cell separation column for isolating T cells and a cell culture container, where cells are suspended in the agitated culture medium, transduced and expanded. This system has hydrodynamic stresses and its volumetric cell yield is moderate (e.g. $\sim 5 \times 10^6$ cells/mL).

Based on the foregoing, it would be advantageous to develop a cell expansion system that can significantly reduce the manufacturing cost and increase the manufacturing capacity for the widespread application of adoptive immunotherapy. It would further be advantageous if the expansion system could be used for either scale-up (i.e., large production in a single tube) or scale-out (i.e., large number of small tubes, each one operated independently from another) production. Finally, it would be advantageous if the cell expansion system could be used to expand other human and mammalian cells.

BRIEF DESCRIPTION

The present disclosure is generally directed to a cell expansion system and to methods of using the system. Particularly, the system allows for culturing and expanding cells in hydrogel tubes. Particularly, this methodology allows for expansion of cells in a cost effective and efficient manner.

In one embodiment, the present disclosure is directed to a cell expansion system for expanding cells. The system comprises: a cap comprising: an extruder comprising at least a first inlet and at least a second inlet, the first inlet operable for introducing a cell solution into the extruder, the second inlet operable for introducing a hydrogel-forming solution into the extruder; and a tubular housing in fluid connection with the extruder of the cap, wherein the tubular housing comprises a cell compatible buffer.

In another embodiment, the present disclosure is directed to a method of expanding cells. The method comprises culturing cells in the cell expansion system described above. In one embodiment, the method includes: extruding the cell solution and the hydrogel-forming solution into a cell compatible solution, the cell compatible solution crosslinking polymers within the hydrogel-forming solution to form hydrogel fibers; suspending the fibers including cells from the cell solution in cell culture medium or cell compatible buffer in the tubular housing; and culturing the cells.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 1A & 1B show that the setup for processing AlgTubes has two syringe pumps, a custom-made micro-extruder and a $CaCl_2$ buffer. A cell solution and an alginate solution is pumped into the central channel and side channel of the micro-extruder, respectively, to form a coaxial core-shell flow that is extruded through the nozzle into the $CaCl_2$ buffer. The shell alginate flow is crosslinked by $Ca^{2+}$ ions to form an alginate hydrogel tube within seconds. FIG. 1C depicts design principles of AlgTubes. Cells are suspended and cultured in AlgTubes that are suspended in the cell culture medium in a culture vessel. The tubes provide free microspaces that allow cells to interact with each other and expand. They also protect cells from hydrodynamic stresses and confine the cell mass <400 pm (in radial diameter) to ensure efficient mass transport. Cell culture medium can efficiently diffuse through the hydrogel shell. FIGS. 1D & 1E show that in AlgTubes, T cells first associate to form small clusters that subsequently grow and fill the tubes. Scale bar: 200 pm.

FIG. 5A is an image of an assembled micro-extruder. FIGS. 5B & 5C are an illustration (FIG. 5B) and photograph (FIG. 5C) of a micro-extruder with 8 nozzles for simultaneously extruding 8 AlgTubes.

FIGS. 6A-6C are microscopy images of day 2 T cells grown with ImmunoCult™-XF T cells expansion medium (ImmunoCult) and anti-CD3/CD28 or anti-CD3/CD28/CD2 activators, or with CTS™ OpTmizer™ T cells expansion medium (CTS) and anti-CD3/CD28-Dynabeads activators in static 3D (FIG. 6A), dynamic 3D (FIG. 6B) suspension culturing or AlgTubes (FIG. 6C). Cells were seeded at $1\times 10^6$ cells/ml. Scale bars: 200 µm. FIG. 6D depict the cumulative cell expansion folds. For static or dynamic 3D suspension culturing, cells were mechanically dissociated and seeded into multiple wells at $1\times 10^6$ cells/ml on day 3, 6, 9 and 12, respectively.

FIG. 7A provides that the equations used to predict the shell thickness are based on the volumetric flow rates of the cell solution and alginate solution and the tube outer diameter. FIG. 7B shows that the experimental shell thickness fits well with the predicted data. FIG. 7C are phase images of T cells in AlgTubes with varied shell thickness (20, 40, and 60 µm) on day 0. Scale bar: 200 µm. FIG. 7D are phase images of T cells in AlgTubes with varied diameters (400, 250, and 120 µm) on day 0 and 14. Scale bar: 200 µm. FIGS. 7E & 7F depict expansion folds and volumetric yields on day 14 in AlgTubes with varied shell thickness or diameter.

FIGS. 8A-8C are microscopy images of T cells from donor #1 grown in AlgTubes (FIG. 8A), static 3D (FIG. 8B) and dynamic 3D (FIG. 8C). Scale bar: 200 µm. FIGS. 8D-8F are photographs of the white cell masses in a 6-well plate. Scale bar: 1 cm. FIGS. 8G & 8H depict the cell density and cumulative expansion fold on different days of a 14-day culture with AlgTubes, static 3D and dynamic 3D suspension culturing. ***: p<0.001.

FIGS. 9A-9C are microscopy images of T cells from donor #2 grown in AlgTubes (FIG. 9A), static 3D (FIG. 9B) and dynamic 3D (FIG. 9C). Scale bar: 200 µm. FIGS. 9D-9F are photographs of the white cell masses in a 6-well plate. Scale bar: 1 cm.

FIGS. 10A-10C are microscopy images of T cells from donor #2 grown in AlgTubes (FIG. 10A), static 3D (FIG. 10B) and dynamic 3D (FIG. 10C). Scale bar: 200 µm. FIGS. 10D-10F are photographs of the white cell masses in a 6-well plate. Scale bar: 1 cm.

FIG. 11A depicts the percentage of dead cells (normalized to the initial cells) on day 3, 6, 9, 12 and 14 in AlgTubes, static 3D and dynamic 3D suspension culturing. FIG. 11B depicts the percentage of cells in G1, S and G2/M on day 3 of the 14-day culture as analyzed with propidium iodide staining and flow cytometry. FIG. 11C depicts the percentage of CD3+, CD4+ and CD8+ T cells in the day 14 cells. FIG. 11D shows cytokines in day 14 medium. FIG. 11E depicts the percentage of tail DNA in 138 randomly selected nuclei for each culture condition as quantified using Comet assay. ***: p<0.001; *: p<0.05.

FIGS. 12A-12C depict the percentage of CD3+, CD4+ and CD8+ T cells in AlgTubes (FIG. 12A), static 3D (FIG. 12B) and dynamic 3D (FIG. 12C) from donor #1, #2 and #3.

FIG. 13A shows that the head and tail of the comet correspond to the intact and broken DNA of a nucleus. FIGS. 13B & 13C show 30 randomly selected nuclei for each sample.

FIG. 14A are microscopy images of T cells from donor #1 grown in AlgTubes at passage 3. Scale bar: 200 µm. FIG. 14B is a photograph of the white cell masses in one AlgTube in a 6-well plate. Scale bar: 1 cm. FIGS. 14C & 14D depict the cell density and expansion fold on day 14 of passage 1, 2 and 3. FIG. 14E depicts the percentage of CD3+, CD4+ and CD8+ T cells at passage 1 and 3. FIG. 14F depict cytokines in day 14 medium of passage 1 and 3. FIG. 14G depicts the cumulative expansion folds.

FIG. 15A are microscopy images of T cells from donor #2 grown in AlgTubes at passage 3. Scale bar: 200 µm. FIG. 15B is a photograph of the white cell masses in one AlgTube in a 6-well plate. Scale bar: 1 cm. FIGS. 15C &

Figure 15A:
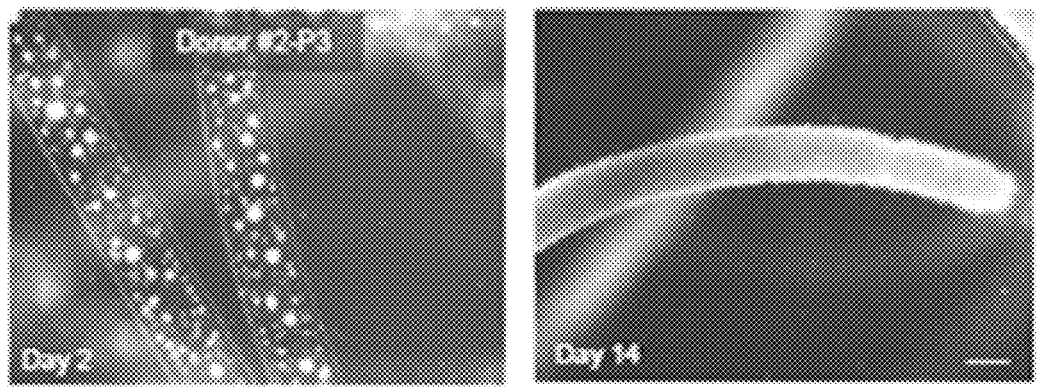
FIGS. 15A-15D depict long-term culturing of T cells in AlgTubes.
Figure 15B:
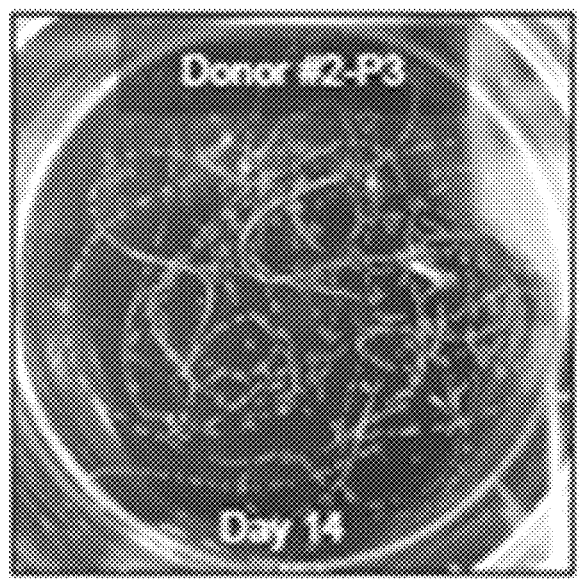
Figure 15C:
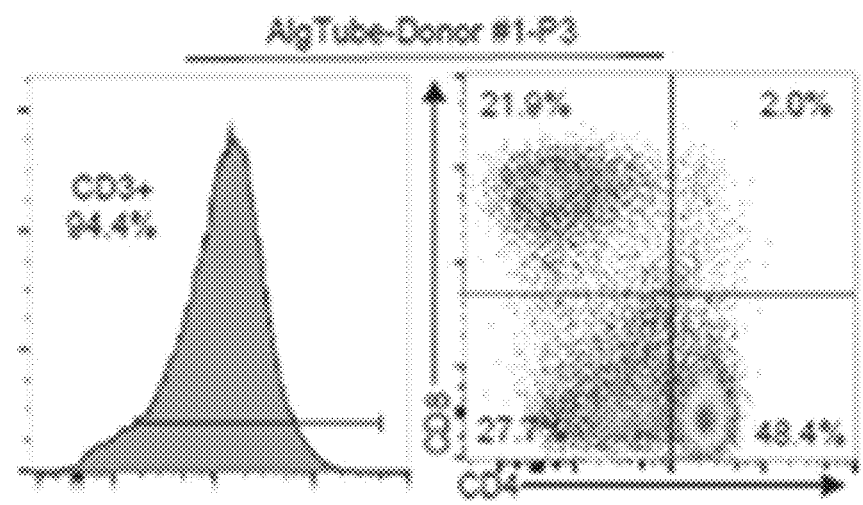
Figure 15D:
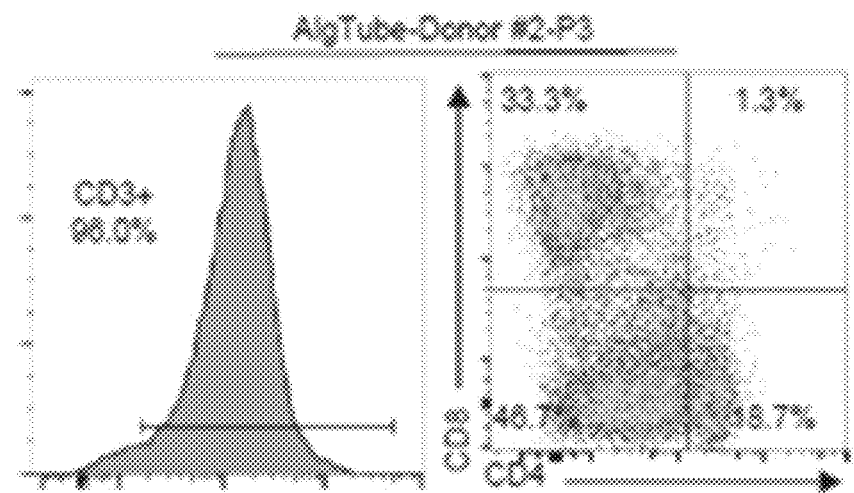

15D depict flow cytometry analysis of CD3+, CD4+ and CD8+ T cells in AlgTube at passage 3 from donor #1 (FIG. 15C) and #2 (FIG. 15D).

FIGS. 16A-16F depict automated T cell expansion. FIGS. 16A-16C depict the prototype cell expansion system consists of a mechanic stage, a controller, a bellow bottle and a conical tube. Medium was stored in the plastic bellow bottle that could be pressed to flow the medium into, or released to withdraw, the medium from the conical tube. The controller could be programmed for the pressing and releasing speed, as well as the duration of the interval between the pressing and releasing. FIGS. 16D-16F depict that on day 1, AlgTubes with T cells were processed into the 50 mL conical tube (FIG. 16D), where cells were expanded for 14 days (FIG. 16E) before harvest through adding EDTA solution (FIG. 16F). The whole process was completed in the closed 50 mL conical tube. Three conical tubes were used to produce T cells from three donors.

Figure 17A:
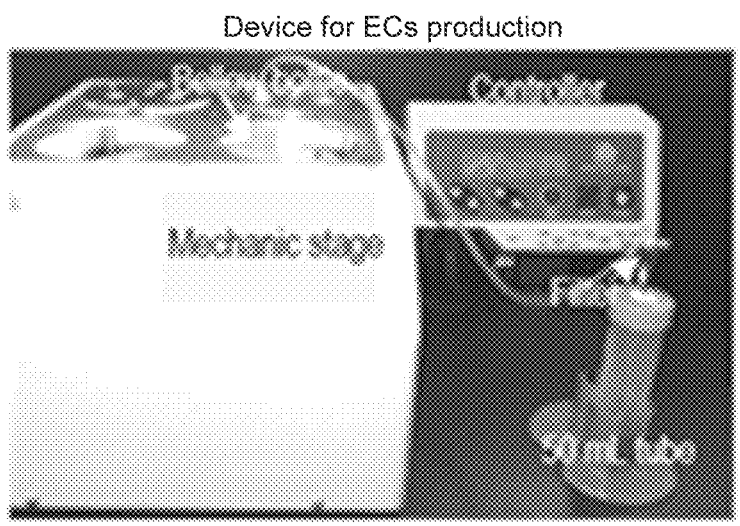
Figure 17B:
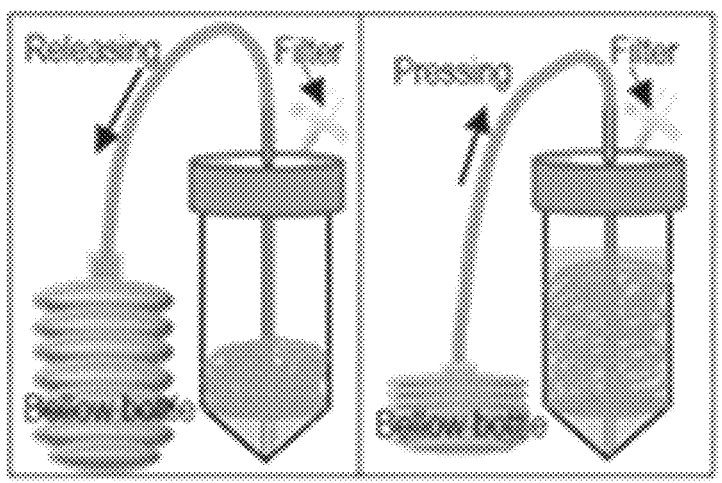
Figure 17H:
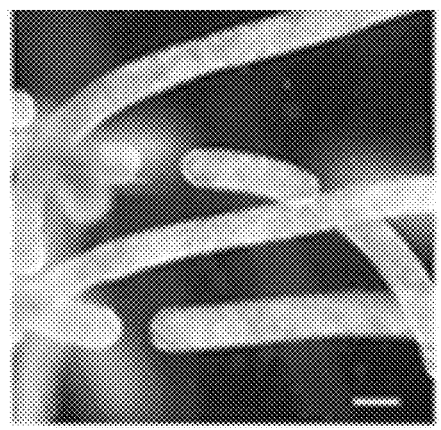
Figure 17I:
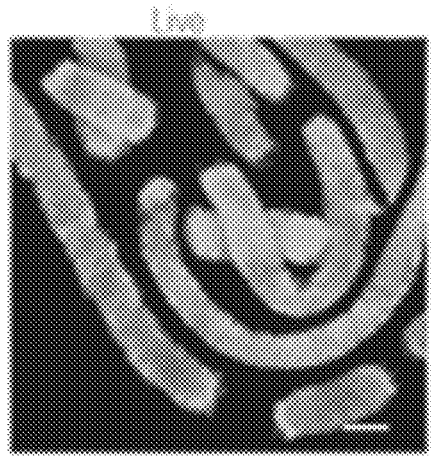
Figure 17J:
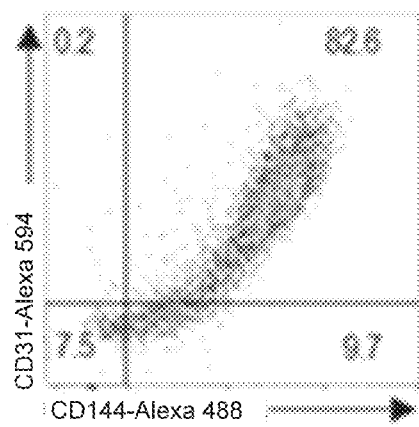
Figure 17K:
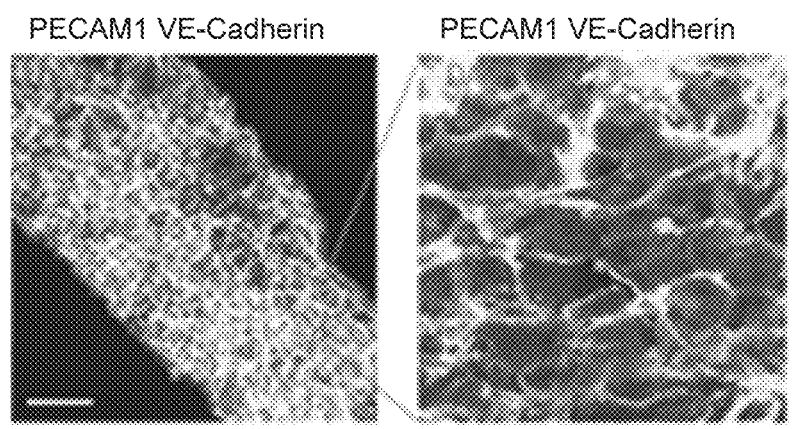
Figure 17L:
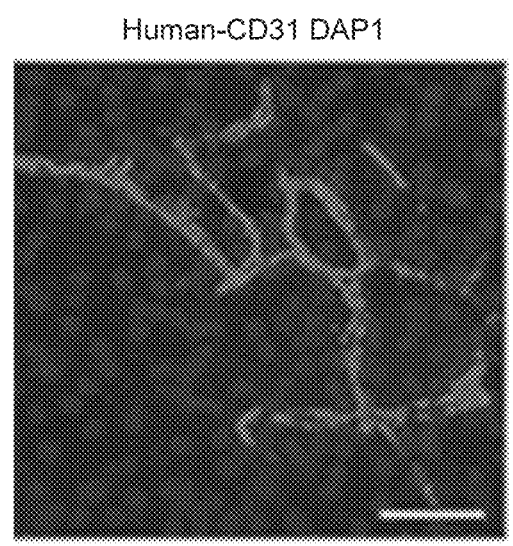

FIGS. 17A-17L depict making human pluripotent stem cells (hPSCs) derived endothelial cells (ECs). FIGS. 17A & 17B depict a cell expansion system of the present disclosure consisting of a mechanic stage, a controller, a bellow bottle and a 50 mL conical tube. Medium was stored in the plastic bellow bottle that could be pressed to flow the medium into, or released to withdraw, the medium from the conical tube. The controller could be programmed for the pressing and releasing speed, as well as the duration of the interval between the pressing and releasing. FIGS. 17C-17G depict that on day 0, single hPSCs mixed with 1.5% HA solution and 1.5% alginate solution were pumped into the central and side channel of the home-made micro-extruder respectively, and extruded into a $CaCl_2$ buffer (100 mM) (FIG. 17C). Cells were cultured in E8 medium for 5 days (FIG. 17D), followed by additional 5 days of EC differentiation medium (FIG. 17E). Medium was continuously perfused. On day 10, alginate hydrogel were dissolved by 0.5 mM EDTA for 5 minutes. Cell masses were pelleted by centrifugation. Cell masses were dissociated into single cells through incubating in Accutase at 37° C. for 10 minutes (FIG. 17F). Magnetic beads coated with anti-SSEA4 antibodies were added to pull down the undifferentiated SSEA4+ hPSCs with a magnetic cell separator (FIG. 17G). FIGS. 17H-17K depict phase image (FIG. 17H), live/dead staining (FIG. 17I), flow cytometer analysis (FIG. 17J) and immunostaining (FIG. 17K) of day 10 cells. Scale bars, 200 μm and 100 μm, respectively. FIG. 17L shows that when transplanted subcutaneously with a Matrigel matrix, ECs formed nice vascular structures. H9s were used in this Figure. Scale bar, 50 μm.

Figure 18A:
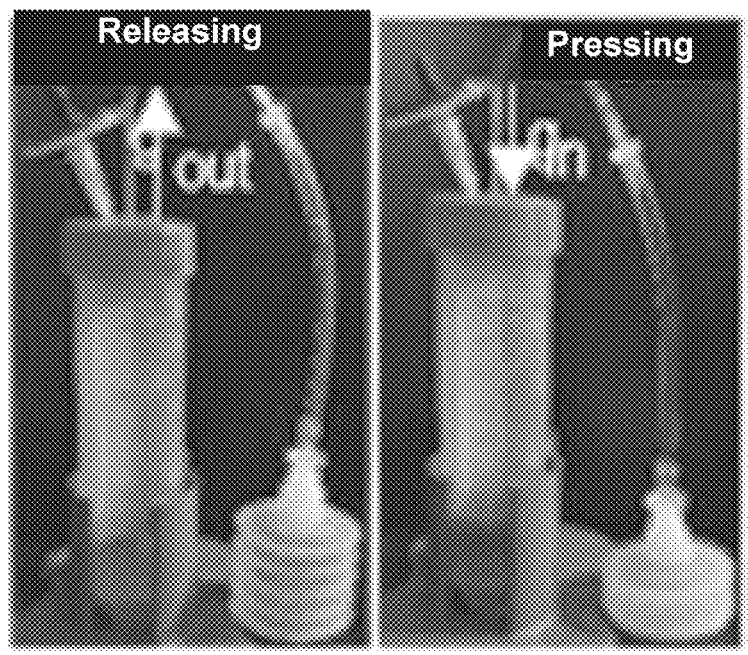
Figure 18B:
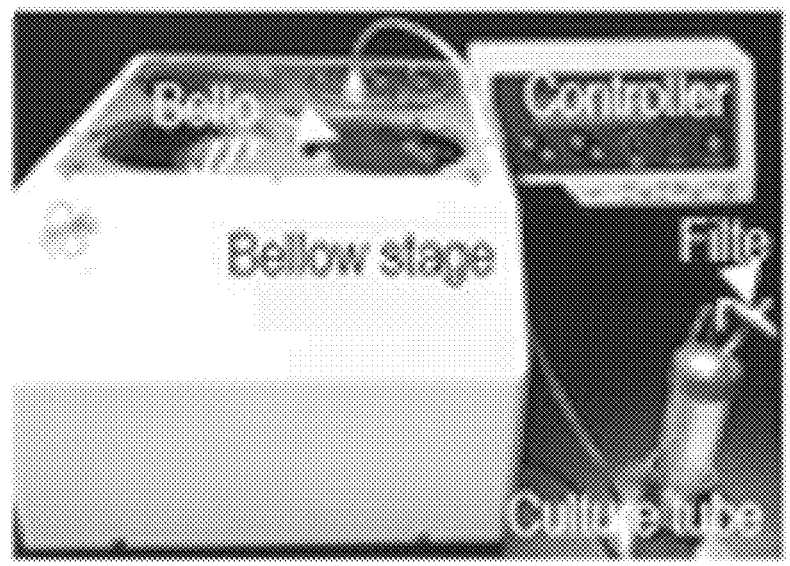
Figure 18C:
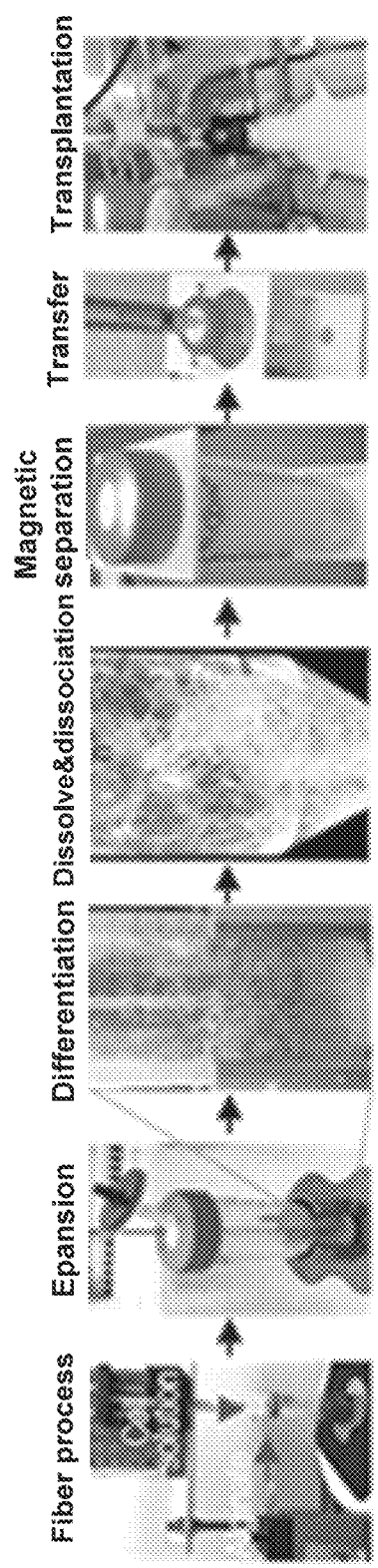
Figure 18D:
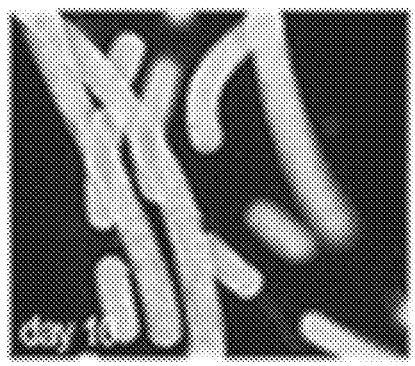
Figure 18E:
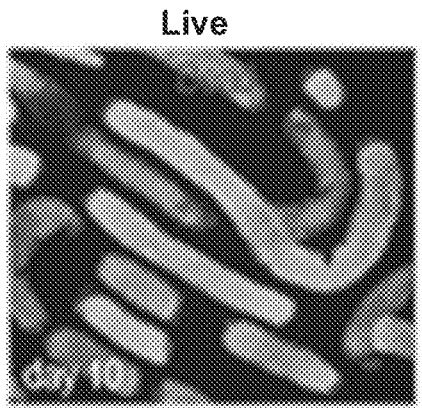
Figure 18F:
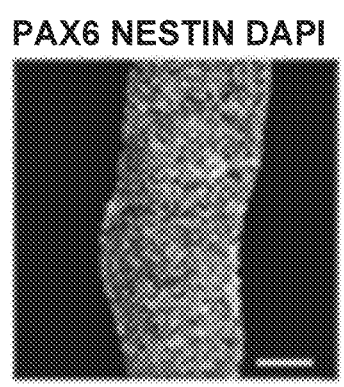

FIGS. 18A-18H depict making human pluripotent stem cells (hPSCs) derived neural stem cells (NSCs). FIGS. 18A & 18B depict a cell expansion system of the present disclosure consisting of a mechanic stage, a controller, a bellow bottle and a 50 mL conical tube. Medium was stored in the plastic bellow bottle that could be pressed to flow the medium into, or released to withdraw, the medium from the conical tube. The controller could be programmed for the pressing and releasing speed, as well as the duration of the interval between the pressing and releasing. As shown in FIG. 18C, on day 0, single hPSCs mixed with 1.5% HA solution and 1.5% alginate solution were pumped into the central and side channel of the home-made micro-extruder respectively, and extruded into a $CaCl_2$ buffer (100 mM). Cells were cultured in E8 medium for 5 days, followed by additional 7 days of NSC induction medium. Medium was continuously perfused. On day 12, alginate hydrogel were dissolved by 0.5 mM EDTA for 5 minutes. Cell mass were pelleted by centrifugation. Cell masses were dissociated into single cells through incubating in Accutase at 37° C. for 10 minutes. Magnetic beads coated with anti-SSEA4 antibodies were added to pull down the undifferentiated SSEA4+ hPSCs with a magnetic cell separator. Purified cells in the supernatant were transferred into a new, closed tube and transported to the surgical room. NSCs were transplanted into the rat brain with a stereotactic injector. FIG. 18D depicts immunostaining of day 12 cells for NSCs markers, PAX6 and NESTIN. Scale bar, 50 μm. FIG. 18E shows that the cells pulled down by the magnetic anti-SSEA4 beads were positive for OCT3/4 and NANOG. Scale bar, 50 μm. FIG. 18F shows that transplanted cortical progenitors survived well in the rat brain 7 days post-transplantation and became HuNu+ and TUJ-1+ neurons 30 days post-transplantation. Scale bars, 400 μm and 50 μm, respectively.

Figure 19A:
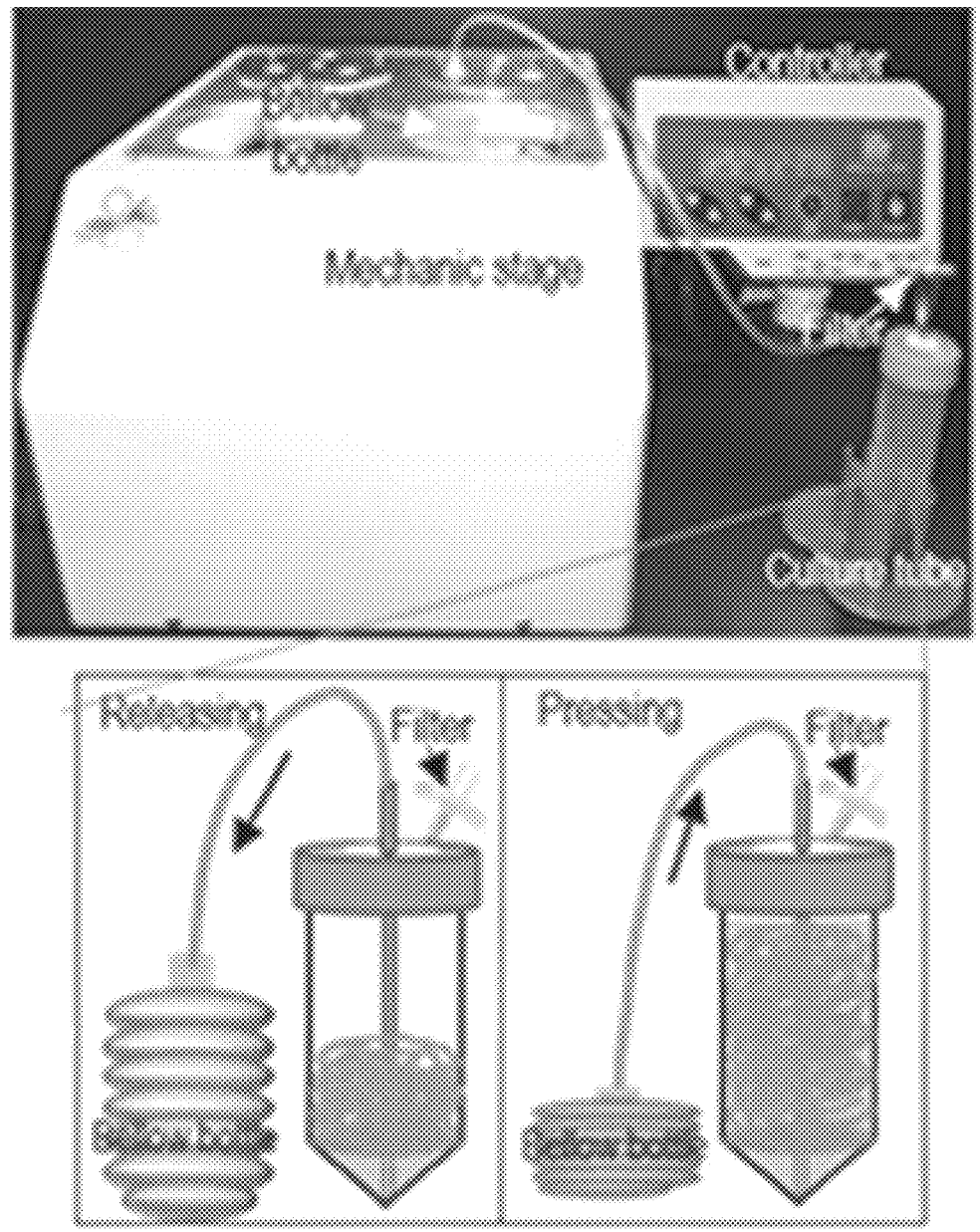
Figure 19B:
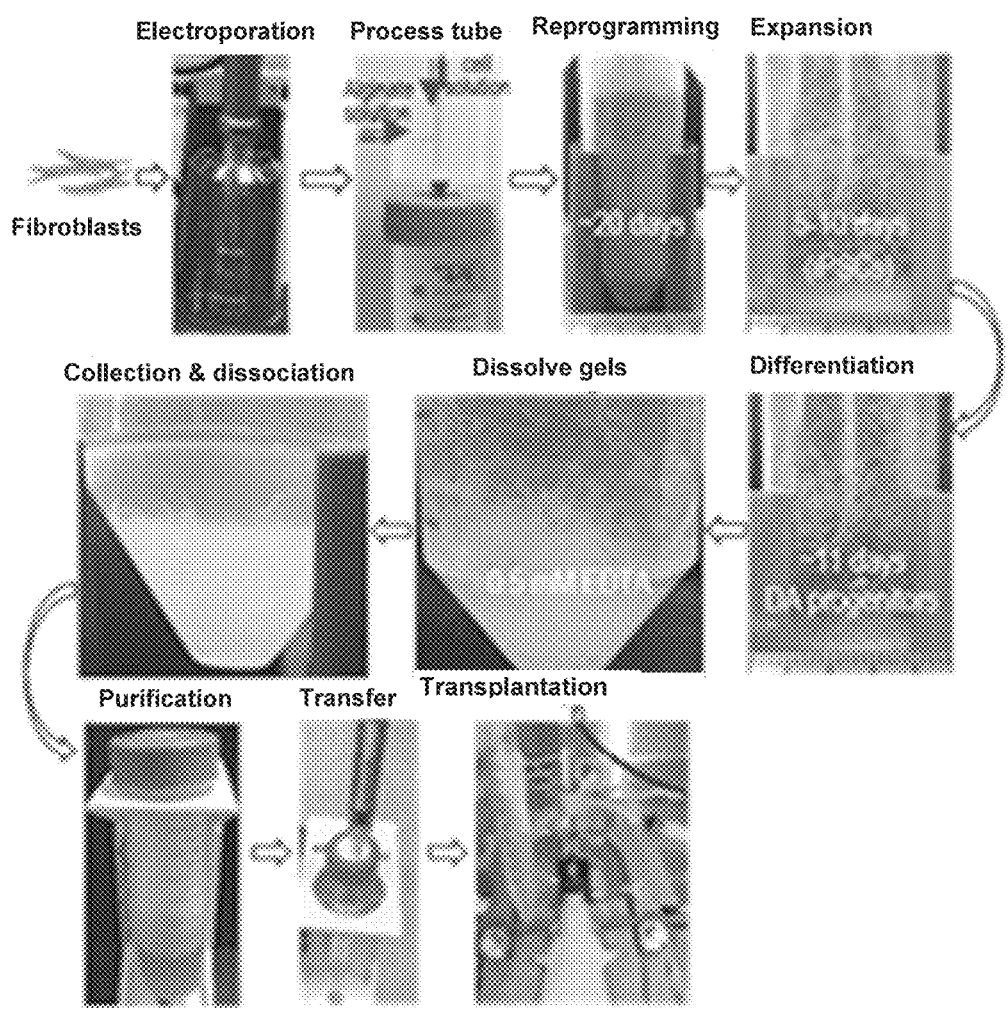
Figure 19C:
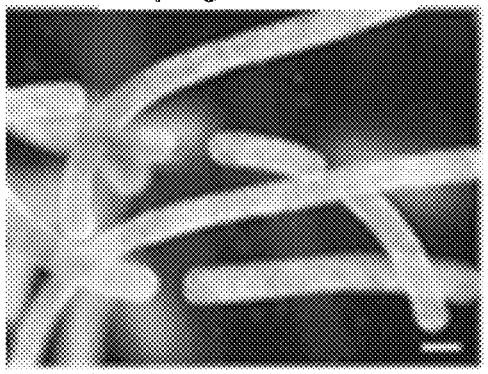
Figure 19D:
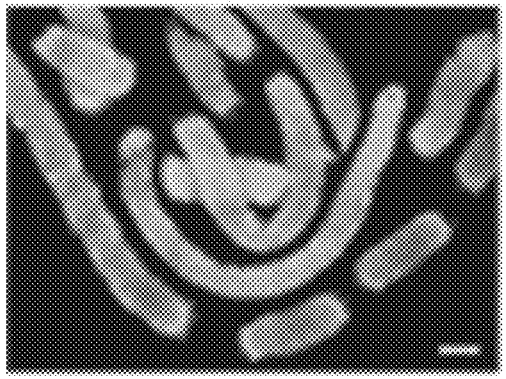
Figure 19E:
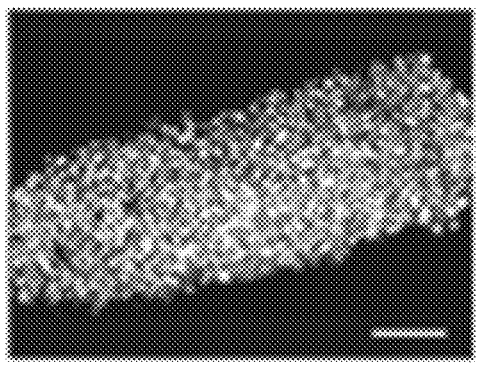
Figure 19F:
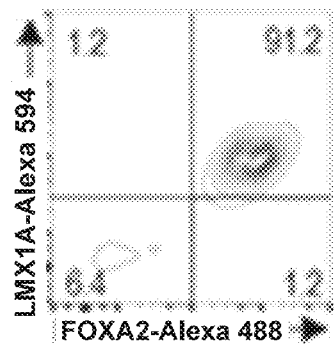
Figure 19G:
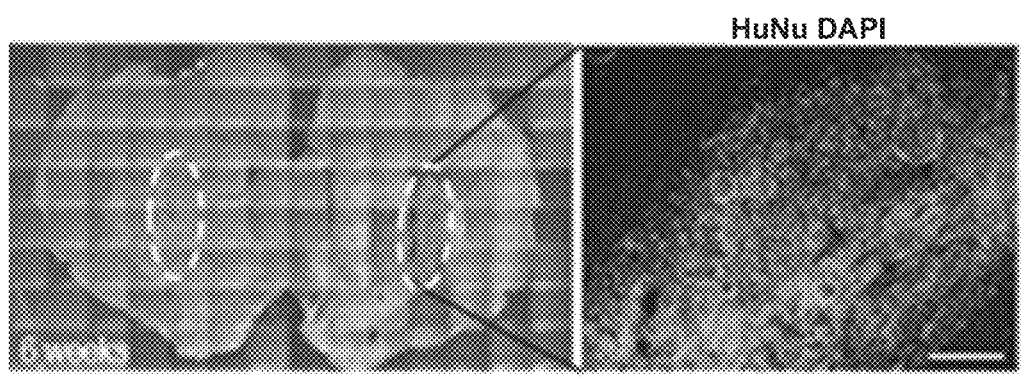
Figure 19H:
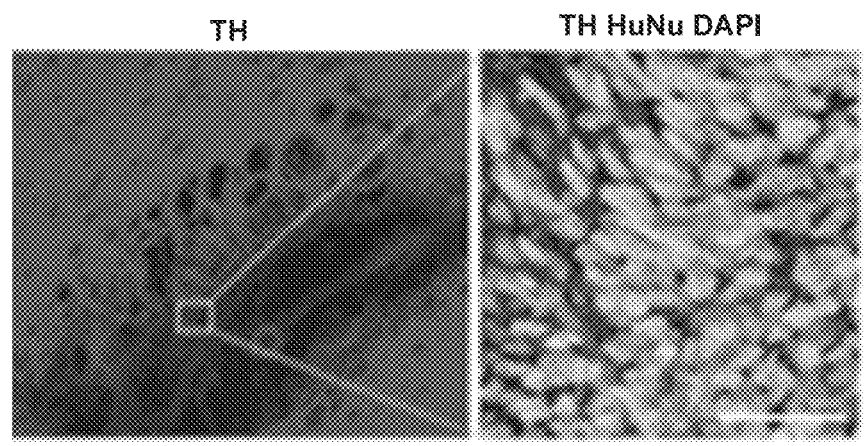

FIGS. 19A-19H depict a cell expansion system for the present disclosure for personalized cell production. FIG. 19A shows that the system consists of a mechanic stage, a controller, a bellow bottle and a 50-mL conical tube. FIG. 19B are pictures showing cell production with the system. FIGS. 19C & 19D are phase images and live/dead staining of day 11 DA progenitor cells. Scale bars, 200 μm. FIGS. 19E & 19F depict immunostaining (FIG. 19E) and flow cytometry analysis (FIG. 19F) of the day 11 cells for DA progenitor markers LMX1A and FOXA2. Scale bars, 100 μm. FIGS. 19G & 19H show that 6 weeks post-transplantation, cells survived well and matured into DA neurons. Scale bar, 200 μm and 100 μm, respectively.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The present disclosure is directed to an automatable cell expansion system for expanding cells that can significantly reduce the production time and cost, while increase the production capacity. It is designed to provide cells in a culture microenvironment that has no hydrodynamic stresses in order to produce cells at high yield, high quantity and high quality. It was previously found that culturing human cells under hydrodynamic stresses are highly detrimental to the cells and eliminating these hydrodynamic stresses leads to significant improvement in cell viability, growth rate, yield and quality. High yield can reduce the culture volume, and thus production cost, for each patient. Furthermore, reduction in culture volume allows for the development of a miniature device for automated cell production for large numbers of patients.

Cell Expansion Systems and Methods of Expanding Cells Using the Systems

Figure 1A:
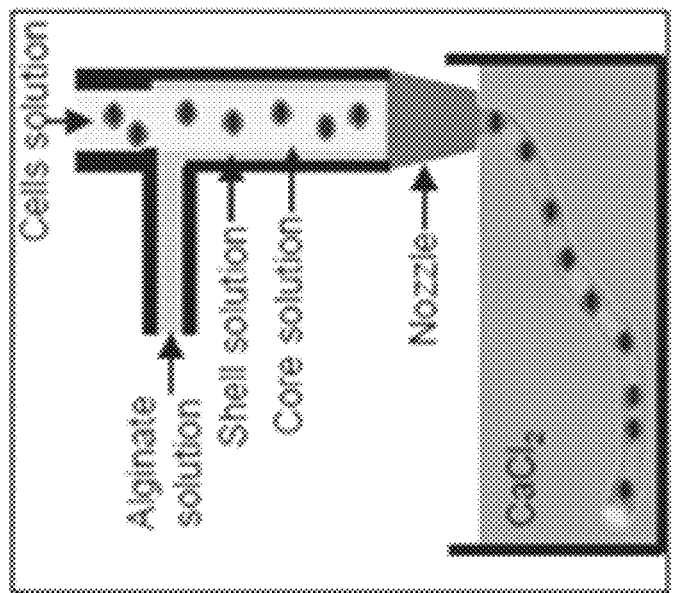
FIGS. 1A-1E depict T cells cultured in alginate hydrogel tubes (AlgTubes).
Figure 1B:
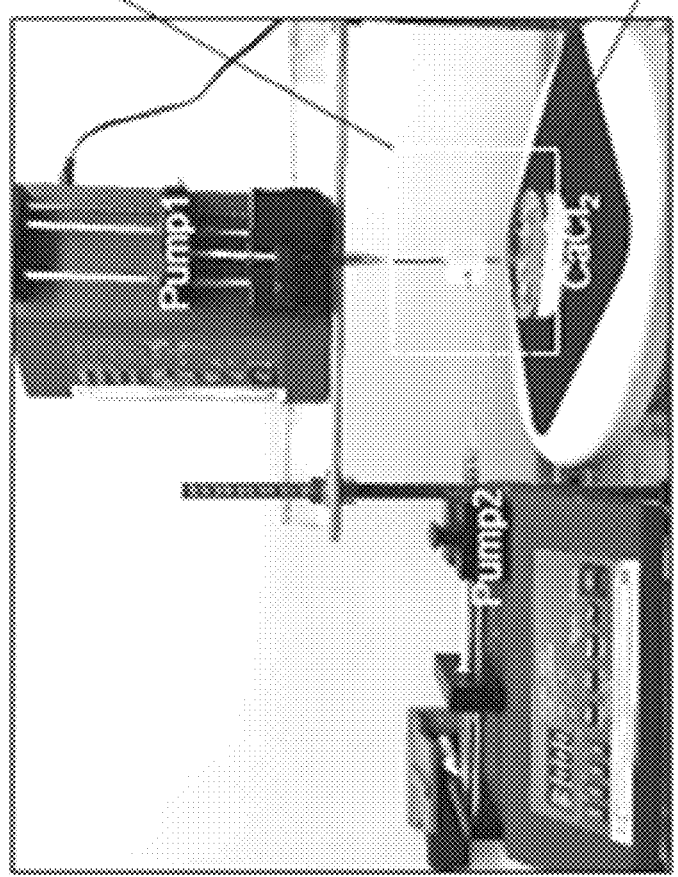
Figure 1C:
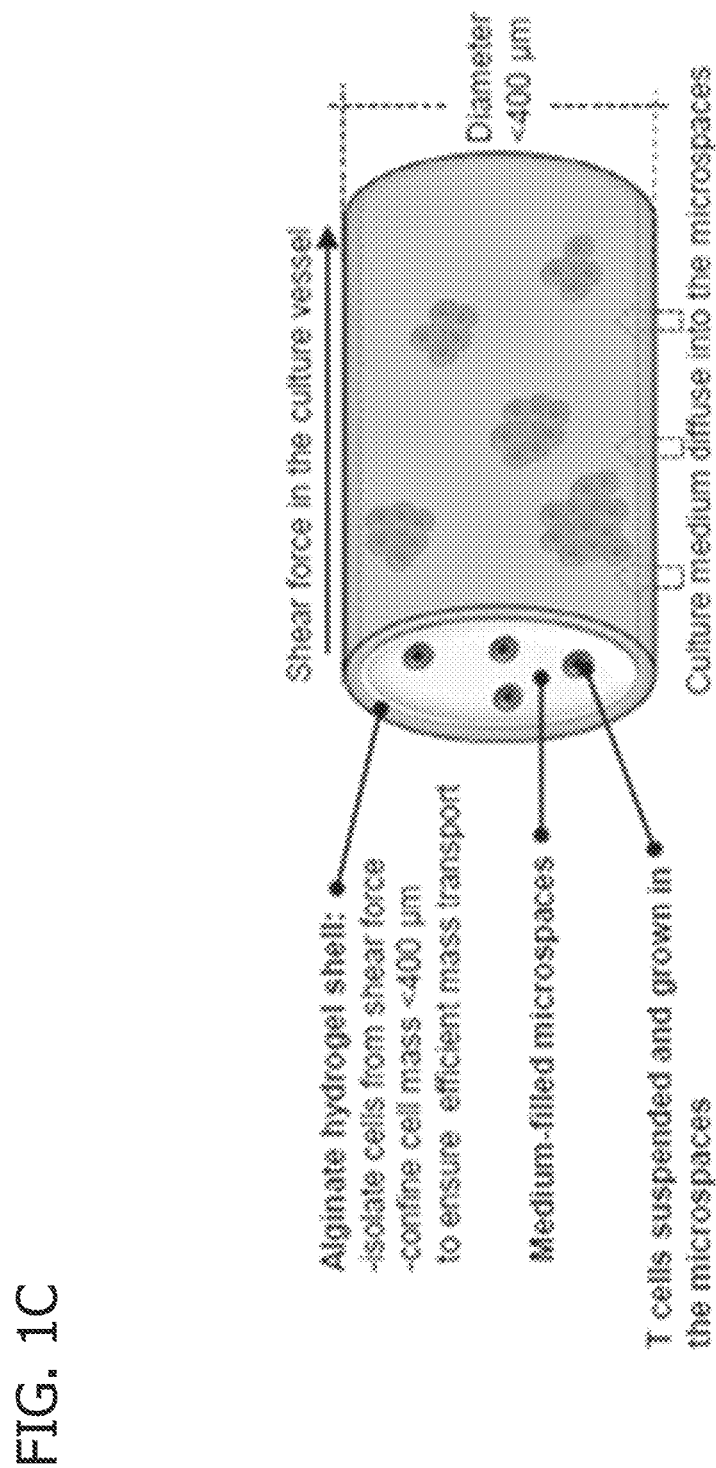

Generally, the methods of the present disclosure include processing into and culturing cells (with their activators) in a cell expansion system including microscale hydrogel tubes that are suspended in the cell culture medium in a culture vessel (FIGS. 1A & 1B). The hydrogel tubes create cell-friendly microspaces that allow cells to interact with each other and expand. Meanwhile, the hydrogel tubes protect cells from hydrodynamic stresses in the culture vessel. Further, the hydrogel tubes confine the cell masses (typically, to less than 400 μm in radial diameter) to ensure efficient mass transport during the entire culture (FIG. 1C).

Additionally, the cell expansion systems of the present disclosure are designed to be simple, scalable, defined, reproducible, cost-effective and compatible with the current Good Manufacturing Practices to make it commercially viable.

Non-limiting examples of cells that can be processed, cultured and expanded using the methods and systems described herein include mammalian cells, insert cells (e.g., drosophila S2 cells), plant cells, yeast cells, and bacterial cells. While described more fully using mammalian cells, especially human T cells, it should be recognized that the methods and systems described herein can be used with any of the above-listed types of cells without departing from the scope of the present disclosure.

As used herein, "mammalian cells" refer to cells derived from both humans and animals. Particularly suitable mammalian cells for use in the methods and systems of the present disclosure include, mammalian embryonic stem cells, mammalian induced pluripotent stem cells, mammalian naive pluripotent stem cells, cells differentiated from mammalian embryonic stem cells, mammalian induced pluripotent stem cells and mammalian naive pluripotent stem cells, mammalian cells reprogrammed from other cell types (e.g. human neurons reprogrammed from human fibroblasts), mammalian primary cells (e.g., human umbilical vein endothelial cells, cancer cells, T cells), mammalian tissue stem cells (e.g., mesenchymal stem cells, fetal neural stem cells), and mammalian cell lines (e.g., human embryonic kidney (HEK293) cells, Chinese hamster ovary (CHO) cells).

Microscale hydrogel tubes are prepared as known in the art. By way of example, in one particular embodiment, the tubes are prepared as hollow fibers prepared from alginate polymer material. Suitable alginate polymer material for use in preparing the tubes include any commercially available or home-purified alginate polymer, such as alginate acid or sodium alginate from Sigma (+W201502), and modified alginate polymers, such as methacrylate modified alginate, and combinations thereof. As used herein, "combinations thereof" refer to mixtures of the polymers as well as polymer blends. Further, in some embodiments, other polymers such as hyaluronic acids can be blended or incorporated into the alginate polymers to dope the alginate hydrogel. To form the tubes, alginate polymers are first dissolved in water or cell compatible buffer to form alginate solutions including from about 0.01% (w/v) to about 20% (w/v) alginate. In particularly suitable aspects, the tubes are then prepared and filled with cells using an extruder. Extrusion conditions will be those known in the art suitable for the particular cell survival and growth.

While described herein using alginate hydrogel tubes, it should be understood that other hydrogel materials may be suitable for use in making the tubes. For example, the hydrogel tubes could be made from materials such as polyethylene glycol, poly(vinyl alcohol), and the like, and combinations thereof.

Figure 2C:
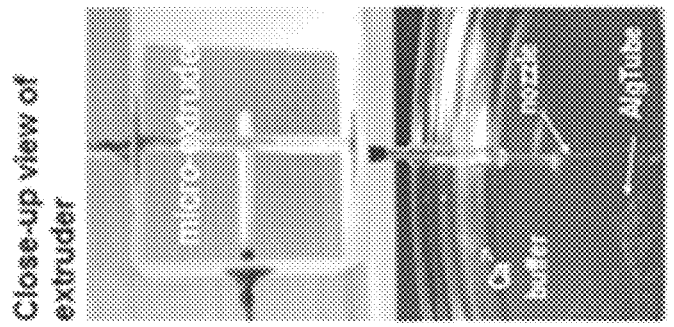
FIG. 2C is a close-up view of the extruder component of the device in FIG. 2B.
Figure 2B:
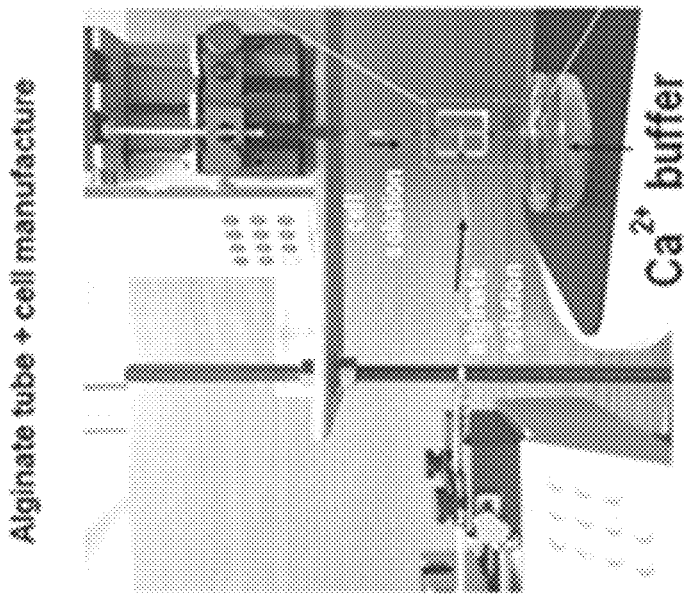
FIG. 2B depicts that laboratory set-up of an exemplary device for making hydrogel tubes.
Figure 2A:
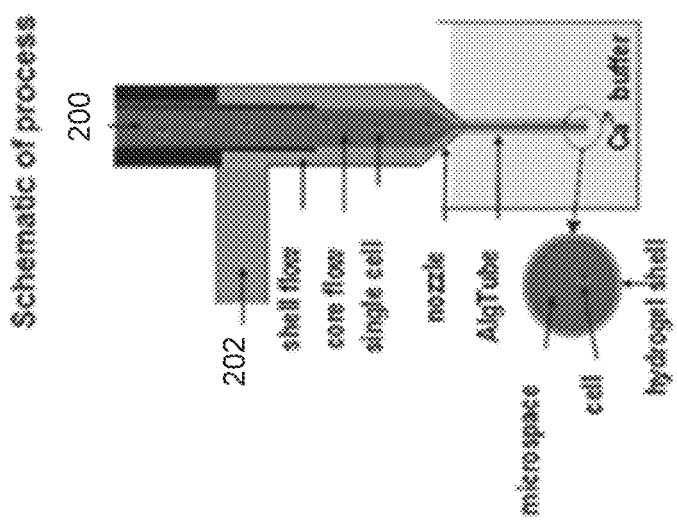
FIG. 2A depicts a schematic of an exemplary process for making hydrogel tubes.

By way of example, as shown in FIGS. 2A-2C, a cell solution including cells is supplied via a first inlet 200 and the hydrogel-forming (e.g., alginate) solutions are supplied via at least a second inlet (shown in FIG. 2A as inlets 202). Both the first stream including the cell solution and the second stream including the alginate solution are extruded into a cell compatible solution containing calcium ions or other ions or chemicals, such as barium ions, that can crosslink the alginate polymers in the alginate solution. The cell compatible solution allows the alginate polymers to instantly crosslink, thereby gelling the alginate solution and forming the tubes. Typically, the tubes are sufficiently crosslinked in a time period of typically ranging from about one minute to about 30 minutes.

Typically, as formed, the tubes will be sized for the particular cells and amount of cell expansion desired. Suitably, the tubes confine the cell masses less than the human tissue diffusion limit (e.g., typically 500 μm in radial diameter) to ensure efficient mass transport during the entire culture (FIG. 1C). Numerous research has found cell aggregates larger than 500 μm lead to impaired mass transport, cell growth, viability and phenotypes. The tubes can have a length typically ranging from millimeters to meters. Additionally, the outer and inner diameters of the hydrogel tubes can vary from micrometers to millimeters.

Figure 3A:
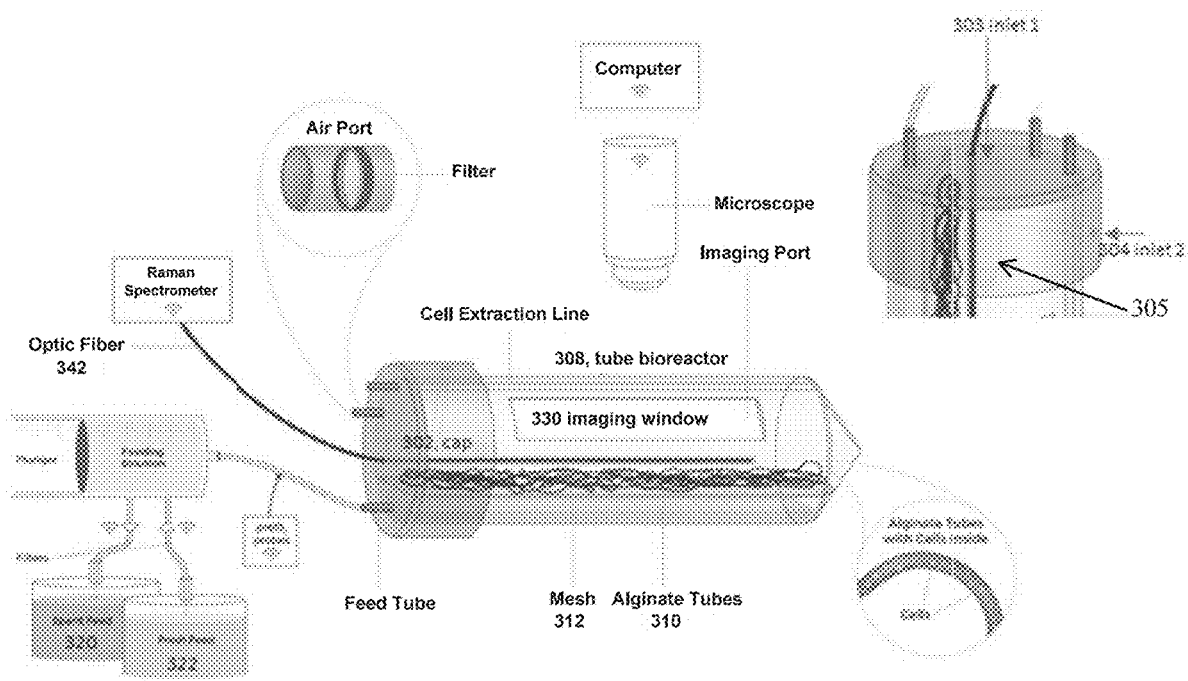
FIG. 3A depicts a cell expansion system of one embodiment of the present disclosure for use in a large-scale cell production and its components.

Once sufficiently crosslinked to form tubes, the cell compatible solution is removed and cell culture medium is added to culture the cells now within the crosslinked alginate hydrogel tubes. In some aspects, the fibers, including cells, are suspended in cell culture medium in cell culture vessels or bioreactors (an exemplary cell expansion system including a bioreactor having a tubular housing is shown in FIG. 3A, discussed below). The cell culture medium can be any medium known in the cell culture art that is suitable for supporting cell survival, growth, expansion and differentiation. Typically, the cell culture medium will include, but is not limited to, a carbon source, a nitrogen source, and growth factors. The specific cell culture medium for use in culturing the cells within the alginate hydrogel tubes will depend on the cell type to be cultured.

Cell culture conditions will vary depending on the type of cell, the amount of cell expansion, and the number of cells desired. Once sufficient cell expansion and desired numbers of cells are reached, the cells can be passaged and seeded into new alginate hydrogel tubes for a subsequent round of growth and expansion. Alternatively, the expanded cells can be differentiated into the final desired cell type within the hollow tube.

As shown in FIG. 3A, the cell expansion system 300 has several unique features. Initially, the system 300 includes a cap 302 in fluid connection with a tubular housing 308. The cap 302 of the system 300 (detailed in top right of FIG. 3) has an extruder 305 including a first inlet 303 operable for introducing a cell solution into the cap and a second inlet 304 operable for introducing a hydrogel-forming solution (e.g., an alginate solution) into the cap. The extruder 305 can be made with multiple nozzles (e.g., from 2 to thousands) to simultaneously process multiple hydrogel tubes to scale up the hydrogel tube processing. The two solutions are pumped into the extruder and the pumping rates have been calculated by computational fluid dynamics modeling and experimentation. Future users will be provided with exact pumping schedules to control tube dimensions and stability of operation. The advantage of the built-in cap is sterility.

The tubular housing 308 is initially filled with a $CaCl_2$ solution. The housing 308 includes a mesh 310 serving as a support for the alginate tubes 312. In FIG. 3A, the mesh 310 is shown in the axial configuration. This configuration is designed for operating the system in a horizontal position. In the horizontal configuration, the alginate tubes are aligned more or less in the axial direction although it is not critical to have in perfect alignment. When the system is operated vertically, the mesh is a round disc positioned about one third from the reactor base 320. The purpose of the mesh is to separate the section of the system that contains the pump inlet/outlet from the alginate tubes.

Growth medium can be added through: (1) semi-batch, where medium is pumped in and replaced when critical levels for certain growth constituents and/or metabolic waste constituents are triggered, (2) perfusion, where growth medium is continuously pumped through the bioreactor; or (3) pumped in and out of the bioreactor in a continuous cycle referred to as flood/ebb cycles by means of the reciprocating pump. This method of growth medium cycling has been specially designed to assure that conditions around the tubes remain as homogeneous as possible and is closely connected to the use of the mesh platform. The alginate tubes have neutral buoyancy (which changes slightly as cell density increases) and tubes become suspended in the growth medium during the flood stage and collapse onto the mesh during the ebb stage. The advantage of this flood/ebb approach is that the alginate tubes are exposed to more homogeneous conditions, i.e., dead pockets of fluid between tubes are eliminated and variations in bulk conditions are reduced—a prerequisite for homogeneous cell growth, but without damaging the fragile tubes. During the ebb cycle the growth medium is pumped from the bioreactor into the pump vessel, which is equipped with a pH, dO and glucose sensor. If anyone of the sensors detects a value below the set value, then the growth medium is pumped to the spent tank 320 and replaced with fresh medium 322 before the flood/ebb cycle is resumed.

Figure 4:
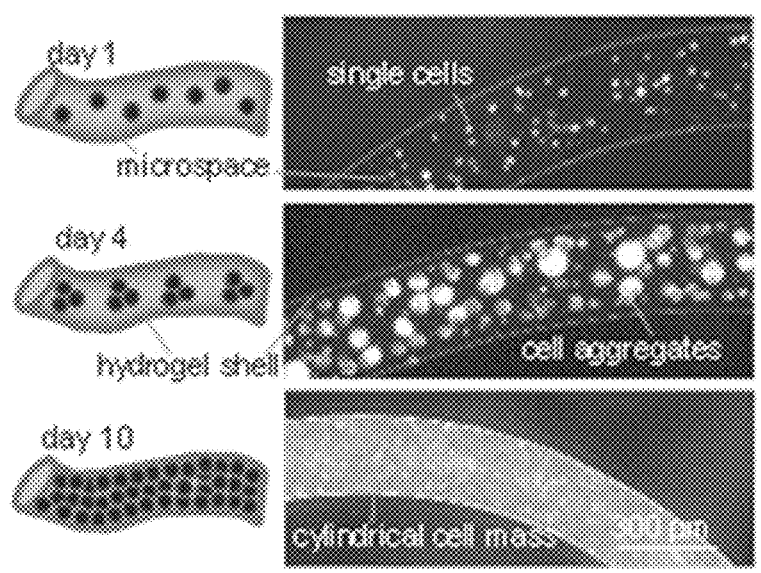
FIG. 4 depicts cells seeded in alginate hydrogel tubes. The first 24 hours, cells form small aggregates, followed by exponential cell growth over the next 9 days. Opacity increases with cell density and at day 10 the cells file the tube, approaching a cell density of $(5-10)\times 10^8$ cells/mL.
Figure 5A:
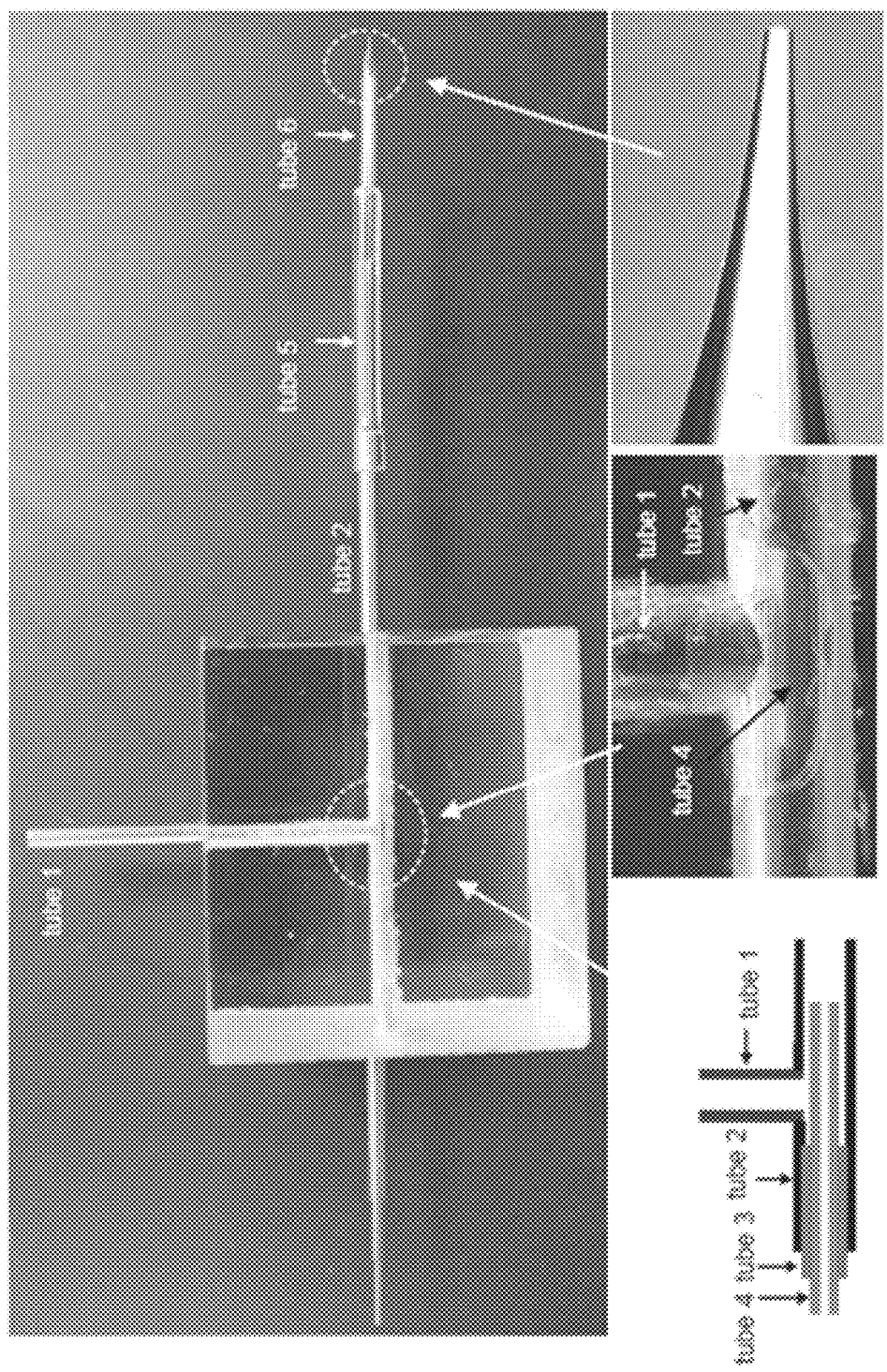
FIGS. 5A-5C depict a micro-extruder as used in the process of the present disclosure.
Figure 5B:
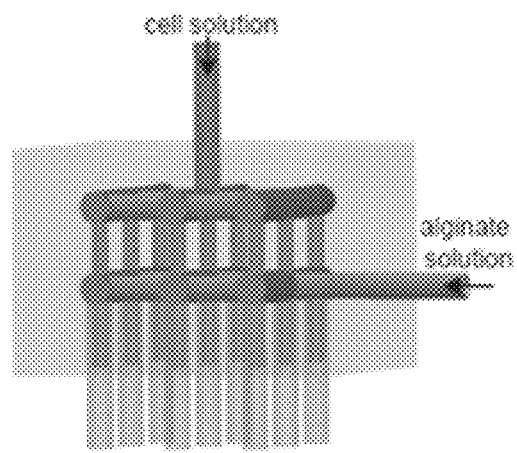
Figure 5C:
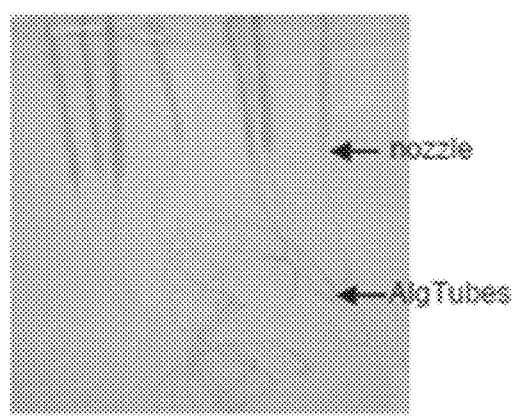

As shown in FIG. 3A, an imaging port 330 (which is merely a flat section of the wall and made of a high quality material that permits optical transparency in the visible and near infra-red range (quartz is such a material). A high resolution endoscope 332 can take images of sections of the tubes, as shown in FIG. 4 (right panel). These images are fed to a neural network (NN), which have been trained to identify cells. The NN provides a cell density. Since this assessment is based on a 2-d projection of the cell density in the tubes, a calibration curve is used to interpret the NN result in terms of cell density (cells/mL). The calibration curve is cell specific. Briefly, the curve is calculated by using experimental results to define key parameters of a cell aggregation-and-growth model. The model provides a 3-D mathematical image and a projection of that image onto a 2-D plane is matched with the endoscope image. The advantage of the AI imaging is unobtrusive, continuous real-time monitoring of cell density.

The bioreactor 300 also makes provision for a port 340 through which an optical fiber 342 can be inserted into the bioreactor to monitor the growth medium. Raman spectroscopy provides qualitative and quantitative (once calibrated) information of complex molecules like proteins and cytokines. Again, depending on the specifics of the application, Raman spectroscopy can be used to monitor cell viability, apoptosis and the secretion of specific molecules which correlate with a cell fate.

Cells are finally released from the hollow space of the tubes by dissolving the tubes chemically or physically. In one aspect, the tube is dissolved using a chemical dissolvent such as ethylenediaminetetraacetic acid (EDTA), ethylene glycol tetraacetic acid (EGTA), or an alginate lyase solution (available from Sigma-Aldrich). In another aspect, the tube is dissolved using a mechanical force. The duration of the cells within the tube can typically vary from days to months.

The cells are useful in both research laboratories and industry. Small scale and large scale of cells can be manufactured with the system for laboratorial and industrial applications, respectively. The cell expansion system of the present disclosure can be used for either scale-up (large production in a single tube) or scale-out (large number of small tubes, each one operated independently from the other). The bioreactor will have a typical volume of 50 mL for personalized expansion applications (scale out) and 1 L and more for scale-up applications.

Figure 3B:
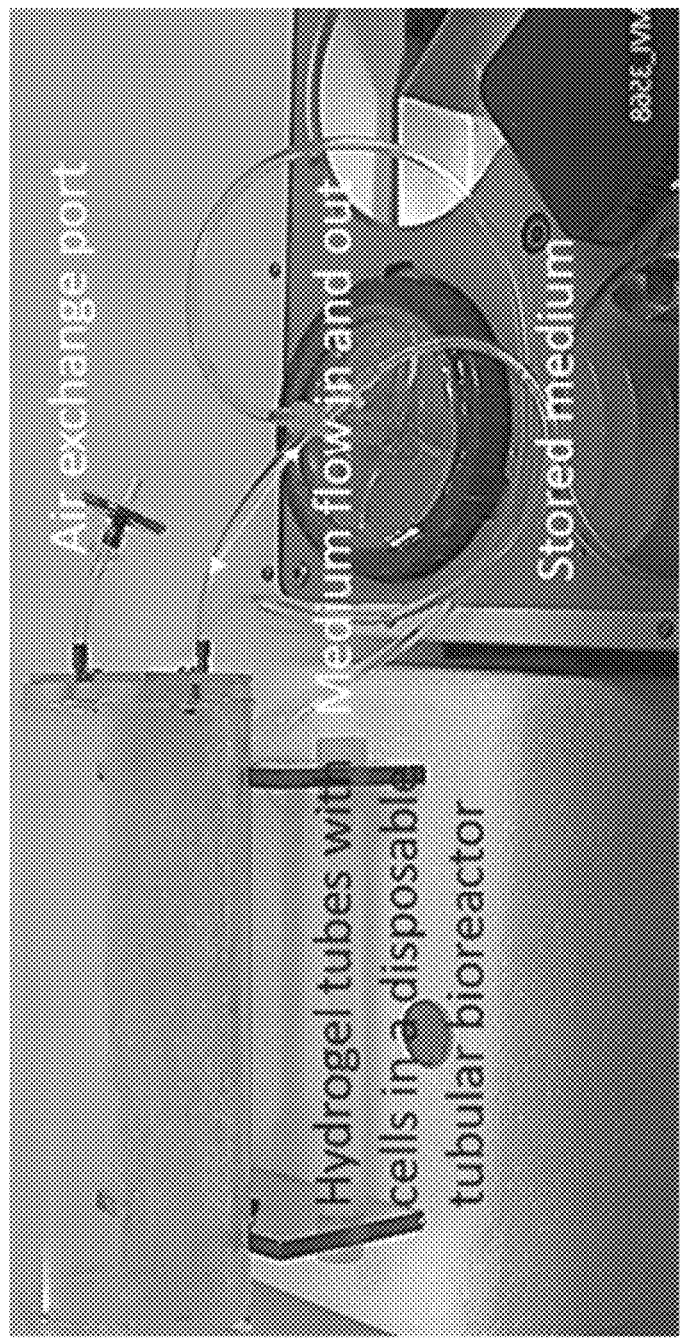
FIG. 3B depicts a cell expansion system of one embodiment of the present disclosure for use in a large-scale cell production and its components.

FIG. 3B provides an exemplary cell expansion system for scaling up cell production. The tube (about 1 liter) can contain about 200 mL of alginate hydrogel tubes to produce ~$1.0 \times 10^{11}$ cells. Medium is pumped into and out of the tubular housing of the system. Being modular, this housing can be further scaled up to produce more cells through increasing its length. The tubular housing can be vertical or horizontal. The tubular housing diameter can be adjusted based on needs.

Cells can be efficiently and effectively prepared in size and number for use in degenerative disease and injury treatment, drug screening, for expressing proteins and the like. Additionally, the cells can be used to manufacture proteins and vaccines. In yet other aspects, the cells can be used for tissue engineering.

Various functions and advantages of these and other embodiments of the present disclosure will be more fully understood from the examples shown below. The examples are intended to illustrate the benefits of the present disclosure, but do not exemplify the full scope of the disclosure.

Example 1

In this Example, primary T cells with their activators (e.g. anti-CD3/CD28/CD2 antibodies) were processed into and cultured in microscale alginate hydrogel tubes (AlgTubes) that were suspended in the cell culture medium in a culture bioreactor. Under optimized culture conditions, the AlgTubes enabled expanding T cells with high cell viability, low DNA damage, high growth rate (~320-fold expansion over 14 days), high purity (~98% CD3+) and high yield (~3.2× 108 cells/mL), all offering considerable advantages over current approaches. Moreover, the expanded T cells secreted high levels of T cell cytokines, indicating their normal functions. This system can significantly reduce the manufacturing cost and increase the production capability of T cells to advance the adoptive immunotherapy.

Materials and Methods

Cell culture: CD3+ T cells were obtained from Astarte Biologics (donor #1, cat #1017-3503MA17; donor #2, cat #1017-3535AP17; donor #3, cat #1057-3325SE16). CD3+ T cells were grown in ImmunoCult™-XF T cell expansion medium (cat #10981, StemCell Technologies) with anti-CD3/CD28/CD2 activators (cat #10970, StemCell Technologies) in the presence of 100 IU/ml IL-2. For dynamic 3D culture, the culturing was rocked at 15 rocks/min (rpm). For static and dynamic 3D culturing, the cell aggregates were dissociated by gently pipetting and split into multiple wells at a density of $1.0 \times 10^6$ cells/mL on day 3, 6, 9, and 12. Cells were cultured in an incubator with 5% $CO_2$, 21% $O_2$ at 37° C.

Culturing T cells in AlgTubes: For a typical cell culture, 40 μL of cell solution in alginate hydrogel tubes were suspended in 3 mL ImmunoCult™-XF T cell expansion medium in a 6-well plate and cultured in an incubator with 5% $CO_2$, 21% $O_2$ at 37° C. To passage cells, medium was removed and alginate hydrogel tubes were dissolved with 0.5 mM EDTA for 5 minutes. T cells were collected by centrifuging at 300 g for 5 minutes, and dissociated into single cells by gently pipetting for the next passaging or analysis.

Cell death and cell cycle analysis: The T cells culture medium was collected for measuring dead cells on day 3, 6, 9, 12 and 14, respectively. Adenylate kinases (AKs) are ubiquitous proteins present in all eukaryotic and prokaryotic cells. They are rapidly released into the culture medium upon damage of the plasma membrane of cells. AKs in the cell culture medium were quantified with the bioluminescence cytotoxicity assay kit (cat #JM-K312-500, MBL medical & biological laboratories) according to the product instruction, and normalized with a standard curve to calculate the dead cells in the culture. Samples on day 6 were harvested and live cells were counted with trypan blue. Single cells were fixed with 70% cold ethanol for cell cycle analysis with propidium iodide staining using flow cytometry.

Flow cytometry: T cells were collected and dissociated into single cells and fixed. Cells were stained with the following antibodies (all from Biolegend), PE anti-human CD3 (cat #317308), FITC anti-human CD4 (cat #317408), APC anti-human CD8 (cat #300912), and analyzed with a flow cytometer (Cytek, BD).

Comet assay: Comet assay were performed with the COMETASSAY® 2 well ES Unit w/Starter kit (cat #4250-050-ESK-PS1, Trevigen) according to the product instructions. In brief, single cells ($1.0 \times 10^5$/ml) were mixed with molten LMAgarose (at 37° C.) at a ratio of 1:10 (v/v) and immediately transferred (50 pl) onto a CometSlide, which was then placed at 4° C. in the dark for 10 minutes to form a thin layer of agarose hydrogel with cells embedded. The slide was immersed in the Lysis Solution (cat #4250-050-01) overnight at 4° C. to lyse the cells. The slide was then immersed in freshly prepared Alkaline Unwinding Solution containing 200 mM NaOH and 1 mM EDTA (pH>13) for 1 hour at 4° C. in the dark. Electrophoresis was then carried out at 21 volts for 30 minutes in Alkaline Electrophoresis Solution containing 200 mM NaOH and 1 mM EDTA (pH>13). The slide was gently immersed twice in $dH_2O$ with 5 minutes each, then in 70% ethanol for 5 minutes. The slide was then stained with SYBR® Gold for 30 minutes at room temperature. The slides were imaged with a fluorescence microscopy (SYBR® Gold maximum excitation/emission is 496 nm/522 nm). The Comet Analysis Software (cat #4260-000-CS) was used to evaluate 138 comets per sample.

Cytokines analysis: Quantibody Human Cytokine Array 1 (QAH-CYT-1-1, RayBiotech) was used to quantify the cytokine secretion in the culture medium according to manufacturer's instruction. The results were analyzed using the RayBiotech Q Analyzer program. In brief, the array chips were blocked with blocking buffer for 30 minutes at room temperature. 100 pl cell culture medium was placed into each well and incubated overnight at 4° C. After extensive washing, the biotin labeled detection antibody was added for 2 hours at room temperature. Cy3 equivalent dye-conjugated streptavidin was then added for 1 hour at room temperature. The array was scanned and analyzed by RayBiotech.

Statistical analysis: The data are presented as the mean±SD. An unpaired t-test was used to compare two groups and one-way ANOVA used to compare more than two groups. $P<0.05$ was considered statistically significant.

Results

The AlgTubes T Cell Culturing System

Figure 1D:
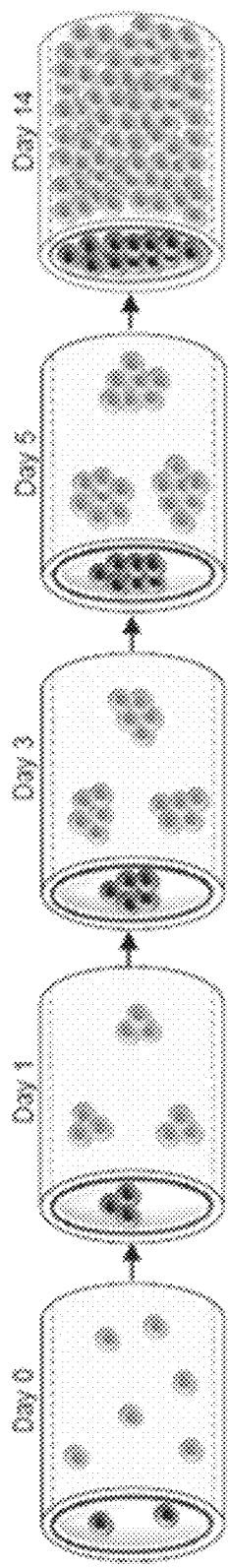
Figure 1E:
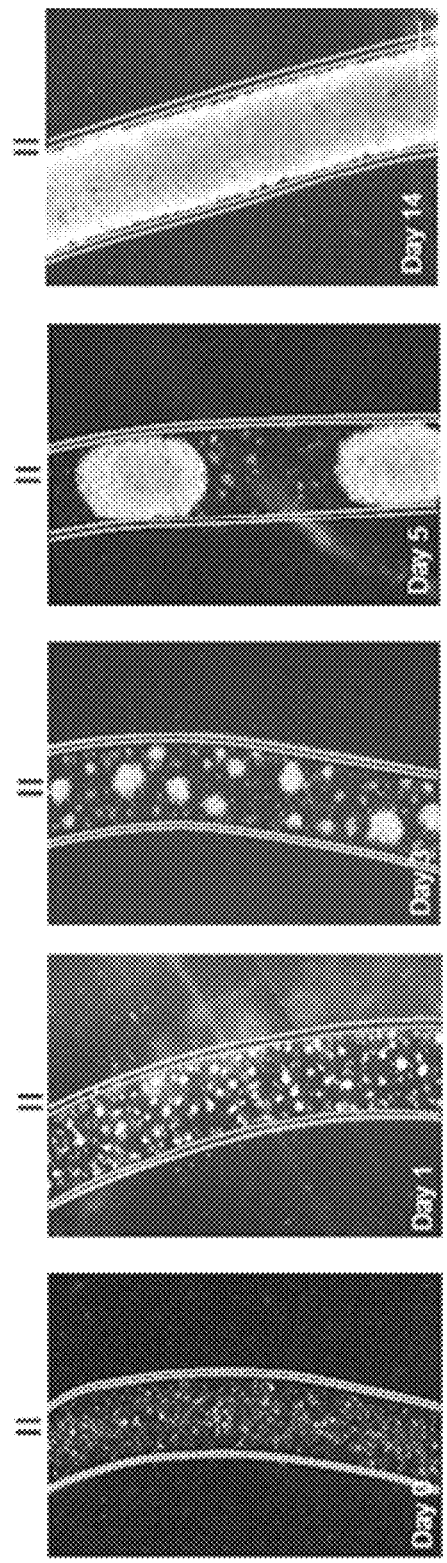
Figure 1F:
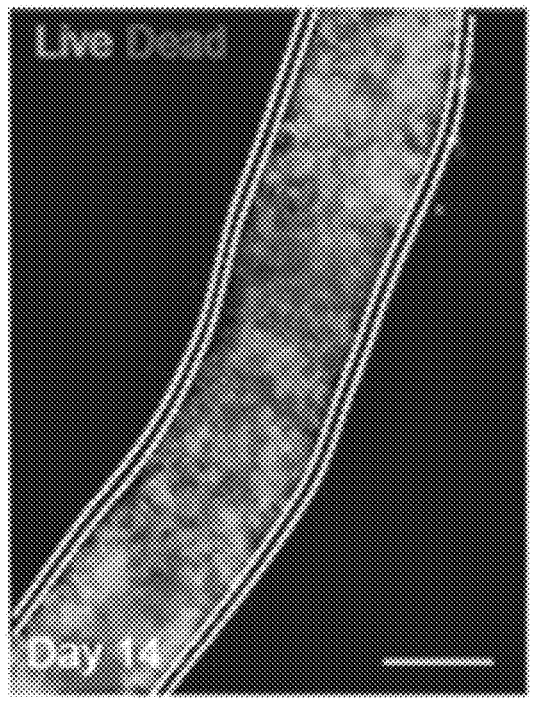
FIG. 1F depicts live dead cell staining show very few dead T cells in AlgTubes. Scale bar: 200 pm.
Figure 1G:
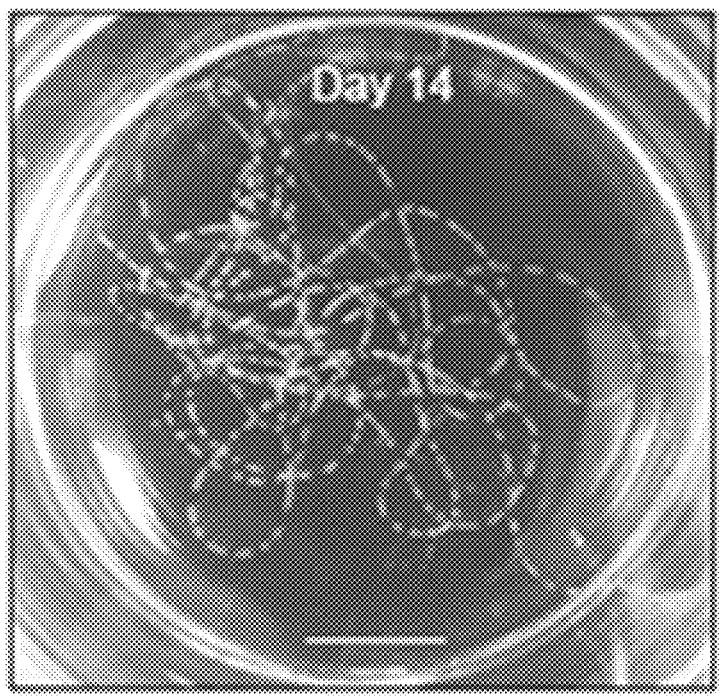
FIG. 1G is a photograph of the white cell masses in one AlgTube in a 6-well plate. Scale bar: 1 cm.

A micro-extruder was designed and made for processing AlgTubes (FIGS. 1A-1B and FIGS. 5A-5C). To process the AlgTubes, a solution containing single T cells, T cell activators (e.g. anti-CD3/CD28/CD2 antibodies) and 2% hyaluronic acid polymer, and a solution containing 1.5% alginate polymer was pumped into the central channel and side channel of the micro-extruder, respectively, to form a coaxial core-shell flow that was extruded into a $CaCl_2$ buffer. The shell alginate flow was instantly crosslinked by $Ca^{2+}$ ions to form an alginate hydrogel tube (FIGS. 1A-1C). Subsequently, the $CaCl_2$ buffer was replaced by the T cell culture medium and cells were grown in the tubes. The cell solution and alginate solution should have close viscosity to process defect-free AlgTubes. Both hyaluronic acid (HA) and methylcellulose (MC) solutions could be used to suspend cells for this purpose. In the AlgTubes, single T cells first associated to form small cell clusters that subsequently grew and filled the tubes (FIGS. 1D, 1E & 1G). T cells in AlgTubes had very high viability during the entire culture as shown by the undetectable dead cells through live/dead staining (FIG. 1F). To collect or passage cells, the AlgTubes could be dissolved with the cell-compatible ethylenediaminetetraacetic acid (EDTA) solution (0.5 mM, 5 minutes at room temperature) to release the micro cell masses that could be dissociated into single cells by gently mechanical pipetting for the following analysis or passage.

Screening Culturing Medium and Activators for T Cells Expansion

Figure 6A:
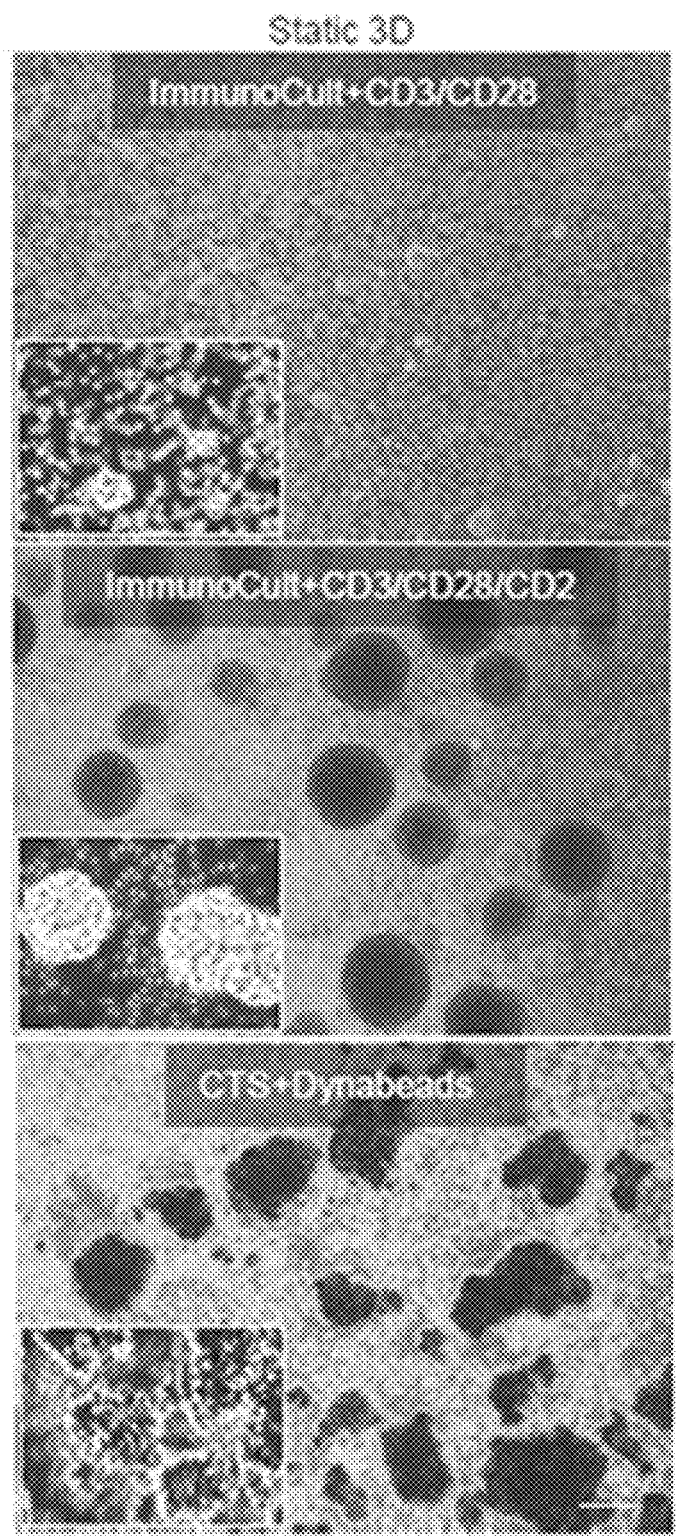
FIGS. 6A-6D depict screening culture medium and activators for T cell expansion.
Figure 6B:
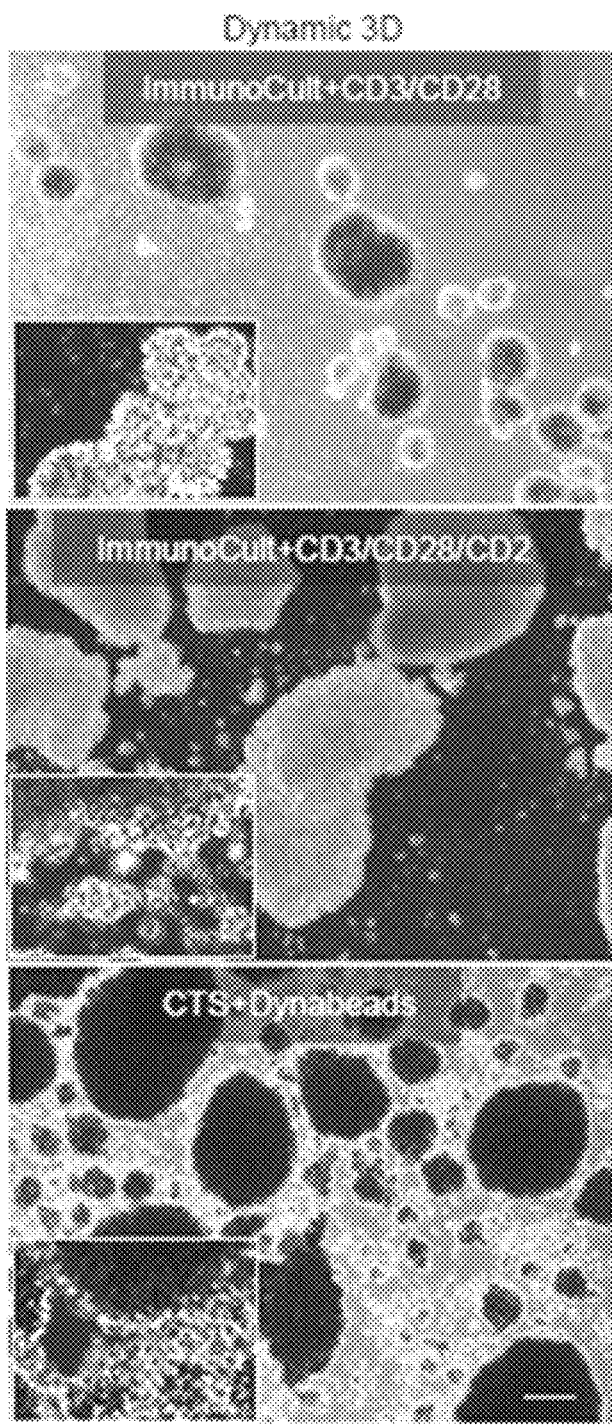
Figure 6C:
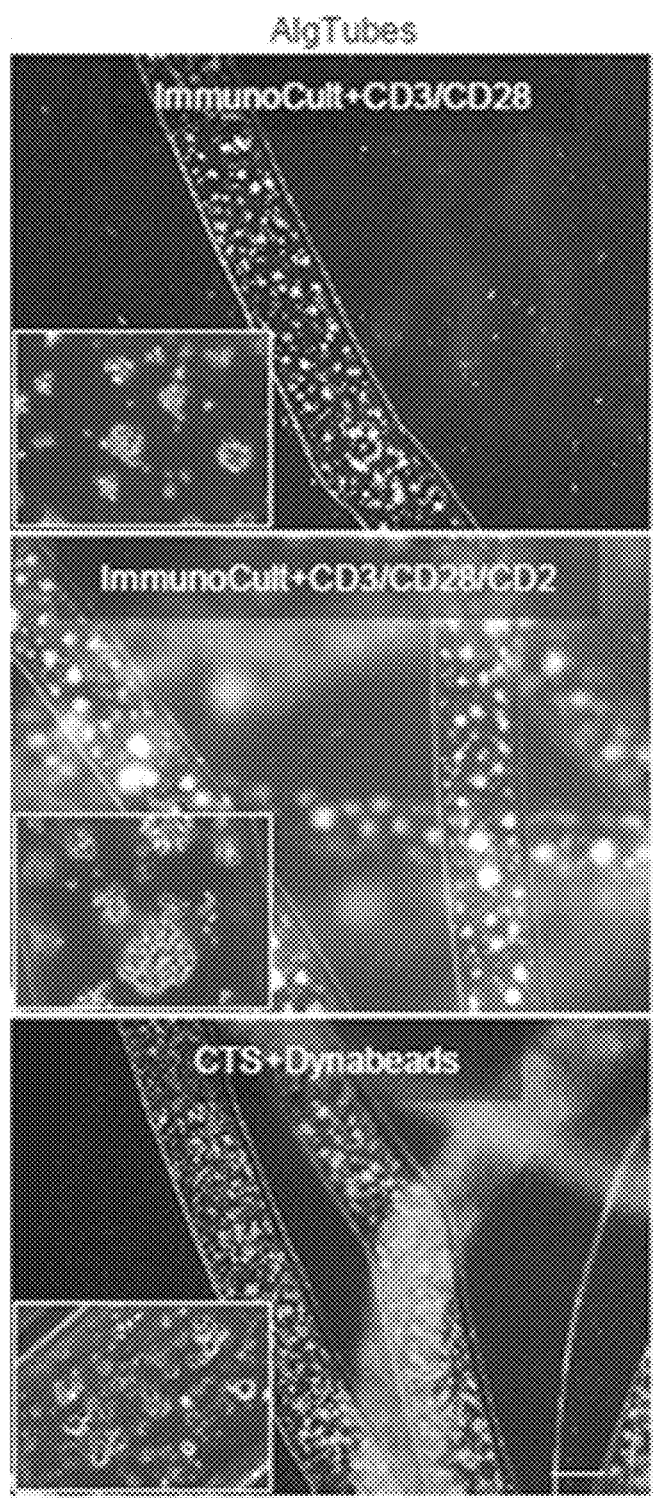
Figure 6D:
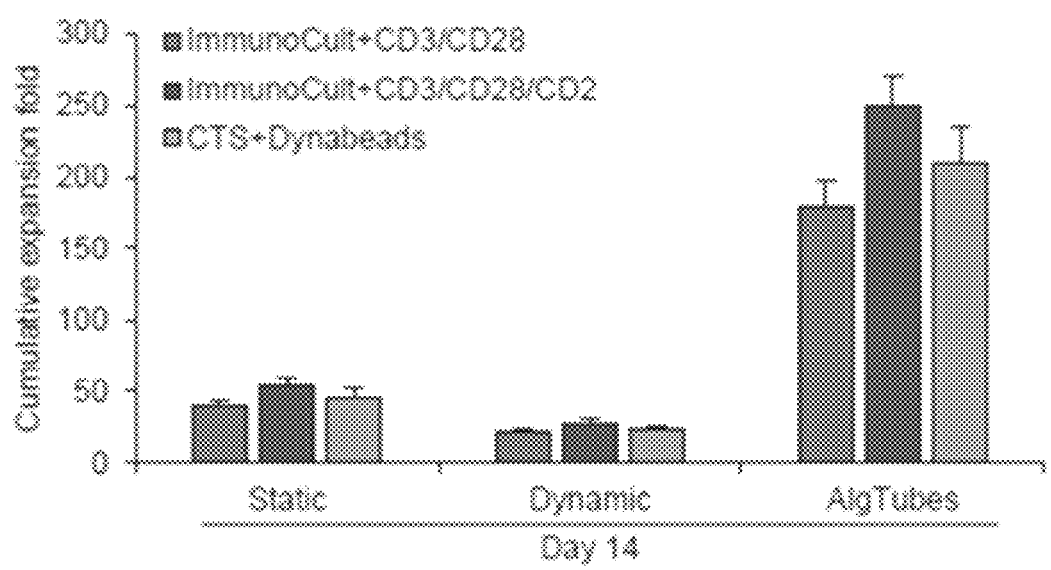

A few culturing medium and activators have been successfully used to expand T cells in the literature. These include the combination of using magnetic nanoparticles coated with anti-CD3/CD28 antibodies (Dynabeads CD3/CD28, Invitrogen) as activators and CTS™ OpTmizer™ T Cell Expansion SFM medium (Invitrogen) as the culture medium, or the tetrameric anti-CD3/CD28 antibodies or tetrameric anti-CD3/CD28/CD2 antibodies (Stem Cell Technology) as activators and ImmunoCult™-XF T Cell Expansion medium (Stem Cell Technology) as the culture medium. Initially, these medium and activators were directed compared in order to find out the best combination for culturing T cells (FIGS. 6A-6D). These cells were also cultured in static three dimensional (3D) suspension culturing (i.e. static 3D, in which cells were suspended in culture medium without agitation) and dynamic 3D suspension (i.e. dynamic 3D, in which cells were suspended in culture medium with gentle rocking) for comparison. The latter two culturing methods were used to mimic the G-Rex bioreactor and WAVE bioreactor or the CliniMACS Prodigy culture system, respectively. T cells were seeded at $1.0 \times 10^6$ cells/mL for all three methods and cultured for 14 days. For static 3D culturing, T cells grew as single cells or small clusters (e.g. less than 50 pm in diameter) with ImmunoCult medium and anti-CD3/CD28 activators. Both single T cells and spherical cell aggregates with diameters between 100 to 500 pm were found with ImmunoCult medium and anti-CD3/CD28/CD2 activators. With CTS™ OpTmizer™ medium and Dynabeads CD3/CD28 activators, T cells grew as both single cells and large non-spherical aggregates (FIG. 6A). For dynamic 3D culturing, T cells grew as aggregates under all the three culturing conditions. Additionally, these aggregates were much larger than these in static 3D culturing (FIG. 6B). In AlgTubes, T cells first formed small clusters (e.g. within the first 24 hours) that subsequently grew and filled the tubes (FIG. 6C). On day 14, T cells expanded ~55, ~28, ~250 folds in static 3D, dynamic 3D and AlgTubes. There was no significant difference between different culture medium and activators (FIG. 6D) ImmunoCult and anti-CD3/CD28/CD2 activators were used for the rest of this Example.

Adjusting Tube Diameter and Hydrogel Shell Thickness

Figure 7A:
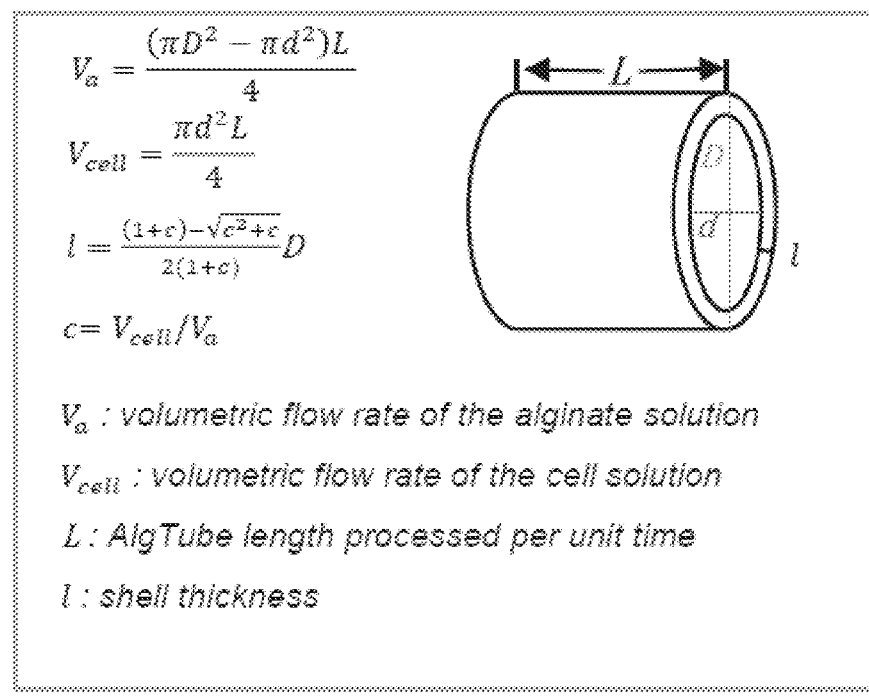
FIGS. 7A-7F depict processing AlgTubes with different hydrogel shell thickness or diameter.
Figure 7B:
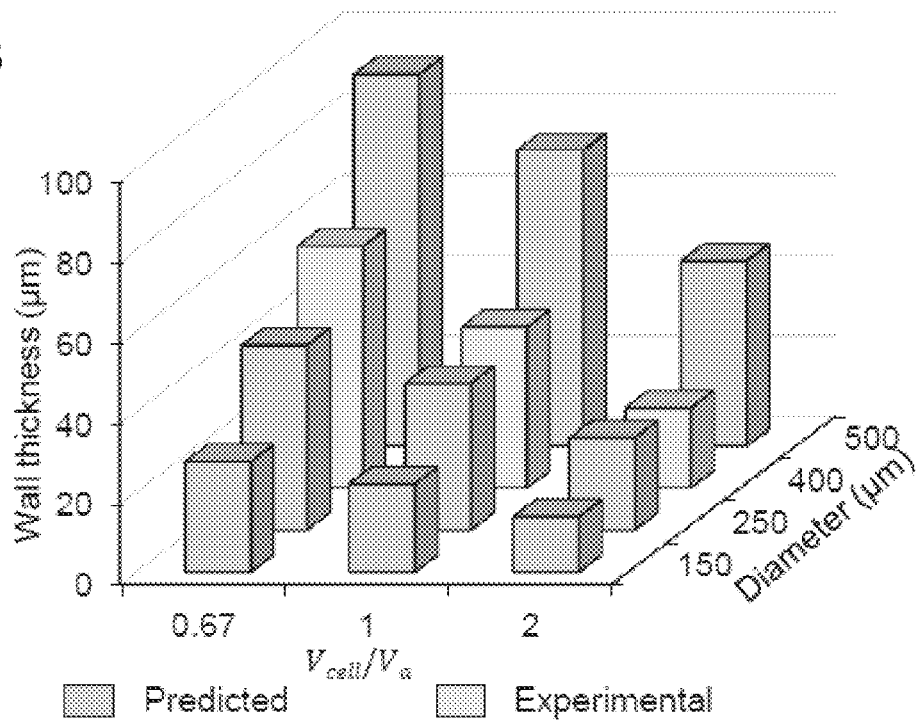
Figure 7C:
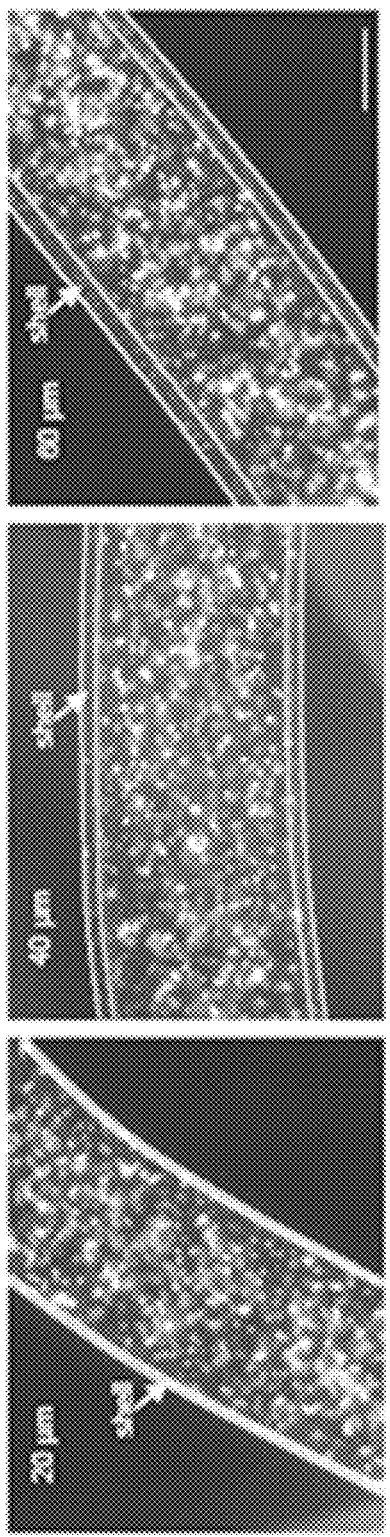
Figure 7D:
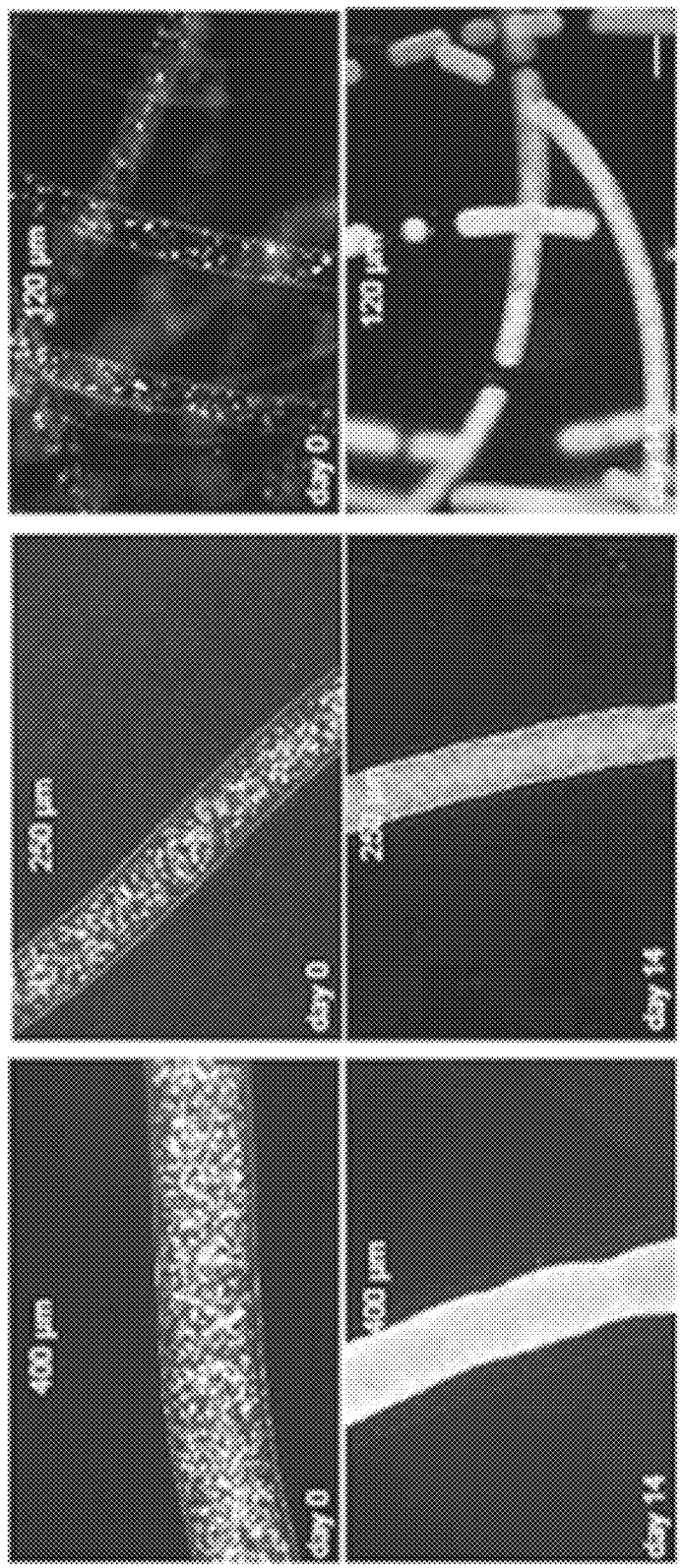
Figure 7E:
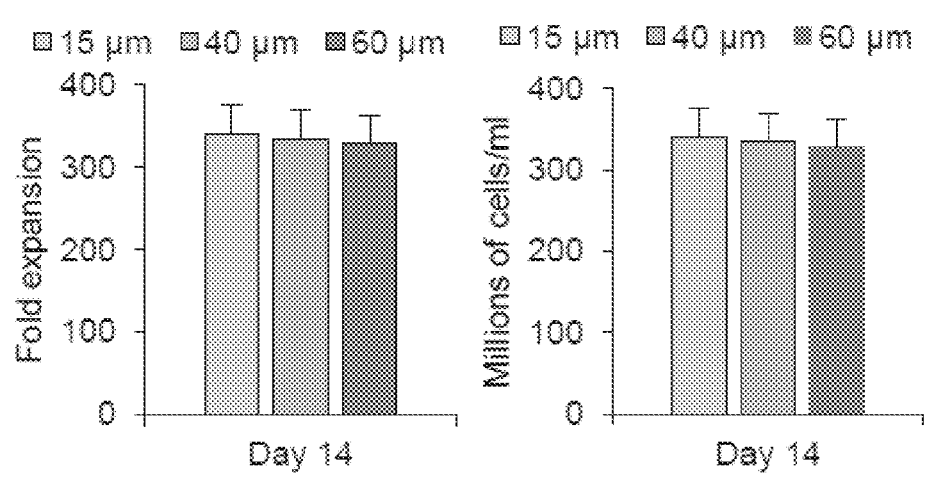
Figure 7F:
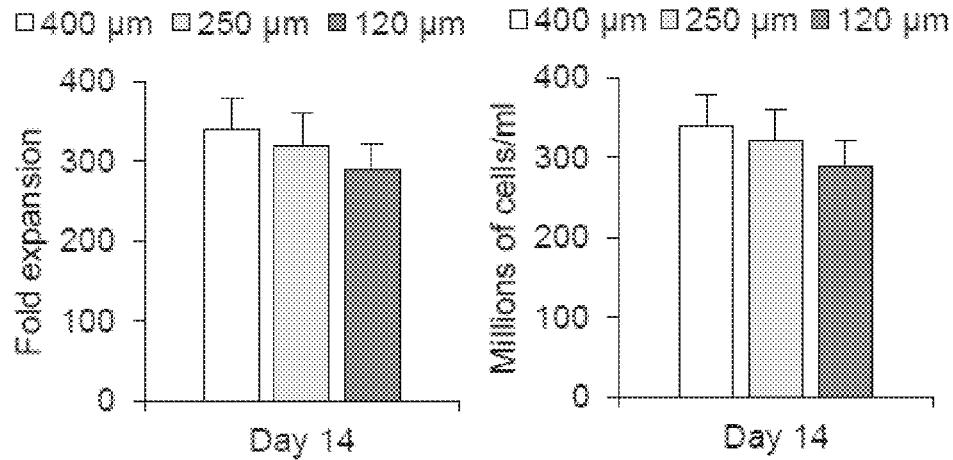

The AlgTubes' diameter and hydrogel shell thickness could be precisely controlled through adjusting the nozzle diameter of the micro-extruder, the flow rates of the cell solution and alginate solution (FIGS. 7A & 7B). The relationship between the tube' inner and outer diameter, shell thickness, volumetric flow rate of the cell solution and alginate solution, and the length of tube processed per unit time can be described with the equations shown in FIG. 7A. The tube's outer diameter and the extruder nozzle's inner diameter was roughly equal. T cells were shown to have similar morphologies, viability, growth rate and yield in tubes with shell thickness of 60, 40 and 20 µm or tubes with diameter of 400 µm, 250 µm and 120 µm (FIGS. 7C-7F). It was concluded that AlgTubes with shell thickness ≤60 µm and outer diameter ≤400 µm were appropriate for T cell expansion.

Minimal Inter-Donor Variations in Expanding T Cells in AlgTubes

Figure 8A:
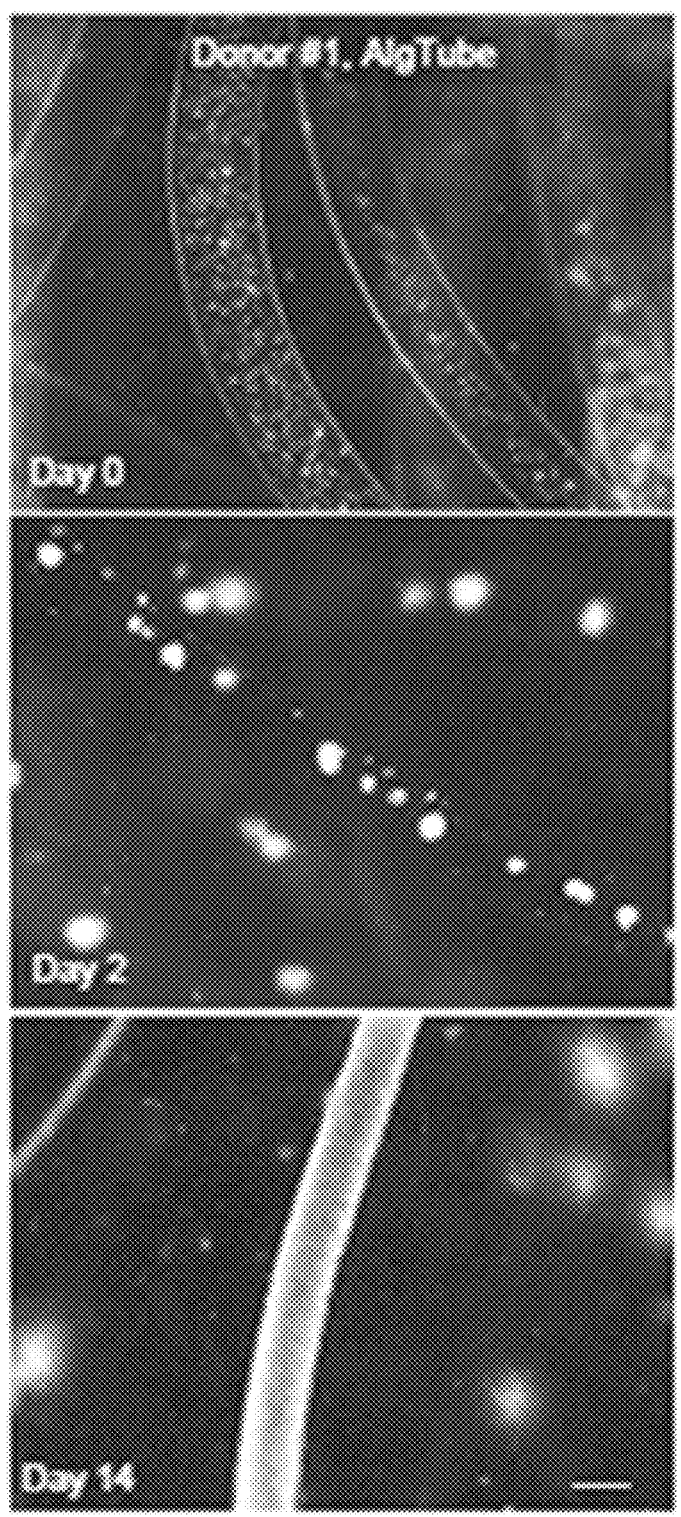
FIGS. 8A-8H depict culturing T cells from different donors (#1, #2 and #3) in AlgTubes, static 3D and dynamic 3D suspension culturing.
Figure 8B:
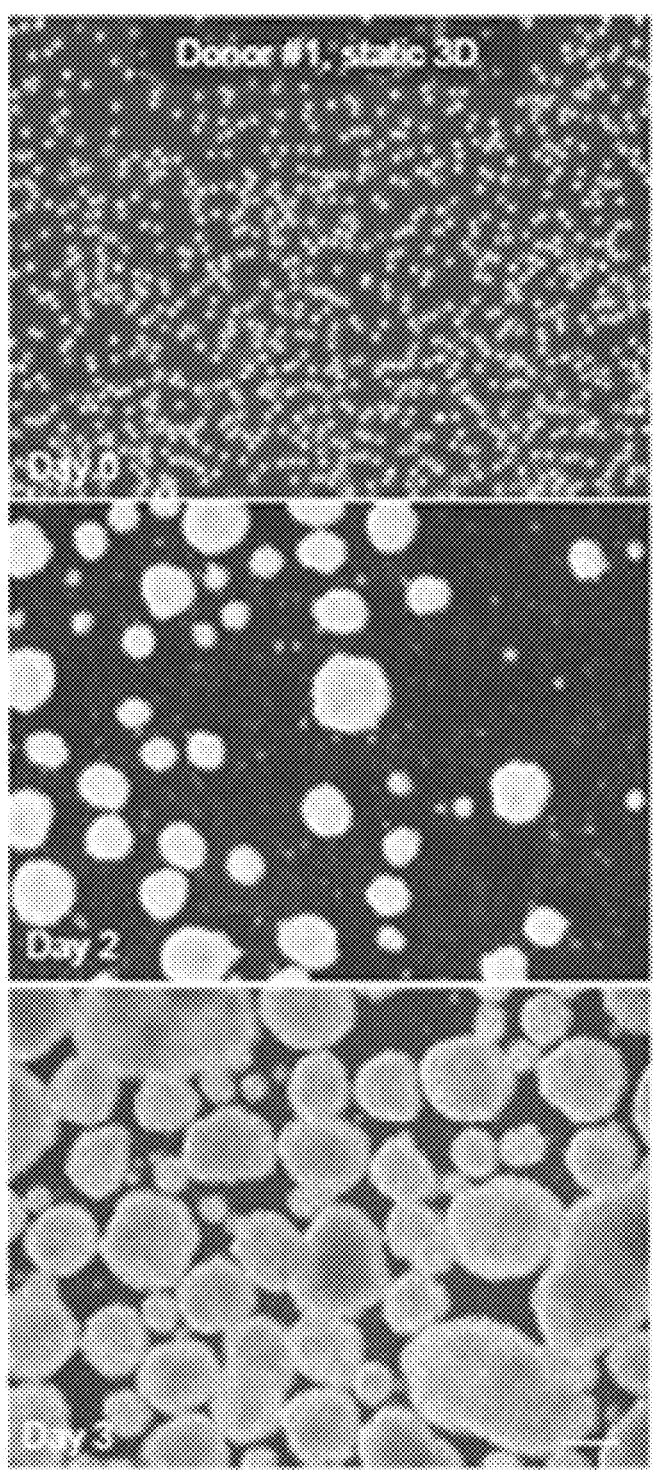
Figure 8C:
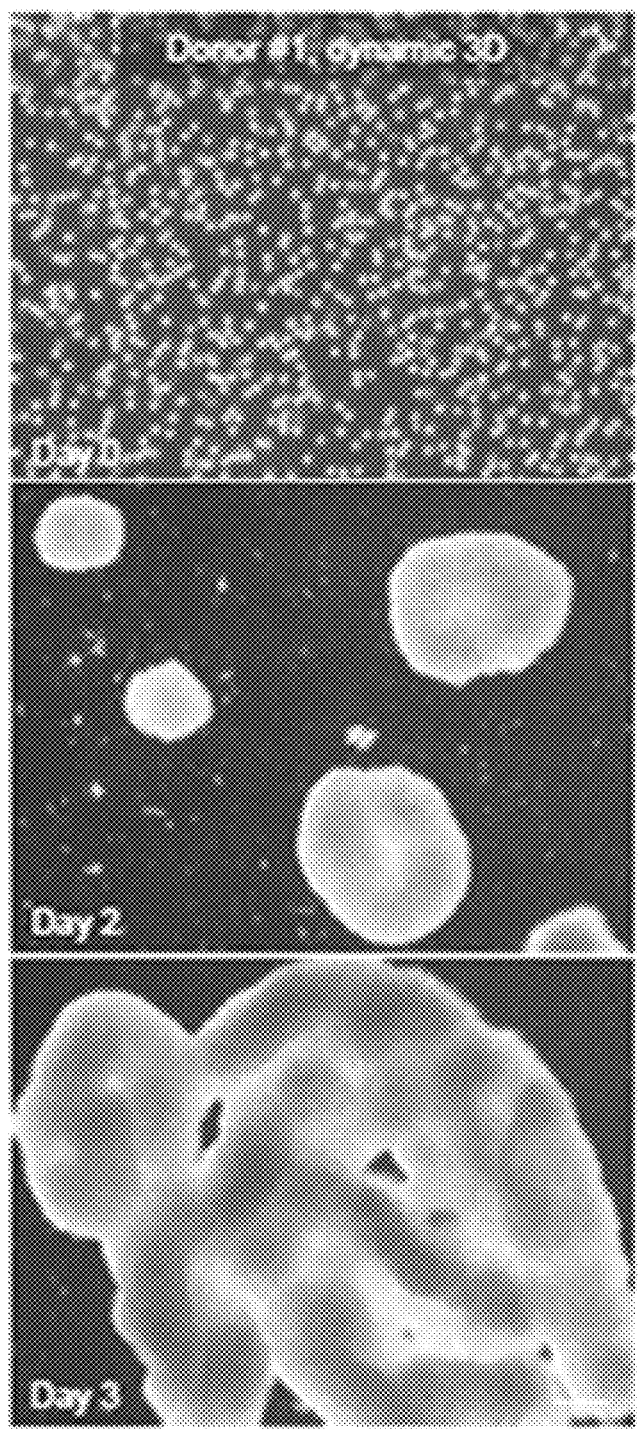
Figure 8D:
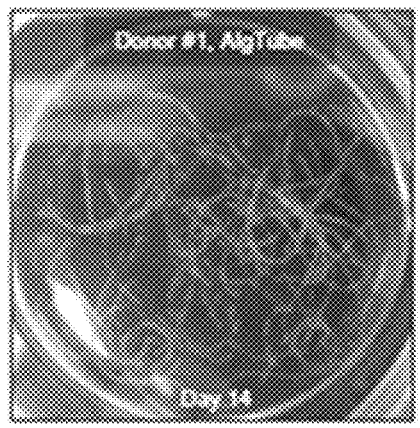
Figure 8E:
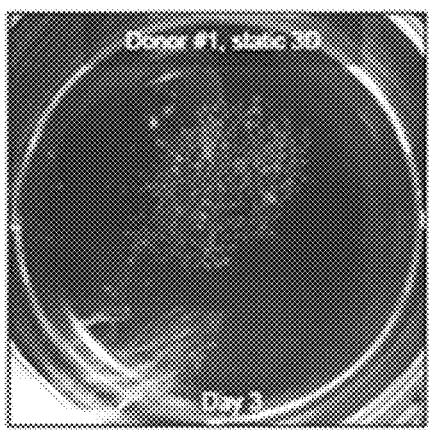
Figure 8F:
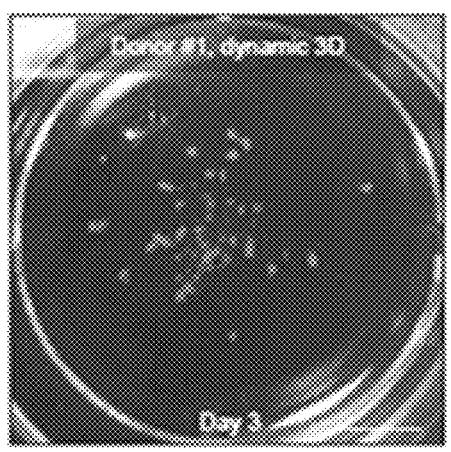
Figure 8G:
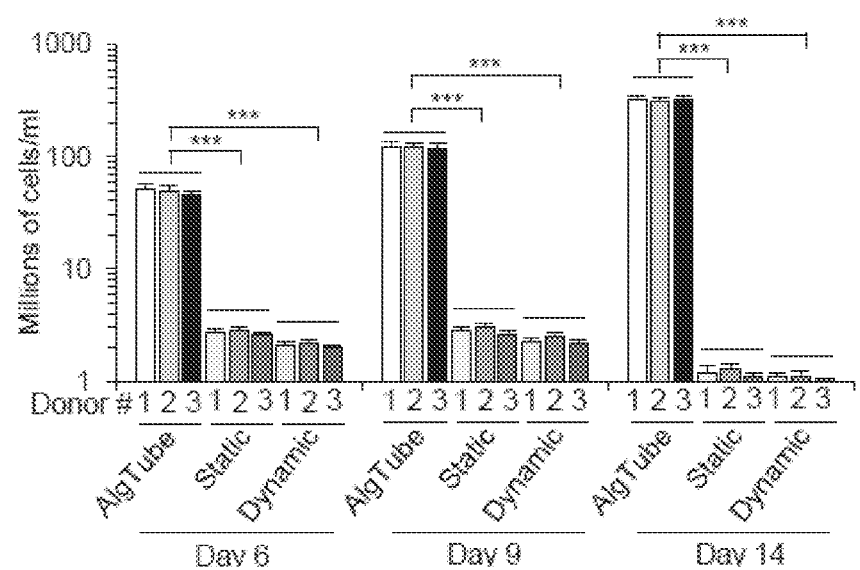
Figure 8H:
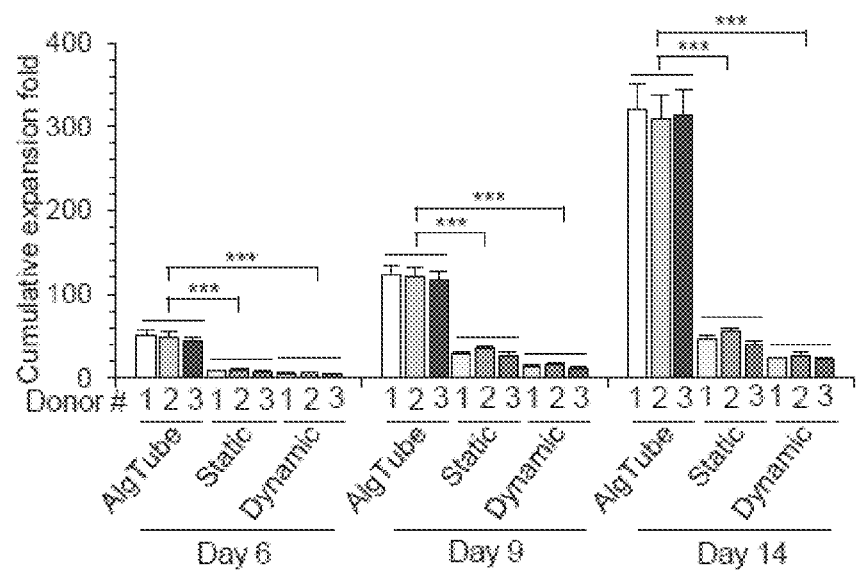
Figure 9A:
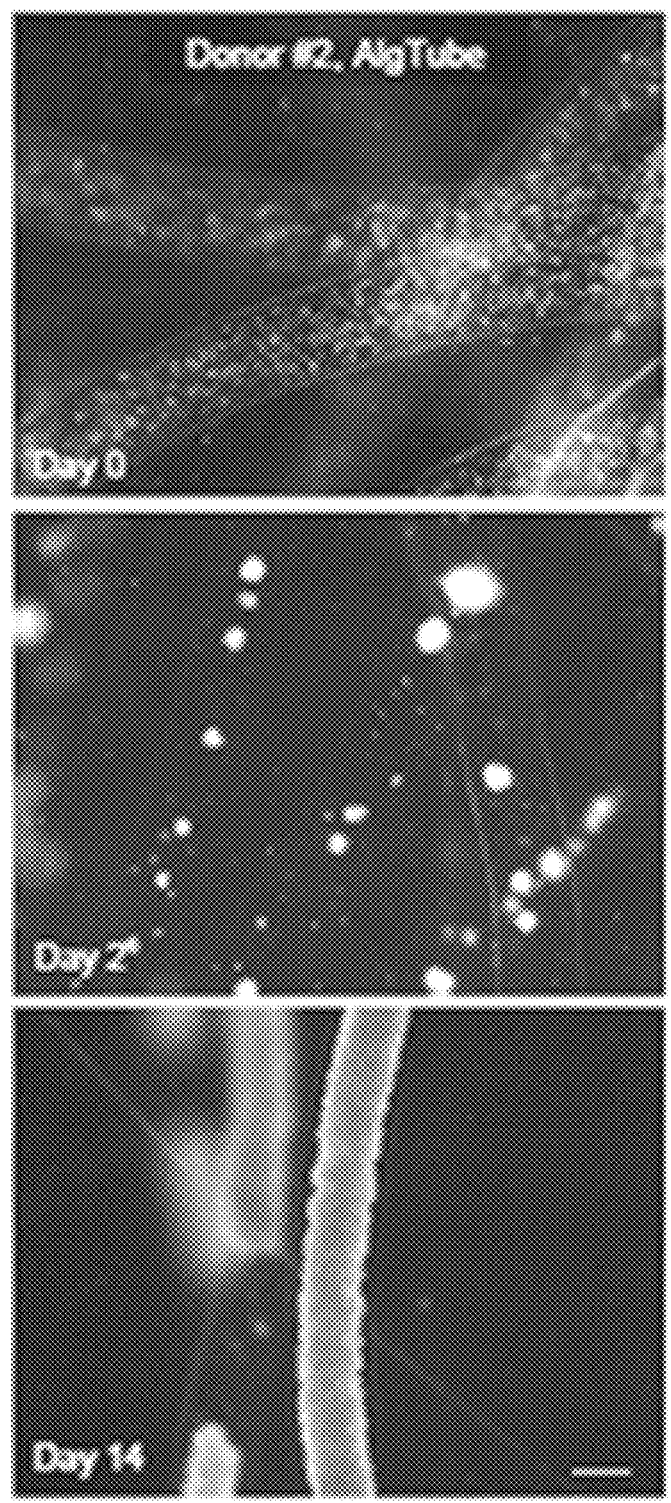
FIGS. 9A-9F depict culturing T cells from donor #2 in AlgTubes, static 3D and dynamic 3D suspension culturing.
Figure 9B:
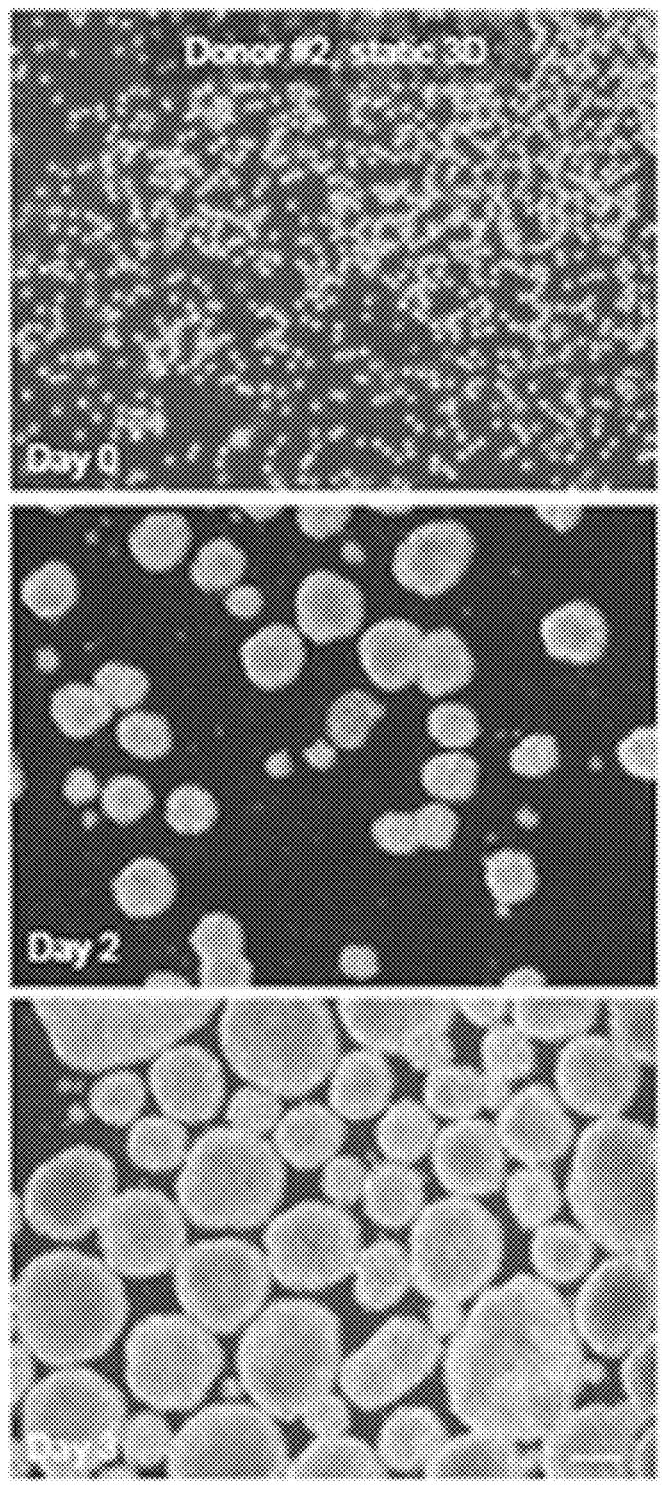
Figure 9C:
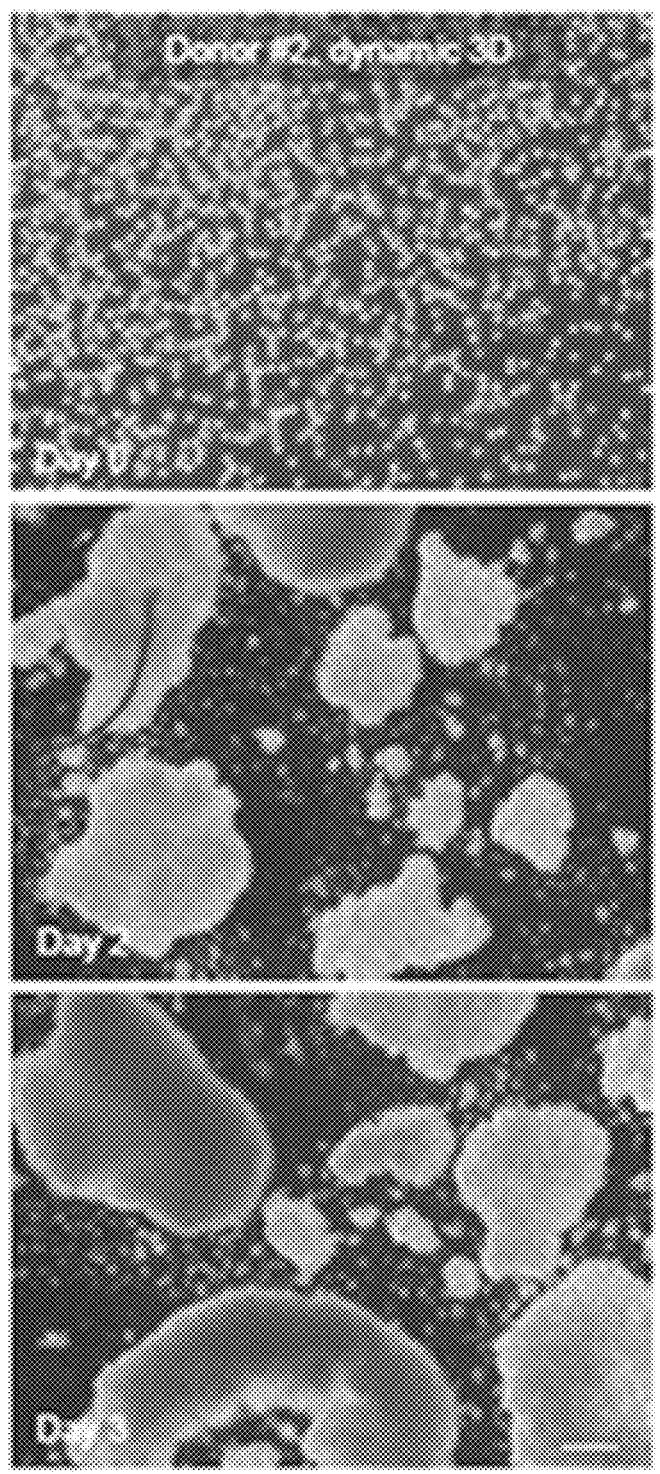
Figure 9D:
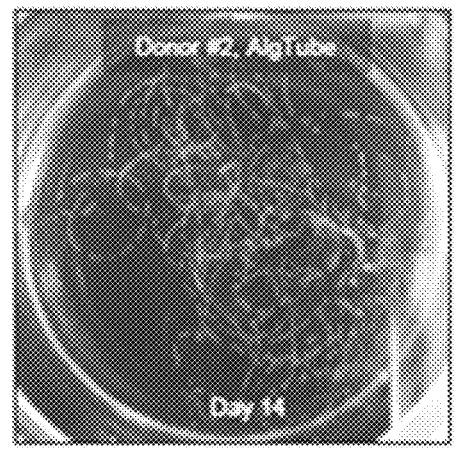
Figure 9E:
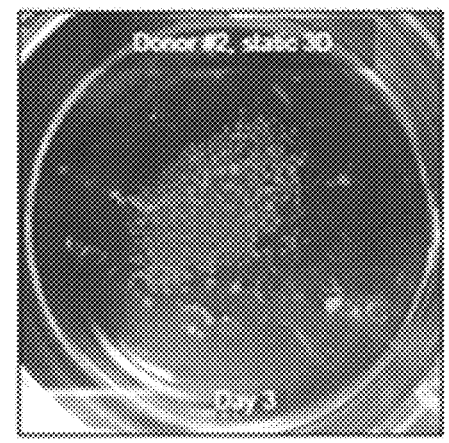
Figure 9F:
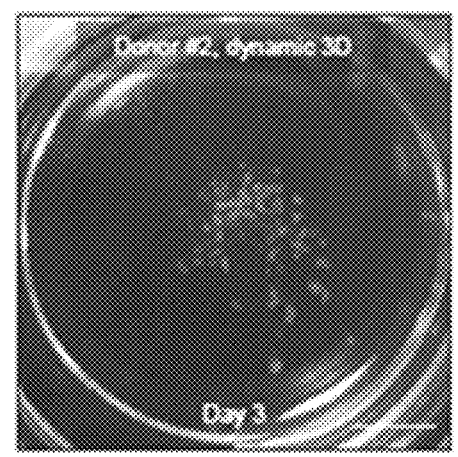
Figure 10A:
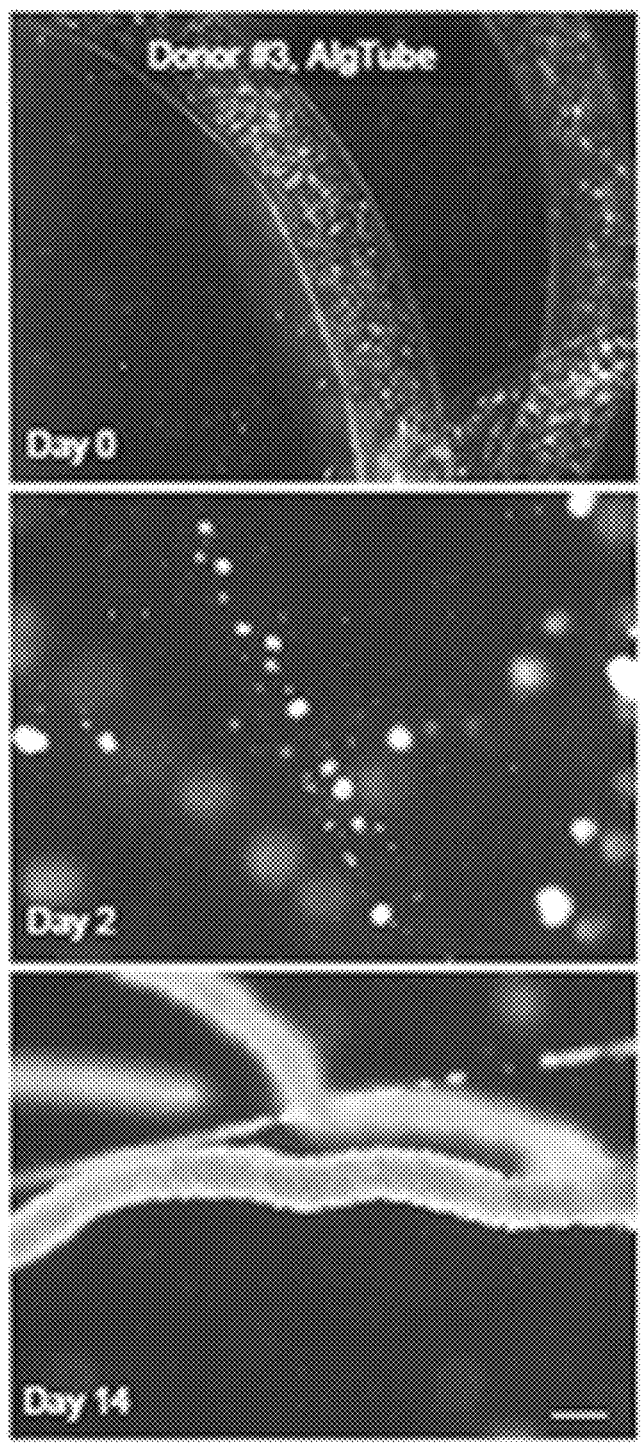
FIGS. 10A-10F depict culturing T cells from donor #3 in AlgTubes, static 3D and dynamic 3D suspension culturing.
Figure 10B:
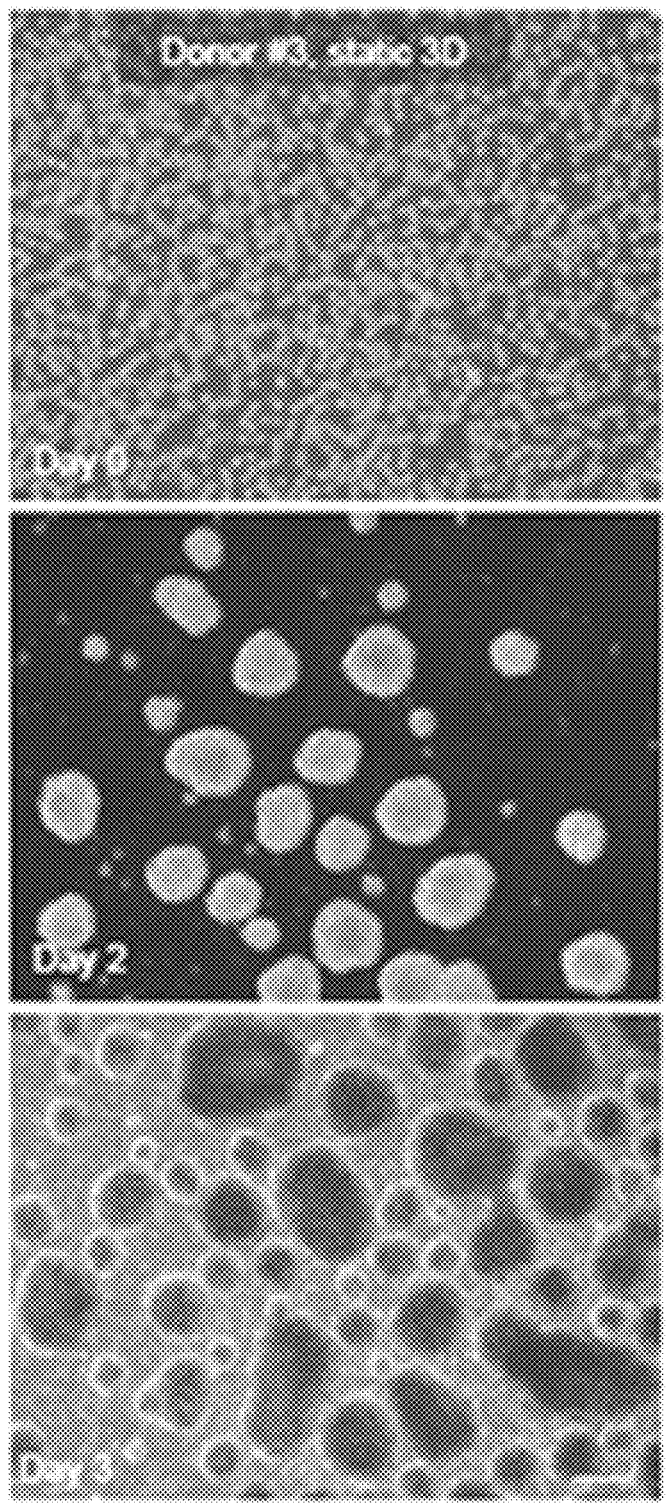
Figure 10C:
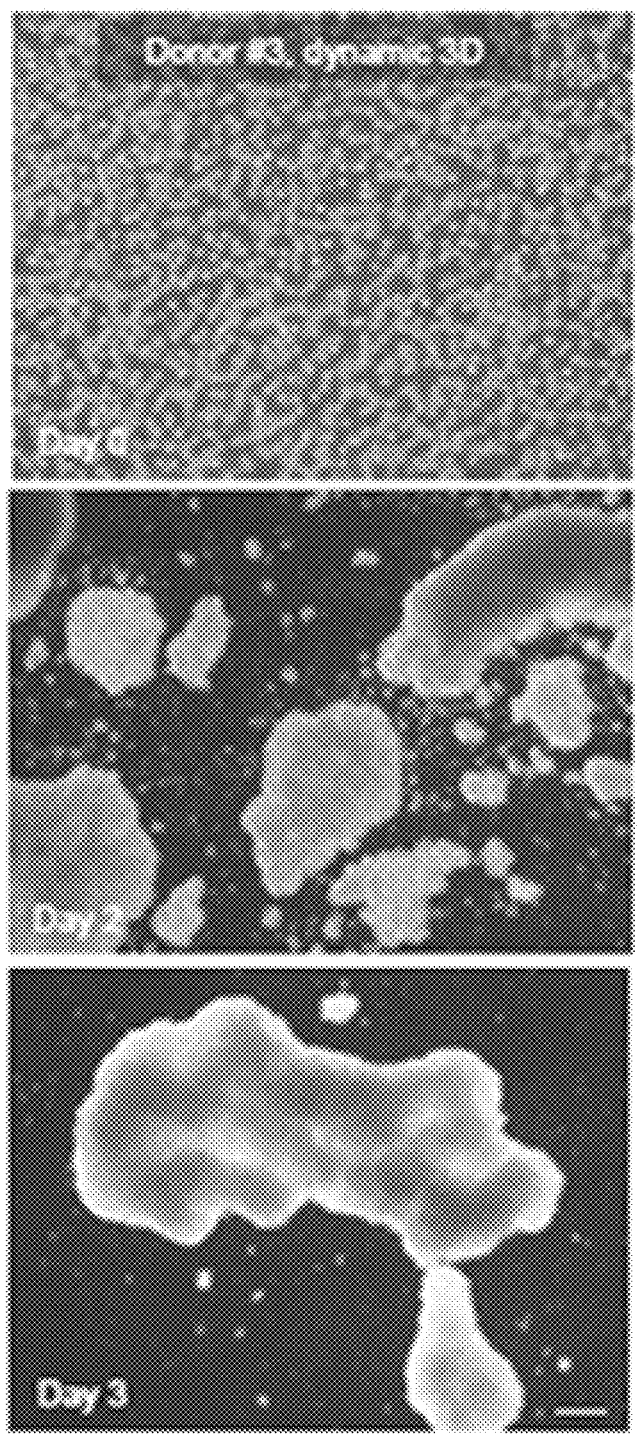
Figure 10D:
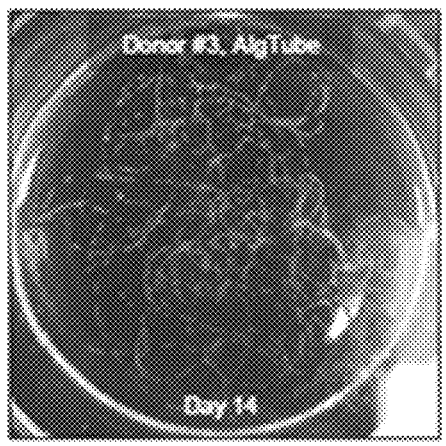
Figure 10E:
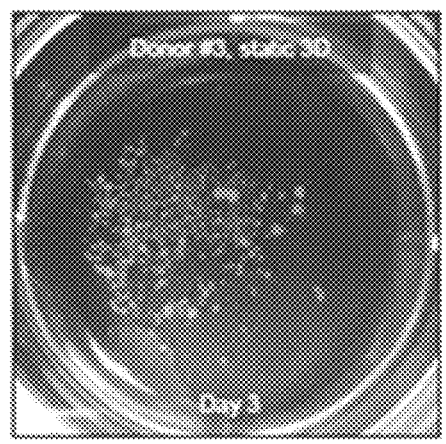
Figure 10F:
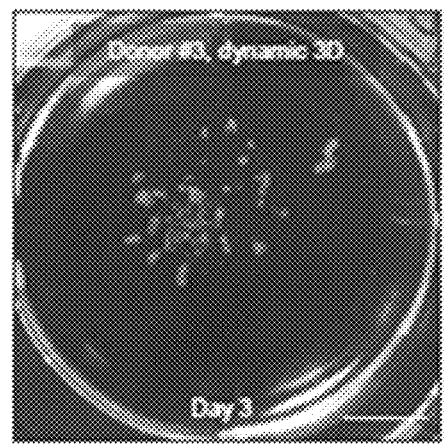

A significant challenge with culturing primary human cells is the existence of large inter-donor variations. It was studied if the AlgTubes could be used to expand T cells from different donors. T cells were cultured from three donors in parallel (Table 1). Cells were also cultured in static 3D and dynamic 3D for comparison. T cells were seeded at $1.0 \times 10^6$ cells/mL. In AlgTubes, T cells were continuously cultured for 14 days without passaging or splitting. T cells first formed small clusters (e.g. within the first 24 hours) that subsequently grew and filled the tubes, producing monodispersed (in radial direction) fibrous cell masses on day 14 (FIGS. 8A & 8D, FIGS. 9A & 9D, and FIGS. 10A & 10D). T cells expanded about 51, 123, 320-fold to yield around $0.51\times$, $1.2\times$, $3.2\times10^8$ cells/mL on day 6, 9 and 14, respectively (FIGS. 8G & 8H). There was minimal difference between the three donors (FIGS. 8A-8H, 9A-9F, and 10A-10F).

There was minimal difference between the three donors (FIGS. 8A-8H, 9A-9F, and 10A-10F). These results show all three culturing methods can be used to expand T cells, however, the AlgTubes result in significantly higher expansion fold and volumetric yield.

Low Cell Death and High Cell Proliferation in AlgTubes

Figure 11A:
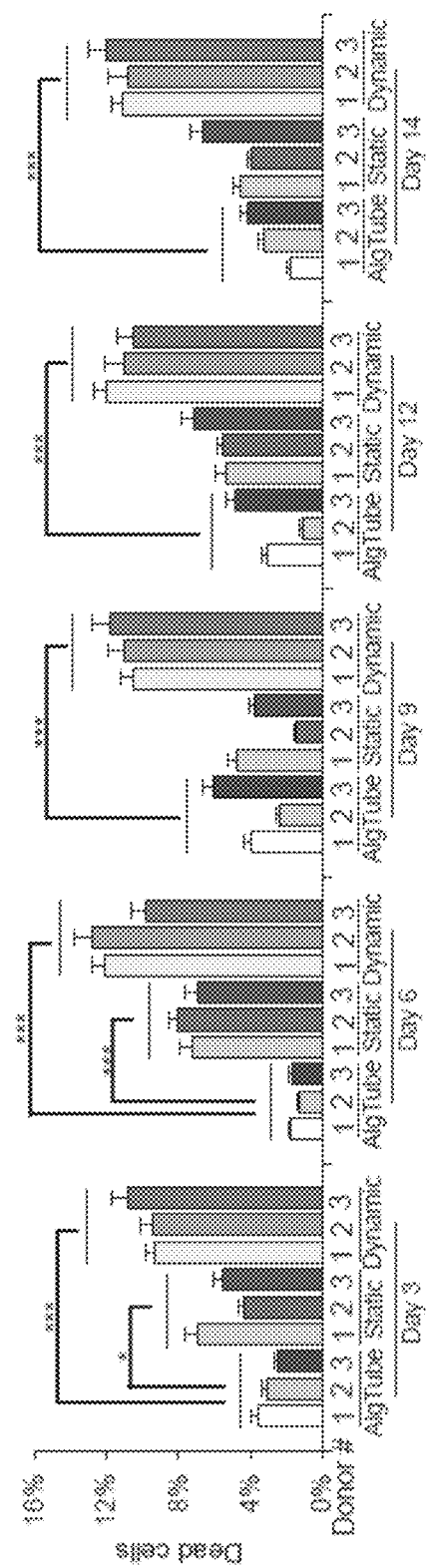
FIGS. 11A-11E depict cell death, cell cycle, cytokine release and DNA damage analysis.
Figure 11B:
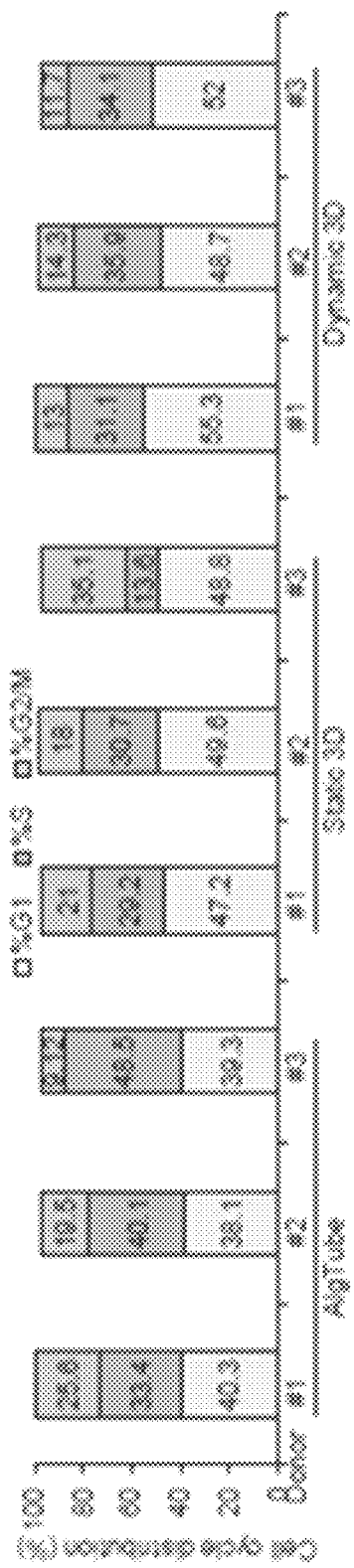

To study why T cells in AlgTubes expanded more efficiently (FIGS. 8G & 8H), cell death along the 14-day culture was evaluated. The culture medium was collected on day 3, 6, 9, 12 and 14 and the adenylate kinases (AKs) measured in the medium to quantify the dead cells. AKs, which are ubiquitous proteins presented in cells, are rapidly released into the culture medium upon damage of the plasma membrane. The percentage of dead cells (normalized to the initial cells) were significantly lower in AlgTubes than the other two methods. The dynamic 3D culturing had the most cell death (FIG. 11A). Cell proliferation was further analyzed through cell cycle analysis. On day 3 of the 14-day culture, around 39% cells in AlgTubes, ~49% cells in static 3D and ~53% cells in dynamic 3D were in G1 phase, indicating the cell proliferation was in the order of AlgTubes>static 3D>dynamic 3D (FIG. 11B). In short, the less cell death and higher cell proliferation lead to higher cell expansion and yield in AlgTubes.

Low T Cell Subtype Enrichment in AlgTubes

To study if the culturing changed cell phenotypes or enriched specific T cell subtypes, the typical T cell subtypes after the 14-day culture were analyzed using immunostaining and flow cytometry (FIG. 11C and FIGS. 12A-12C). The percentage of CD3+ T cells in AlgTubes and static 3D culturing were very similar to the original uncultured cells

TABLE 1

Donor Information

| Donor # | Supplier | Age | Gender | Race | Height | Weight (lbs) | ABO type | CD3+ | CD4+ | CD8+ |
|---|---|---|---|---|---|---|---|---|---|---|
| 1 | Astarte Biologics | 41 | Female | Caucasian | 5'6" | 208 | A | 98.2% | 76.6% | 19.3% |
| 2 | Astarte Biologics | 27 | Female | Caucasian | 5'5" | 200 | A | 99.0% | 62.5% | 33.6% |
| 3 | Astarte Biologics | 20 | Male | Caucasian | 5'6" | 145 | O | 99.2% | 70.4% | 26.5% |

For static 3D culturing, T cells quickly aggregated and grew as spherical cell aggregates with diameter between 100 to 800 pm (FIGS. 8B & 8E, FIGS. 9B & 9E, and FIGS. 10B & 10E). The aggregation slowed down cell growth. Thus, the aggregates were mechanically dissociated into small clusters on day 3, 6, 9 and 12 and split into multiple samples (e.g. seeded at $1.0 \times 10^6$ cells/mL after splitting) in order to increase the growth rate. With this protocol, T cells cumulatively expanded about 10, 35, 55-fold on day 6, 9 and 14, respectively (FIG. 8H). The maximal cell density could be achieved was about $3.5 \times 10^6$ cells/mL (FIG. 8G). There was minimal difference between the three donors (FIGS. 8A-8H, 9A-9F, and 10A-10F).

T cells severely aggregated or agglomerated in dynamic 3D culturing (FIGS. 8C & 8F, FIGS. 9C & 9F, and FIGS. 10C & 10F). To increase the growth rate, the aggregates were mechanically dissociated into small clusters on day 3, 6, 9 and 12 and split into multiple samples (e.g. seeded at $1.0 \times 10^6$ cells/mL after splitting). Through this protocol, T cells expanded cumulatively about 7, 17, 28-fold on day 6, 9 and 14, respectively (FIG. 8H). The maximal cell density could be achieved was about $2.5 \times 10^6$ cells/mL (FIG. 8G).

(e.g. 98%, 99% and 99% for donor #1, #2, and #3, respectively). The dynamic 3D culturing reduced the CD3+ T cells to 83%, 85% and 61% for donor #1, #2 and #3, respectively. The percentage of CD4+ T cells in AlgTubes were close to the original uncultured cells (e.g. 75%, 60%, 75% for donor #1, #2, and #3, respectively). The dynamic 3D culturing reduced the CD4+ T cells to 59%, 67% and 68% for donor #1, #2 and #3, respectively, and the static 3D culturing resulted in only 32%, 22%, and 18% CD4+ T cells for the three donors. The percentage of CD8+ T cells in AlgTubes were close to the original uncultured cells (e.g. 16%, 29%, 22% for donor #1, #2, and #3, respectively). The static 3D culturing increased the CD8+ T cells to 25%, 39% and 42% for donor #1, #2 and #3, respectively, and the dynamic 3D culturing resulted in only 38%, 29%, and 41% CD4+ T cells for the three donors. These results show that static 3D and dynamic 3D culturing, but not the AlgTubes, change the T cell phenotype or enrich specific subtypes. Phenotype or subtype changing during the culturing is highly unwanted for therapeutic cell production.

Normal Cytokine Release of Cultured T Cells

Figure 11C:
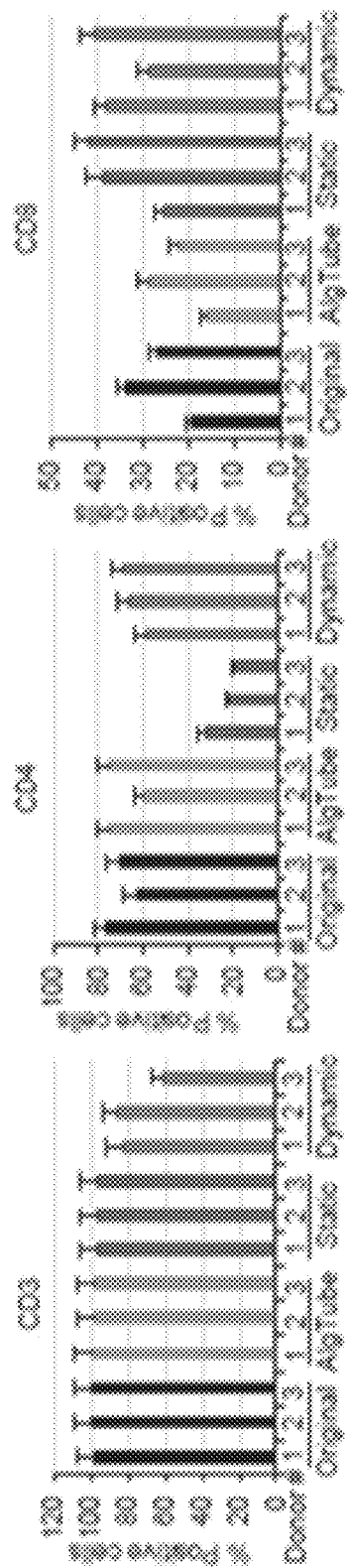
Figure 11D:
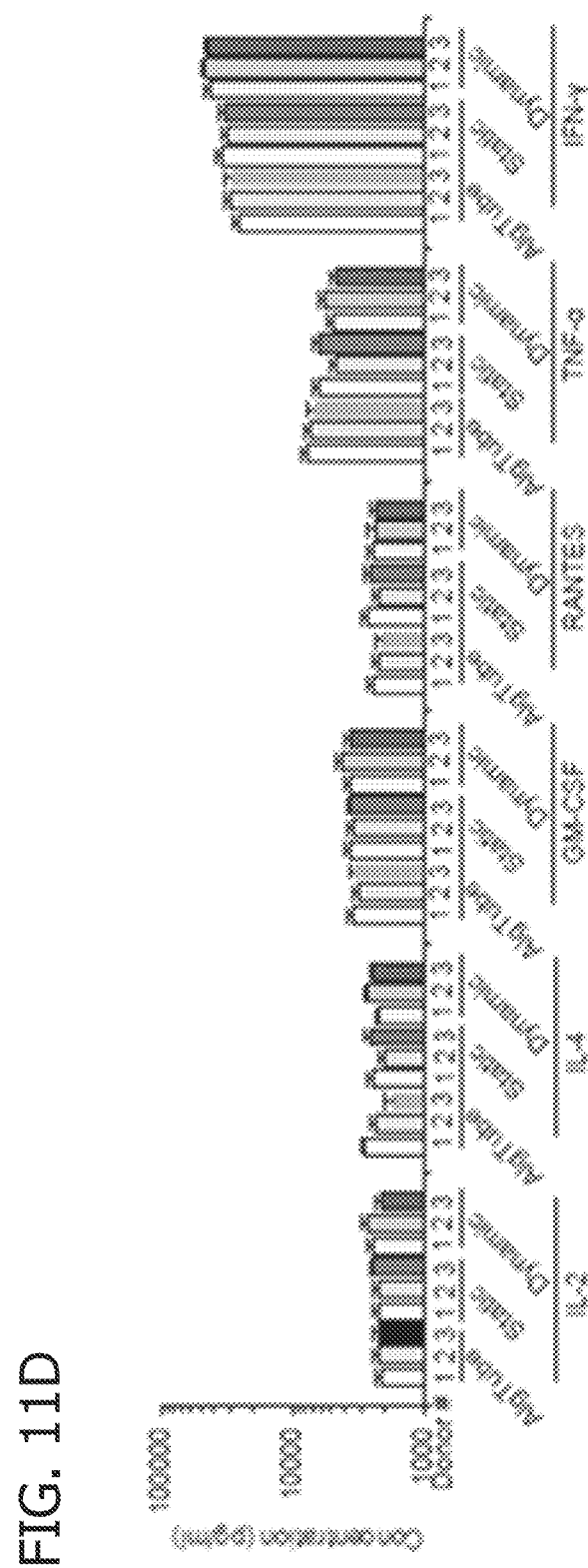
Figure 11E:
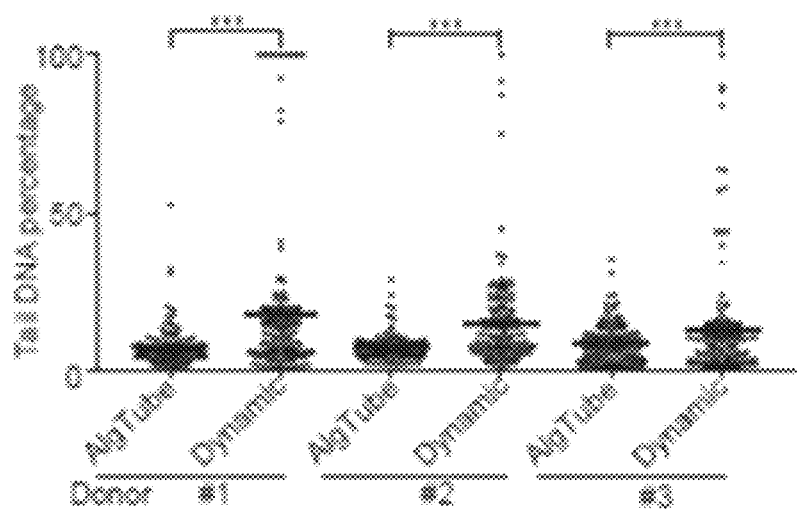
Figure 12A:
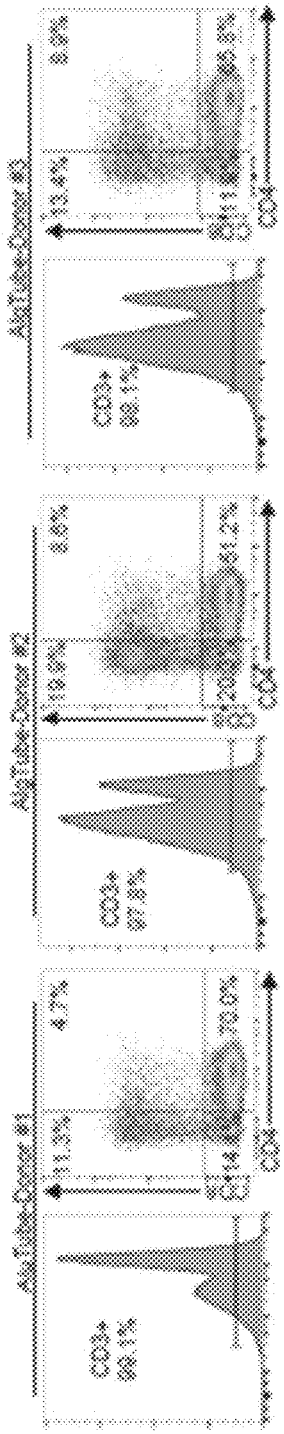
FIGS. 12A-12C depict flow cytometry analysis of T cells subtypes in the day 14 products at passage 1 cultured in AlgTubes, static 3D and dynamic 3D. Particularly.
Figure 12B:
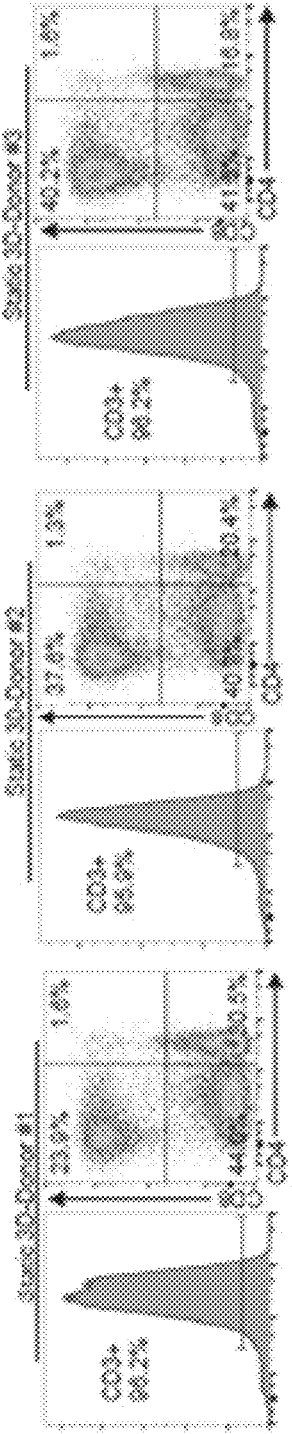
Figure 12C:
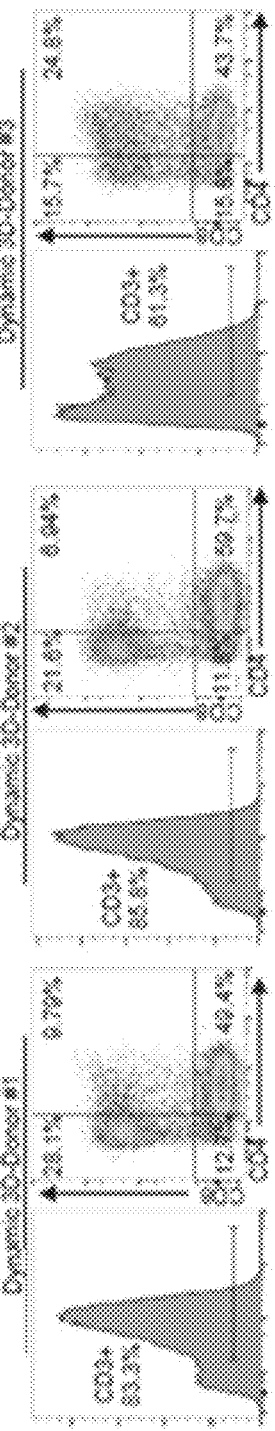
Figure 13A:
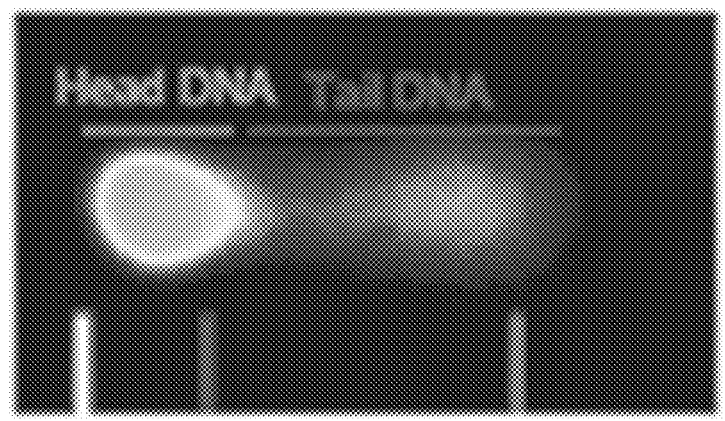
FIGS. 13A-13C depict DNA damage analysis. The double strand and single strand DNA breaks in day 6 T cells cultured in dynamic 3D suspension and AlgTubes were analyzed with Comet Assay.
Figure 13B:
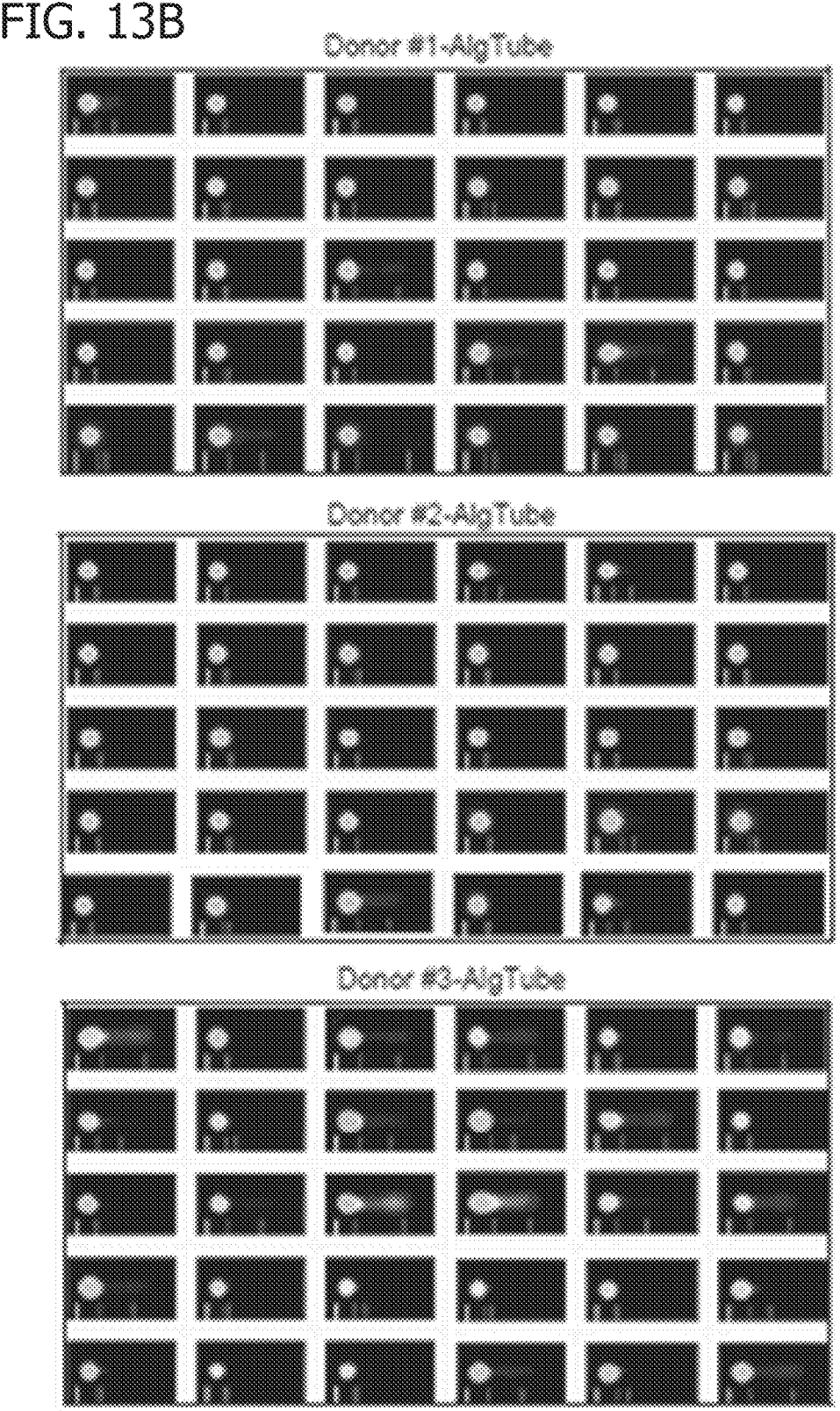
Figure 13C:
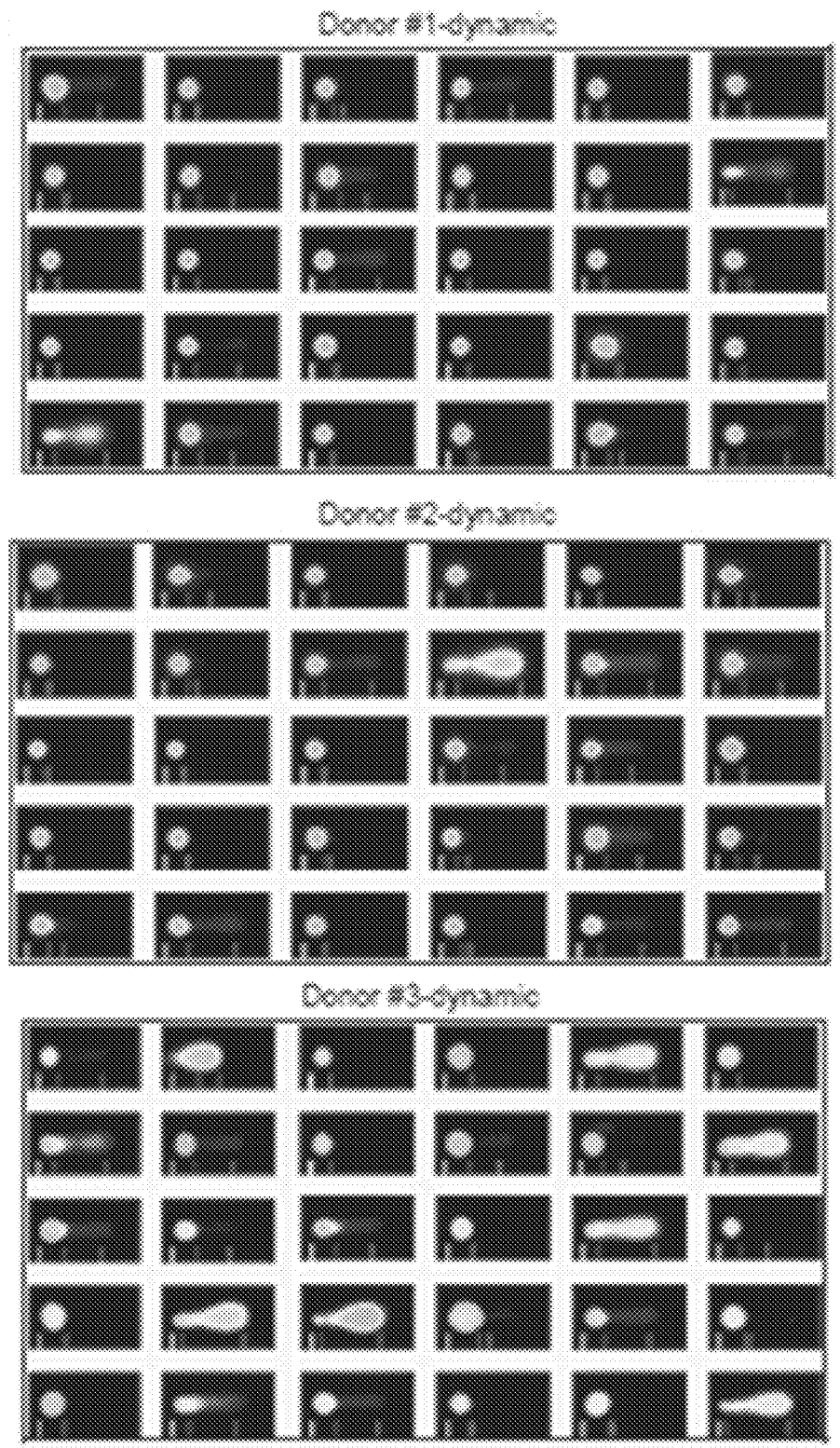
Figure 14A:
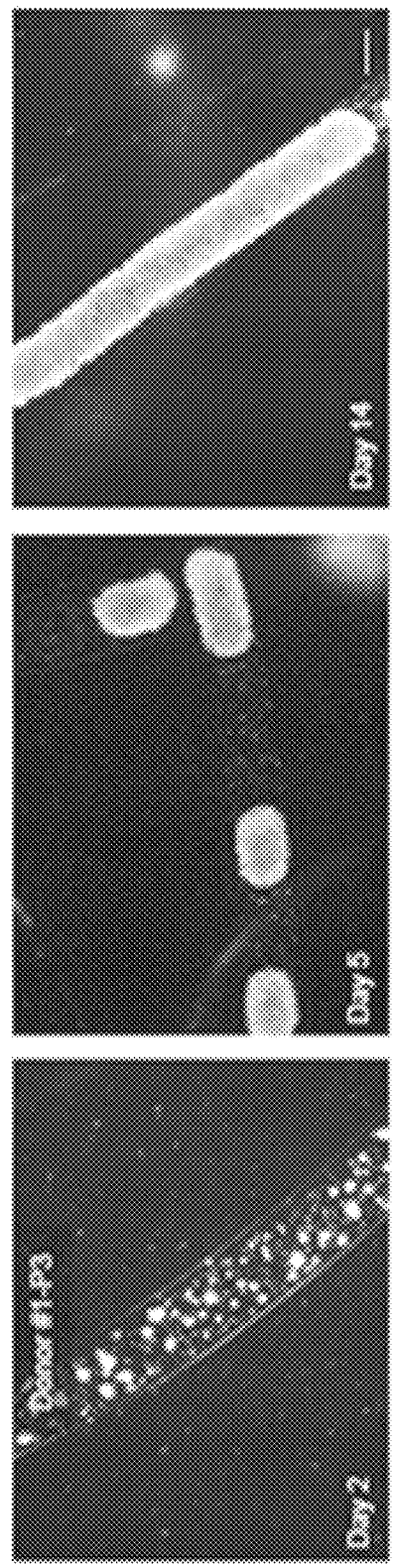
FIGS. 14A-14G depict long-term culturing of T cells from donor #1 and #2 in AlgTubes.
Figure 14B:
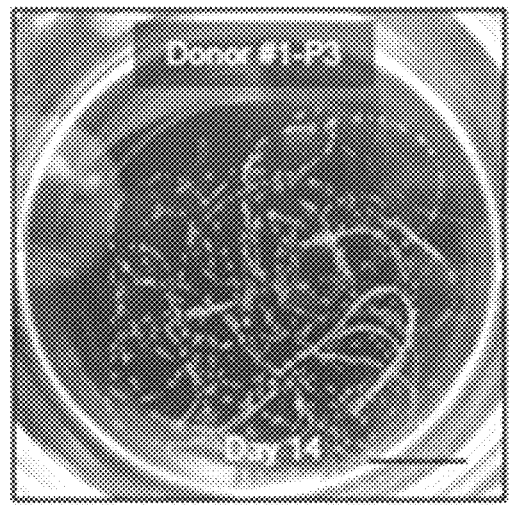
Figure 14C:
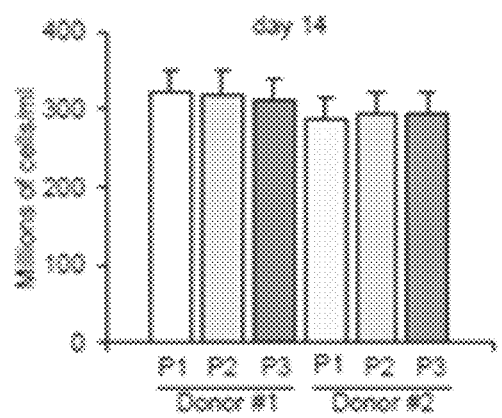
Figure 14D:
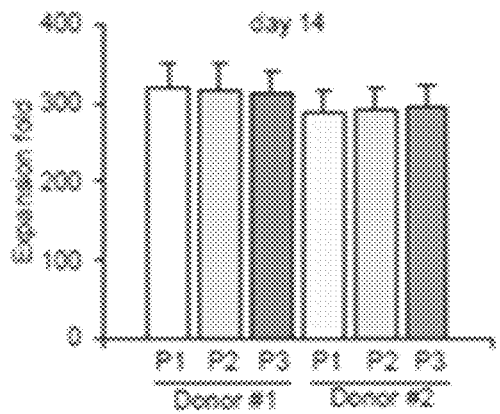
Figure 14E:
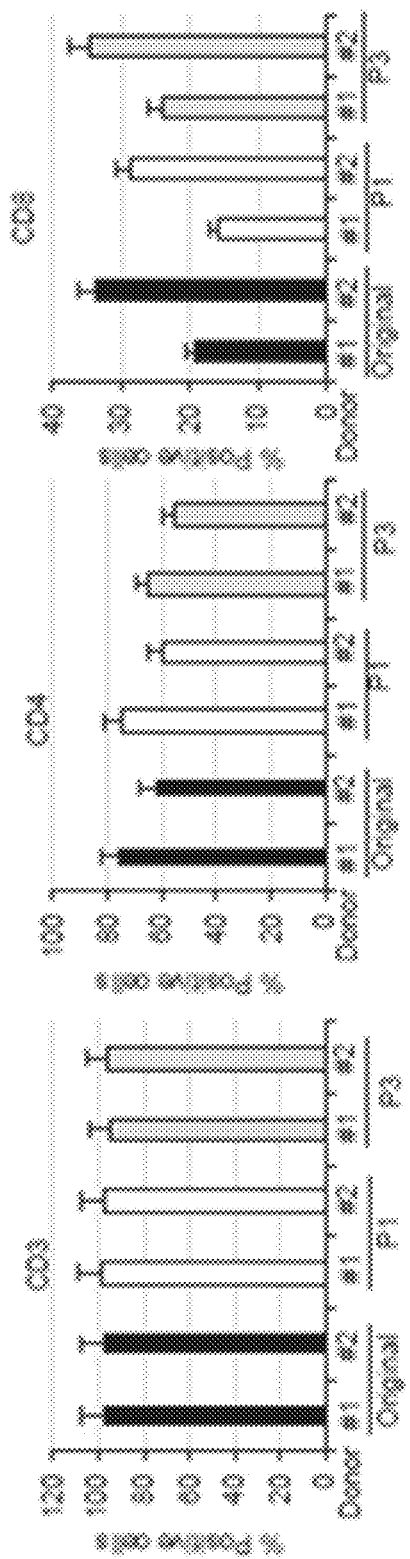
Figure 14F:
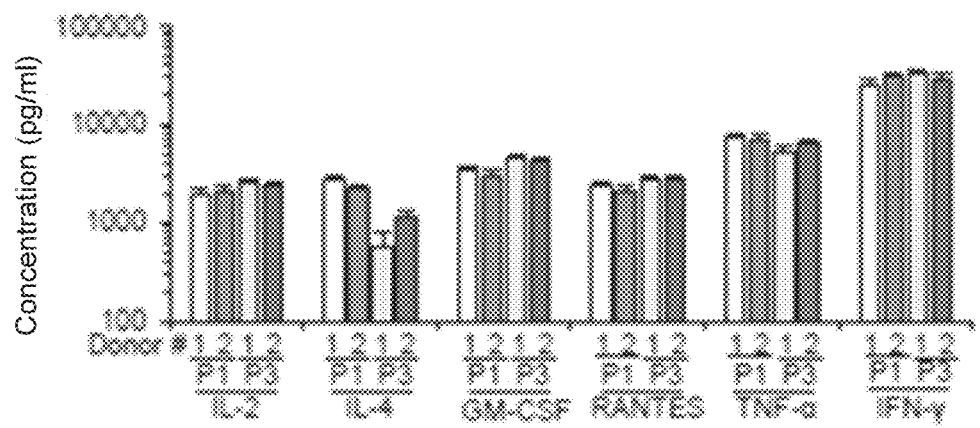
Figure 14G:
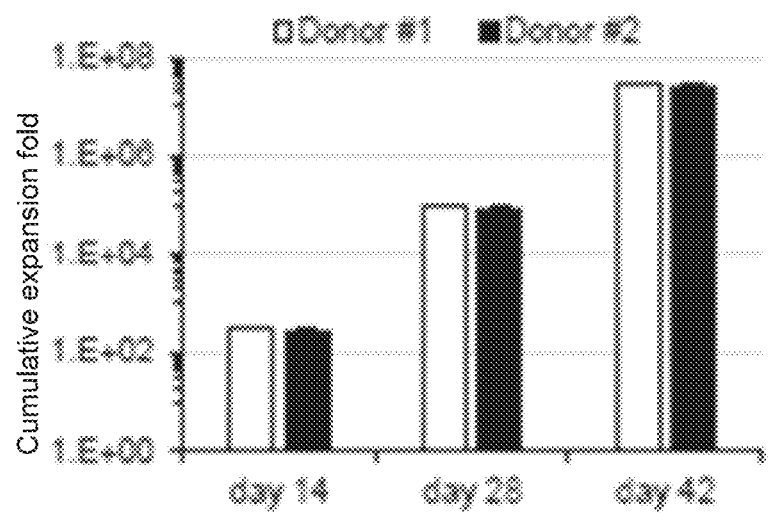

The day 14 culture medium was collected and used in the Human Cytokine Array to assess if T cells cultured in the three methods released the typical T cell cytokines (FIG. 11D). T cells from all culture methods showed a typical T cell cytokine profile characterized by the high production of interleukin-2 (IL-2), interleukin-4 (IL-4), interferon-y (IFN-y) and tumor necrosis factor-α (TNF-α). These results indicated that T cells expanded in AlgTubes were similar to these in static and dynamic 3D culturing in terms of cytokine releasing, an important property of functional T cells.

Low DNA Damages of T Cells in AlgTubes

To assess if the AlgTubes can improve the genetic stability of cultured cells, a comet assay was used to evaluate the DNA single and double strand breaks of the day 6 T cells (FIG. 11E and FIGS. 13A-13C). The comet assay (single-cell gel electrophoresis) is a simple method for measuring DNA strand breaks in eukaryotic cells. Single T cells were embedded in agarose hydrogel on a microscope slide, and were lysed with detergent and high salt to form nucleoids containing supercoiled loops of DNA. Electrophoresis resulted in structures resembling comets, which were recorded by fluorescence microscopy. The intensity of the comet tail relative to the head is proportional to the number of DNA breaks. The results showed T cells cultured in AlgTubes had significantly less DNA breaks than cells from dynamic 3D culturing (FIG. 11E and FIGS. 13A-13C), indicating the cell-friendly AlgTubes can improve the genetic stability of cultured T cells.

Long-Term Culturing T Cells in AlgTubes

If T cells could be cultured in AlgTubes for long terms was also evaluated. T cells were cultured for 3 passages, total of 42 days in AlgTubes (FIGS. 14A-14G and FIGS. 15A-15DF). T cells at passage 3 had very similar morphology, viability, cell growth rate, yield, subtype distribution and cytokine releasing to these at passage 1. The results show prolonged culture can be performed with AlgTubes if large numbers of T cells are needed.

Automated Production of T Cells in AlgTube-Based Device

A prototype device for automated T cell production (FIG. 16A) was built. On day 1, three milliliters of AlgTubes containing T cells from each donor were processed and contained in one closed 50 mL conical tube (FIG. 16D), where T cells were expanded for 14 days (FIG. 16E). On day 14, EDTA solution was pumped into the conical tube to dissolve the AlgTubes and the cell mass was collected through mild centrifugation (e.g. 100 g for 2 minutes) for downstream application (FIG. 16F). During the 14-day culture, the cell culture medium was stored in a plastic bellow bottle that could be pressed to flow the medium into the conical tube or released to withdraw the medium from the conical tube, respectively (FIGS. 16A-16C). The pressing and releasing speed, as well as the duration of the interval between the pressing and releasing, were programmed and controlled by the controller (FIG. 16A). Since the AlgTubes have similar density with the cell culture medium, they were uniformly suspended and dispersed in the medium when the medium was pumped into the bioreactor. They became collected and contact with each other when the medium was withdrawn from the bioreactor. This periodic dispersion and collection of AlgTubes was designed to enhance the medium mixing. T cell grew well and yielded ~3.0×10$^8$ cell/mL by day 14 (FIGS. 16E & 16F). Three 50 mL conical tubes were used for expanding T cells from three donors. More tubes could be used to produce T cells from many donors.

Discussion

When culturing human cells, such as human pluripotent stem cells (hPSCs) and human mesenchymal stem cells (MSCs), with 3D suspension culturing, a challenge is the uncontrolled cellular aggregation. Human cells usually have strong cell-cell interactions that make them aggregate. Suspended cells tend to form large cell agglomerates (i.e., agglomeration). Agglomeration leads to inhomogeneity in cell aggregate size and is detrimental to cell culture. For instance, the transport of nutrients, oxygen, and growth factors to, and the metabolic waste from, cells located at the center of large cell agglomerates (e.g., >400 μm diameter) become insufficient, leading to slow cell growth, apoptosis, and phenotype change. The results showed T cells also formed agglomerates in 3D suspension culturing (FIGS. 8A-8H, 9A-9F, and 10A-10F). Whether the observed high cell death, slow cell proliferation and cell phenotype changes in static and dynamic 3D suspension culturing (FIGS. 11A-11E) came from the cell agglomeration should be made clear in the future.

Agitation (or shaking or rocking, typically in the range of 75 to 120 rpm) is usually used to enhance the mass transport and reduce cell agglomeration in 3D suspension culturing. However, agitation cannot eliminate cell agglomeration. In addition, agitation generates complicated hydrodynamic conditions including the medium flow direction, velocity, shear force, and chemical environment. These conditions vary spatially and temporally, resulting in locations (e.g. close to the vessel wall) with critical stresses that induce cell death and phenotype changes, low cell viability, growth, and yield. Further, the hydrodynamic conditions in a bioreactor are sensitive to many factors including the impeller geometry, size and position, the bioreactor geometry and size, the positions of probes for pH, temperature and oxygen, the medium viscosity, and the agitation rate. They are currently not well understood and are hard to control. Additionally, how different types of cells respond to the hydrodynamic conditions is not well known and is hard to study. These knowledge gaps results in culture inconsistency and difficulty in scaling up cell production. In this Example, a mild agitation (e.g. ~15 rpm to mimic the WAVE bioreactor) was used. This mild agitation led to more severe cell agglomeration compared to static 3D culturing (FIGS. 8A-8H, 9A-9F, and 10A-10F). The hydrodynamic stresses might also contribute to the observed high cell death, slow cell proliferation and cell phenotype changes in dynamic 3D suspension culturing (FIGS. 11A-11E).

The AlgTubes are designed to simultaneously eliminate the cell agglomeration and hydrodynamic stresses. First, the AlgTubes produce mono-dispersed (in radial diameter) cell masses that can be precisely controlled in any range between 100 μm to 400 μm. This can ensure efficient mass transport to all cells (FIGS. 7A-7F). Second, cells in AlgTubes are protected from hydrodynamic stresses by the hydrogel shells. This reduces the hydrodynamic-conditions-induced negative effects. The protection from the AlgTubes, scaling up the culture volume, did not change the cell grow rate and automating the production could be readily achieved. Lastly, the tubes provide free space for cells to interact with each other and expand, leading to extremely high volumetric yield, which is about 30-fold of the current state-of-art (FIGS. 8G & 8H).

The use of alginates for processing the tubes makes this technology scalable, cost-effective, Good Manufacture Practice (GMP)-compatible and commercially viable. GMP compliance is required for producing therapeutic cells by regulatory agencies (e.g., FDA). High quality and quantity alginates are available and affordable. Alginates are non-toxic to cells and have been used in clinics. They can be instantly crosslinked to process large-scale AlgTubes. The resulting hydrogel tubes are mechanically and chemically stable and suitable for culturing cells in large-scale and for long-term. Additionally, the tubes can be dissolved easily with cell-compatible EDTA solution to release the product, and are transparent so that the cell growth can be monitored with microcopies.

The conceptual and technical innovations of AlgTubes lead to its high culture efficiency. T cells could be cultured with much higher expansion and yield than other culture methods (FIGS. 8G & 8H). For instance, T cells expanded cumulatively 320, 55, 28 fold in a 14-day culture in AlgTubes, static 3D and dynamic 3D culturing, respectively (FIG. 8H). The maximal volumetric yield was $3.2 \times 10^8$ cells/mL, $3.5 \times 10^6$ cells/mL, $2.5 \times 10^6$ cells/mL in AlgTubes, static 3D and dynamic 3D culturing, respectively (FIG. 8G). The high expansion rate and yield have large impacts on T cell production. For instance, T cells required for one patient (e.g. ~$10^9$ to $10^{10}$ cells) can be produced with merely 3 to 30 mL alginate hydrogel tubes that can be contained in one closed 50 mL conical tube. T cells for many patients can be automatically produced with corresponding numbers of 50 mL tubes in parallel. Automating the production can significantly reduce the production cost and variation, while increase the production capacity for T cells to make the adoptive immunotherapy broadly available and affordable. In addition, the results showed T cells cultured in AlgTubes had much less phenotype changing or subtype enrichment (FIG. 11C). Phenotype changing can lead to large variations in the product efficacy and potency. T cells in AlgTubes had minimal DNA damages (FIG. 11E), indicating better product safety and quality. Further, T cells could be cultured for long-term to generate more cells (FIGS. 14A-14G). In summary, the AlgTubes will significantly advance the adoptive immunotherapy and will be of broad interest to individual laboratories, institutions, and biotechnology companies working on adoptive immunotherapy.

Example 2

In this Example, a cell expansion system was designed for scalable endothelial cells (ECs) production.

Materials and Methods 2 mL of hPSCs solution in AlgTube were suspended in a 50 mL conical culture tube with septum cap. hPSCs were cultured in E8 medium with 5% $CO_2$, 21% $O_2$ at 37° C. for 5 days. E8 medium was removed and replaced with EC differentiation medium for 3 days, followed by ECs induction medium for 2 days. For the cell expansion system, medium was stored in a bellow bottle that was periodically pressed to flow the medium into, or released to withdraw, the medium from, the 50 mL culture tube. On day 10, hydrogel tubes were dissolved by adding 0.5 mM EDTA buffer. Cell masses were pelleted by centrifugation. Cell masses were dissociated into single cells through incubating in Accutase at 37° C. for 10 minutes. Magnetic beads coated with anti-SSEA4 antibodies were added to pull down the undifferentiated SSEA4+ hPSCs with a magnetic cell separator. The supernatant was transferred into a new tube. Cells were pelleted by spinning at 300 g for 5 minutes and transported to the surgery room for injection.

Results:

Using the alginate hydrogel as a scaffold, an exemplary cell expansion system for scalable ECs production was designed (FIGS. 17A & 17B). On day 0, single hPSCs mixed with 1.5% HA solution and 1.5% alginate solution were pumped into the central and side channel of the home-made micro-extruder respectively, and extruded into a $CaCl_2$ buffer (100 mM). Cells were cultured in E8 medium for 5 days, followed by additional 5 days of ECs differentiation medium. On day 10, alginate hydrogel were dissolved by adding 0.5 mM EDTA solution for 5 minutes. Cell masses were pelleted by spinning the tube at 100 g for 3 minutes. Cell masses were dissociated into single cells through treating with Accutase at 37° C. for 10 minutes. Magnetic beads coated with anti-SSEA4 antibodies were then added to the tube to pull down the undifferentiated SSEA4+ hPSCs with a magnetic cell separator (FIGS. 17C-17G). Phase image and live/dead cell staining showed few dead cells (FIGS. 17H & 17I). Flow cytometer analysis and immunostaining showed 82.6% of the day 10 cells were ECs (FIGS. 17J & 17K). When transplanted subcutaneously with a Matrigel matrix, ECs formed nice vascular structures (FIG. 17L).

Example 3

In this Example, an exemplary cell expansion system for scalable neural stem cells (NSCs) production was designed.

Figure 18G:
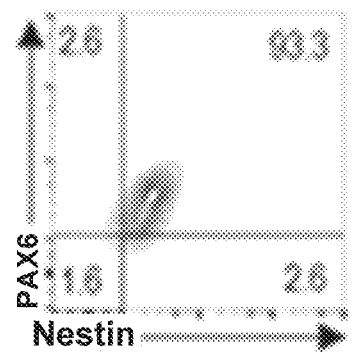
Figure 18H:
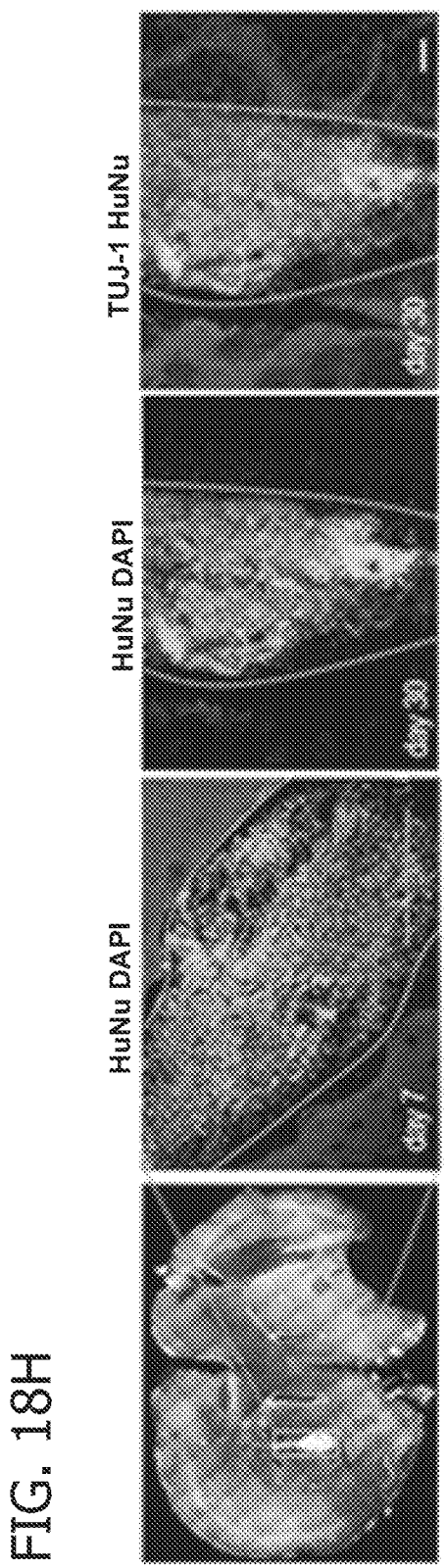

Materials and Methods 2 mL of hPSCs solution in AlgTube were suspended in a 50 mL conical culture tube with septum cap. hPSCs were cultured in E8 medium with 5% $CO_2$, 21% $O_2$ at 37° C. for 5 days. Medium was stored in a bellow bottle that was periodically pressed to flow the medium into, or released to withdraw, the medium from, the 50 mL culture tube. E8 medium was removed and replaced with neural induction medium for 7 days. On day 12, hydrogel tubes were dissolved by adding 0.5 mM EDTA buffer. Cell masses were pelleted by centrifugation. Cell masses were dissociated into single cells through incubating in Accutase at 37° C. for 10 minutes. Magnetic beads coated with anti-SSEA4 antibodies were added to pull down the undifferentiated SSEA4+ hPSCs with a magnetic cell separator. The supernatant was transferred into a new tube. Cells were pelleted Results:

Using the alginate hydrogel as a scaffold, an exemplary cell expansion system for scalable NSCs production was designed (FIGS. 18A & 18B). On day 0, single hPSCs mixed with 1.5% HA solution and 1.5% alginate solution were pumped into the central and side channel of the home-made micro-extruder respectively, and extruded into a $CaCl_2$ buffer (100 mM). Cells were cultured in E8 medium for 5 days, followed by additional 7 days of NSCs induction medium. On day 12, alginate hydrogel were dissolved by adding 0.5 mM EDTA solution for 5 minutes. Cell masses were pelleted by spinning the tube at 100 g for 3 minutes. Cell masses were dissociated into single cells through treating with Accutase at 37° C. for 10 minutes. Magnetic beads coated with anti-SSEA4 antibodies were then added to the tube to pull down the undifferentiated SSEA4+ hPSCs with a magnetic cell separator (FIG. 18C). Phase image and live/dead cell staining showed no or undetectable dead cells (FIGS. 18D & 18E). Immunostaining and flow cytometry analysis showed 93.3% of the day 12 cells were NSCs (FIGS. 18F & 18G). Purified cells in the supernatant were transferred into a new, close tube and transported to the surgical room. Purified NSCs were injected into the striatum of Sprague dawley rats with a stereotactic injector. 7 days post-transplantation, substantial numbers of human unclear antigen positive cells were found in the rat brain, and 30 days after transplantation, large numbers of HuNu+ and TUJ-1+ cells were found in the rat brain (FIG. 18H).

Example 4

In this Example, an exemplary cell expansion system was designed for personalized cell production.

Materials and Methods

Production in Single Conical Tube

On day 0, reprogramming factors (hOSKUL+EGFP) were delivered to fibroblasts through electroporation and ~$2\times10^7$ cells/mL hydrogel were processed into AlgTubes into a closed 50-mL conical tube. Cells were reprogrammed for 20 days, expanded for 10 days and differentiated into DA progenitors for 11 days. On day 41, 0.5 mM EDTA was infused to dissolve the tubes. Accutase was then infused to dissociate the fibrous cell mass into single cells. Magnetic beads coated with anti-SSEA4 antibodies were then added into the tube to pull down the undifferentiated SSEA4+ iPSCs with a magnetic cell separator.

Transplant DA Progenitors

All animal protocols were approved by the Animal Care and Use Committee of the University of Nebraska, Lincoln. All experimental procedures involving animals were carried out in accordance with the guidelines of the Institutional Animal Care and Use Committee of the University of Nebraska, Lincoln. Sprague Dawley rats (6-8 weeks, female) were obtained from Charles River. Animals received intraperitoneal cyclosporine A (10 mg/kg, LC Laboratories, #C-6000) injection starting 1 day before transplantation. For transplantation, animals were anesthetized with 2-4% isoflurane. $3\times10^5$ cells suspended in 4 µl PBS were injected into the striatum (AP+0.5 mm; ML±3.0 mm; DV−6 mm) at 0.5 µl/minute using a 10 µl Hamilton syringe (Hamilton Company, USA) with a stereotaxic frame (RWD Life Science Inc.). After 6 weeks, rats were anesthetized with ketamine/xylazine and perfused with PBS followed by 4% paraformaldehyde. After fixation, the brain was serially sectioned (40 µm in thickness) with a Leica cryosection machine, and free-floating ections were stained with antibodies.

Results:

Based on the above successful studies, a cell expansion system for integrated iPSC generation, expansion and differentiation was designed. The system consists of a mechanic stage, a controller, a bellow bottle and a 50-mL conical tube (FIG. 19A). Medium was stored in the plastic bellow bottle that could be pressed to flow the medium into, or released to withdraw, the medium from the conical tube. The controller could be programmed for the pressing and releasing speed, as well as the duration of the interval between the pressing and releasing (FIG. 19A). Since AlgTubes have similar density with the cell culture medium, they were uniformly suspended and dispersed in the medium when the medium was pumped into the conical tube. They became collected and contacted with each other when the medium was withdrawn from the conical tube. This periodic dispersion and collection of AlgTubes was designed to enhance the medium mixing. On day 0, reprogramming factors were delivered to fibroblasts through electroporation and cells were processed into AlgTubes into the closed 50-mL conical tube. Cells were reprogrammed for 20 days, expanded for 10 days and differentiated into DA progenitors for 11 days. On day 41, 0.5 mM EDTA was infused into the conical tube to dissolve AlgTubes. Accutase was then infused to digest the cell mass into single cells. Magnetic beads coated with anti-SSEA4 antibodies were then added into the conical tube to pull down the undifferentiated SSEA4+ iPSCs with a magnetic cell separator. Purified cells were transplanted into brains of Sprague dawley rats with a stereotactic injector (FIG. 19B). Very few cell deaths occurred during the production (FIGS. 19C & 19D). ~90% produced cells were LMX1A+/FOXA2+ (FIGS. 19E & 19F). 6 weeks post-transplantation, these cells survived well by HuNu staining (FIG. 19G). A large percentage of the cells matured into TH+ DA neurons (FIG. 19H).

What is claimed is:

1. A cell expansion system for expanding cells, the system comprising:
   a cap connected to a tubular housing defining an internal space, the cap comprising: an extruder comprising at least a first inlet and at least a second inlet, the extruder disposed within the internal space defined by the cap and the tubular housing such that distal ends of the first inlet and the second inlet are connected to the cap at respective openings in the cap, the first inlet operable for introducing a cell solution into the cap, the at least second inlet operable for introducing a hydrogel-forming solution into the cap; and
   the tubular housing in fluid connection with the extruder, wherein the tubular housing comprises a cell compatible buffer.

2. The system of claim 1, wherein the tubular housing further comprises a mesh.

3. The system of claim 1, wherein the cell solution comprises cells selected from the group consisting of mammalian embryonic stem cells, mammalian induced pluripotent stem cells, mammalian naive pluripotent stem cells, cells differentiated from mammalian embryonic stem cells, mammalian induced pluripotent stem cells and mammalian naive pluripotent stem cells, mammalian cells reprogrammed from other cell types, mammalian primary cells, human umbilical vein endothelial cells, cancer cells, T cells, mammalian tissue stem cells, mammalian cell lines, insert cells, plant cells, yeast and bacterial cells.

4. The system of claim 1, wherein the hydrogel-forming solution is an alginate solution comprising alginate polymer material selected from the group consisting of alginate acid polymers, sodium alginate polymers, modified alginate polymers, and combinations thereof.

5. The system of claim 4, wherein the alginate solution comprises from about 0.01% (w/v) to about 20% (w/v) alginate.

6. The system of claim 1, wherein the hydrogel-forming solution comprises a material selected from polyethylene glycol, poly (vinyl alcohol), and combinations thereof.

7. The system of claim 1, wherein the cell compatible buffer comprises at least one of calcium ions and barium ions.

8. The system of claim 7, wherein the cell compatible buffer comprises at least one of $CaCl_2$ and $BaCl_2$.

9. A method of expanding cells, the method comprising culturing cells in the cell expansion system of claim 1.

10. The method of claim 9 comprising:
    extruding the cell solution and the hydrogel-forming solution into a cell compatible solution, the cell compatible solution crosslinking polymers within the hydrogel-forming solution to form hydrogel fibers;
    suspending the fibers including cells from the cell solution in cell culture medium or cell compatible buffer in the tubular housing; and
    culturing the cells.

11. The method of claim 10, wherein the hydrogel-forming solution is an alginate solution prepared by suspending alginate polymers in a solution at a concentration of from about 0.01% to about 20% by weight/volume alginate polymers.

12. The method of claim 10, wherein the hydrogel-forming solution is prepared using a polymer material selected from polyethylene glycol, poly (vinyl alcohol), and combinations thereof.

13. The method of claim 10, wherein the cell compatible solution comprises one or more of calcium ions and barium ions.

14. The method of claim 10 further comprising releasing the cultured cells from the hydrogel fibers comprising dissolving the hydrogel fibers.

15. The method of claim 14, wherein dissolving the hydrogel fibers comprises
chemically dissolving the hydrogel fibers using a chemical dissolvent selected from the group consisting of ethylenediaminetetraacetic acid (EDTA), ethylene glycol tetraacetic acid (EGTA), and an alginate lyase solution.

16. The method of claim 14, wherein dissolving the hydrogel fiber comprises physically dissolving the hydrogel fiber using a mechanical force.

17. The method of claim 10, wherein the cell solution comprises cells selected from the group consisting of mammalian embryonic stem cells, mammalian induced pluripotent stem cells, mammalian naive pluripotent stem cells, cells differentiated from mammalian embryonic stem cells, mammalian induced pluripotent stem cells and mammalian naive pluripotent stem cells, mammalian cells reprogrammed from other cell types, mammalian primary cells, human umbilical vein endothelial cells, cancer cells, T cells, mammalian tissue stem cells, mammalian cell lines, insert cells, plant cells, yeast and bacterial cells.

18. The method of claim 10, wherein suspending the fibers including cells from the cell solution is in cell compatible buffer comprising at least one of calcium ions and barium ions.

19. The method of claim 18, wherein the cell compatible buffer comprises at least one of $CaCl_2$ and $BaCl_2$.

* * * * *